US008216815B2

(12) United States Patent
McDaniel et al.

(10) Patent No.: US 8,216,815 B2
(45) Date of Patent: Jul. 10, 2012

(54) PRODUCTION OF FATTY ALCOHOLS WITH FATTY ALCOHOL FORMING ACYL-COA REDUCTASES (FAR)

(75) Inventors: Robert McDaniel, Palo Alto, CA (US); Behnaz Behrouzian, Sunnyvale, CA (US); Louis Clark, San Francisco, CA (US); Douglas Hattendorf, Mountain View, CA (US); Fernando Valle, Burlingame, CA (US)

(73) Assignee: Codexis, Inc., Redwood City, CA (US)

( * ) Notice: Subject to any disclaimer, the term of this patent is extended or adjusted under 35 U.S.C. 154(b) by 91 days.

(21) Appl. No.: 12/825,939

(22) Filed: Jun. 29, 2010

(65) Prior Publication Data

US 2011/0000125 A1 Jan. 6, 2011

Related U.S. Application Data

(60) Provisional application No. 61/221,934, filed on Jun. 30, 2009, provisional application No. 61/315,380, filed on Mar. 18, 2010.

(51) Int. Cl.
| | |
|---|---|
| *C12P 7/42* | (2006.01) |
| *C12P 21/06* | (2006.01) |
| *C12P 21/04* | (2006.01) |
| *C12Q 1/68* | (2006.01) |
| *C12Q 1/26* | (2006.01) |
| *C12N 9/02* | (2006.01) |
| *C12N 1/20* | (2006.01) |
| *C12N 15/00* | (2006.01) |
| *C07H 21/04* | (2006.01) |

(52) U.S. Cl. ...... 435/146; 435/6.1; 435/189; 435/252.3; 435/320.1; 435/440; 435/69.1; 435/71.1; 435/25; 536/23.2

(58) Field of Classification Search .................. None
See application file for complete search history.

(56) References Cited

U.S. PATENT DOCUMENTS

| 5,370,996 A | 12/1994 | Metz et al. |
| 6,828,475 B1 | 12/2004 | Metz et al. |
| 2003/0097686 A1 | 5/2003 | Knauf et al. |
| 2009/0148918 A1 | 6/2009 | Trimbur et al. |
| 2010/0203614 A1 | 8/2010 | Wahlen et al. |

FOREIGN PATENT DOCUMENTS

| WO | WO 2007/136762 A2 | 11/2007 |
| WO | WO 2009/140695 A1 | 11/2009 |
| WO | WO 2011/019858 A1 | 2/2011 |

OTHER PUBLICATIONS

Branden et al. Introduction to Protein Structure, Garland Publishing Inc., New York, p. 247, 1991.*
UniProt Accession No. A6EVI7, EMBL, Jul. 2007.
Doan, Thuy T.P. et al.; "Functional expression of five *Arabidopsis* fatty acyl-CoA reductase genes in *Escherichia coli*"; 2009, *Journal of Plant Physiology*, vol. 166, pp. 787-796.
Metz, James G. et al.; "Purification of a Jojoba Embryo Fatty Acyl-Coenzyme A Reductase and Expression of its cDNA in High Erucic Acid Rapeseed"; 2000, *Plant Physiology*, vol. 122, pp. 635-644.
Moto, Kenichi et al.; "Pheromone gland-specific fatty-acyl reductase of the silkmoth, *Bombyx mori*"; 2003, *PNAS*, vol. 100, No. 16, pp. 9156-9161.
Reiser, Steven et al.; "Isolation of Mutants of *Acinetobacter calcoaceticus* Deficient in Wax Ester Synthesis and Complementation of One Mutation with a Gene Encoding a Fatty Acyl Coenzyme A Reductase"; 1997, *Journal of Bacteriology*, vol. 179, No. 9, pp. 2969-2975.
Steen, Eric J. et al.; "Microbial production of fatty-acid-derived fuels and chemicals from plant biomass"; 2010, *Nature*, vol. 463, pp. 559-563.
Teerawanichpan, Prapapan et al.; "Fatty Acyl-CoA Reductase and Wax Synthase from *Euglena gracilis* in the Biosynthesis of Medium-Chain Wax Esters"; 2010, *Lipids*, vol. 45, pp. 263-273.
Wahlen, Bradley D. et al.; "Purification, Characterization, and Potential Bacterial Wax Production Role of an NADPH-Dependent Fatty Aldehyde Reductase from *Marinobacter aquaeolei* VT8"; 2009, *Applied and Environmental Microbiology*, vol. 75, No. 9, pp. 2758-2764.
"Hypothetical protein GOS_1311075 [marine metagenome]"; *GenBank: EDD40059.1*, 2007, 2 pages.
"Fatty-acyl reductase [Bombyx mori]"; *GenBank: BAC79425.1*, 2003, 2 pages.
"*Bermanella marisrubri* strain RED65 1100007010788, whole genome shotgun sequence"; *GenBank: AAQH010000001.1*, 2006, 1 page.
"*Marinobacter algicola* DG893 1103407001931, whole genome shotgun sequence"; *GenBank: ABCP01000001.1*, 2007, 1 page.
"Dehydrogenase domain-containing protein [*Hahella chejuensis* KCTC 2396]"; *NCBI Reference Sequence: YP 436183.1*, 2005, 2 pages.
"Male sterility C-terminal domain [*Marinobacter aquaeolei* VT8]"; *GenBank: ABM19299.1*, 2006, 2 pages.
"Hypothetical protein Maqu_2220 [*Marino aquaeolei* VT8]"; *NCBI Reference Sequence: YP 959486.1*, 2007, 2 pages.
Aarts, Mark G.M., et al., "The *Arabidopsis* Male Sterility 2 protein shares similarity with reductases in elongation/condensation complexes," *The Plant Journal* (1997) 12(3): 615-623.

\* cited by examiner

*Primary Examiner* — Yong Pak
(74) *Attorney, Agent, or Firm* — Kilpatrick Townsend & Stockton LLP

(57) ABSTRACT

The disclosure relates to methods of producing fatty alcohols from recombinant host cells comprising genes encoding heterologous fatty acyl-CoA reductase (FAR) enzymes. The disclosure further relates to FAR enzymes and functional fragments thereof derived from marine bacterium and particularly marine gamma proteobacterium such as *Marinobacter* and *Oceanobacter*; polynucleotides encoding the FAR enzymes and vectors and host cells comprising the same.

14 Claims, 13 Drawing Sheets

FIG.2

Codon optimized *M. algicola* DG893 FAR DNA (SEQ ID NO: 1)

ATGGCTACTCAACAACAACAGAACGGTGCATCTGCATCCGGCGTCTTGGAACAACTTCGT
GGAAAGCACGTTCTTATCACAGGTACTACCGGATTTTGGGCAAAGTGGTTCTGGAAAAG
TTGATTCGTACTGTTCCGGATATTGGAGGTATTCATCTGCTGATTCGTGGCAATAAACGT
CATCCAGCCGCTCGTGAACGTTTCCTGAACGAAATTGCGTCCTCCTCCGTCTTCGAACGT
TTGCGTCACGATGATAATGAAGCCTTCGAGACCTTCTTGGAAGAACGTGTTCACTGTATT
ACCGGTGAGGTTACTGAATCCCGTTTTGGTTTGACACCTGAACGTTTTCGTGCTTTGGCC
GGTCAGGTTGACGCTTTTATTAACAGCGCTGCAAGCGTGAACTTTCGTGAGGAATTGGAT
AAAGCCCTGAAAATCAACACCTTGTGTCTTGAAAATGTTGCTGCTCTTGCAGAATTGAAC
TCCGCTATGGCGGTCATTCAGGTTTCCACTTGTTACGTTAACGGTAAAAACTCCGGTCAA
ATTACCGAATCCGTCATTAAACCTGCTGGCGAATCCATTCCCGTTCCACTGACGGTTAC
TACGAGATCGAAGAATTGGTCCATCTGTTGCAAGACAAGATTTCCGATGTTAAAGCTCGT
TACTCCGGCAAAGTTCTGGAGAAAAAATTGGTTGATTTGGGTATTCGTGAGGCCAATAAT
TACGGATGGTCCGACACCTACACATTCACCAAATGGTTGGGTGAACAACTGCTGATGAAG
GCCTTGTCTGGTCGTTCTTTGACTATTGTGCGTCCCTCTATTATTGAGTCCGCTTTGGAA
GAACCTTCCCCTGGTTGGATCGAAGGCGTTAAAGTTGCCGATGCCATTATCTTGGCTTAT
GCCCGTGAAAAAGTTAGCCTGTTCCCTGGAAAACGTTCCGGCATTATTGATGTTATTCCT
GTCGATTTGGTTGCGAACTCCATCATCTTGTCTCTGGCTGAGGCGTTGTCTGGTTCTGGT
CAACGTCGTATTTATCAATGTTGCAGCGGTGGTTCTAATCCAATCTCCCTGGGTAAGTTC
ATTGATTATTTGATGGCCGAGGCTAAGACCAACTATGCTGCCTACGATCAACTGTTTTAT
CGTCGTCCTACTAAACCTTTCGTCGCCGTGAACCGTAAATTGTTTGACGTTGTTGTTGGT
GGTATGCGTGTTCCTCTTTCTATTGCCGGTAAAGCTATGCGTTTGGCTGGTCAAAATCGT
GAGTTGAAAGTGCTTAAGAACCTTGATACGACCCGTTCCCTTGCAACCATTTTTGGCTTC
TATACTGCTCCCGACTATATCTTCCGTAACGATAGCTTGATGGCCCTGGCTTCTCGTATG
GGTGAATTGGATCGTGTTCTTTTCCCAGTTGATGCTCGTCAAATTGATTGGCAGTTGTAC
TTGTGTAAAATTCATTTGGGTGGTCTGAACCGTTACGCTTTGAAGGAACGTAAACTGTAT
TCTTTGCGTGCTGCTGATACTCGTAAAAAGCTGCCTAA

FIG. 3

Codon optimized *M. algicola* DG893 FAR DNA (SEQ ID NO: 3)

```
ATGGCCACCCAGCAGCAGCAGAACGGTGCATCCGCTTCGGGCGTTCTGGAGCAGCTTAGA
GGCAAGCATGTCTTGATTACCGGTACTACAGGATTTCTGGGAAAGGTGGTTCTGGAGAAG
CTGATCCGAACCGTGCCTGACATCGGTGGTATTCATCTGCTGATTAGAGGCAACAAGAGA
CATCCTGCTGCCAGAGAAGATTCTTGAACGAAATCGCCTCTTCCTCTGTGTTCGAGCGG
CTTAGACATGACGACAACGAAGCCTTTGAGACTTTCCTGGAGGAGCGTGTGCACTGCATC
ACCGGAGAAGTGACCGAGTCGAGATTTGGCCTTACTCCTGAGCGGTTCCGAGCCCTTGCT
GGCCAAGTGGATGCCTTCATCAATTCCGCCGCCTCTGTTAACTTCAGAGAGGAGCTGGAC
AAGGCACTCAAGATCAACACCCTGTGTCTGGAGAACGTGGCTGCTCTGGCCGAACTTAAC
TCCGCTATGGCAGTGATCCAAGTTTCCACCTGTTACGTGAACGGCAAGAACTCTGGACAG
ATCACCGAGTCCGTTATCAAGCCCGCTGGCGAATCCATCCCCAGATCCACAGATGGCTAC
TACGAGATCGAGGAGCTGGTCCACCTTCTGCAAGACAAGATCTCCGACGTGAAGGCTCGA
TACTCTGGCAAGGTGTTGGAGAAGAAGCTGGTGGACCTGGGCATCCGAGAGGCGAACAAC
TACGGCTGGTCTGACACCTACACCTTCACCAAATGGCTCGGAGAGCAGCTTCTGATGAAA
GCTCTGTCCGGAAGATCCCTGACTATCGTGCGGCCTTCCATCATCGAGTCGGCTCTTGAA
GAGCCTTCTCCAGGTTGGATCGAGGGCGTGAAGGTTGCTGACGCCATCATCCTTGCGTAC
GCCAGAGAGAAGGTTTCGTTGTTCCCCGGCAAGCGATCTGGCATCATCGACGTTATCCCC
GTGGATCTGGTGGCCAACTCTATCATTCTCTCTCTTGCTGAAGCCCTTTCTGGATCTGGC
CAGCGTAGAATCTACCAATGTTGTTCTGGCGGTTCTAACCCGATTTCTCTGGGCAAGTTC
ATCGACTACCTTATGGCCGAAGCCAAGACCAACTATGCTGCCTACGACCAGCTCTTCTAC
CGACGACCCACCAAGCCCTTCGTCGCTGTGAACCGAAAGCTGTTCGATGTTGTCGTGGGA
GGAATGCGAGTGCCTCTTTCCATTGCTGGCAAGGCCATGAGATTGGCGGGTCAGAATCGA
GAATTGAAGGTTCTCAAGAACCTTGACACTACTCGATCGCTCGCTACTATCTTTGGATTC
TACACTGCTCCTGACTACATCTTCCGGAATGACTCTCTGATGGCTCTTGCTTCCCGAATG
GGAGAACTCGATCGTGTGCTGTTCCCTGTTGACGCTCGACAGATCGACTGGCAGCTCTAC
TTGTGTAAGATCCACCTGGGCGGCCTGAACCGATATGCTCTGAAAGAACGAAAGCTGTAC
AGCCTTAGAGCCGCTGATACCCGAAAGAAGGCTGCT
```

FIG. 4

Codon optimized *Oceanobacter sp.* RED65 FAR DNA (SEQ ID NO: 5)

ATGTCTCAGTACTCCGCGTTCTCCGTTTCTCAATCTTTGAAGGGCAAACATATCTTCTTG
ACAGGTGTTACGGGTTTCTTGGGCAAGGCGATTCTGGAGAAACTGTTGTACTCCGTTCCA
CAATTGGCTCAGATTCATATCCTGGTCCGTGGTGGTAAAGTTAGCGCTAAGAAGCGTTTC
CAACATGACATCTTGGGTTCTTCCATCTTTGAGCGTCTTAAGGAACAACATGGCGAACAT
TTCGAAGAATGGGTTCAAAGCAAGATCAACCTTGTCGAGGGCGAACTTACTCAACCTATG
TTCGATTTGCCTTCTGCTGAGTTCGCTGGCTTGGCTAACCAATTGGATCTGATCATCAAT
AGCGCTGCTTCTGTCAACTTTCGTGAGAACTTGGAGAAGGCTCTGAACATCAATACCCTG
TGTCTGAACAACATCATTGCGCTGGCTCAGTACAACGTCGCTGCTCAAACTCCTGTTATG
CAAATCTCCACCTGCTATGTCAACGGCTTCAACAAAGGCCAAATCAACGAGGAAGTTGTT
GGTCCTGCTTCTGGTTTGATTCCTCAGTTGTCCCAAGACTGCTACGACATTGATTCCGTC
TTCAAGCGTGTTCATTCCCAGATTGAACAAGTCAAGAAACGTAAGACCGACATTGAACAG
CAAGAACAAGCCTTGATCAAACTGGGTATCAAGACCTCTCAACATTTCGGCTGGAATGAT
ACCTACACCTTCACCAAGTGGCTGGGTGAACAATTGTTGATTCAGAAGTTGGGCAAGCAA
TCTTTGACAATTCTTCGTCCGTCCATCATCGAATCTGCTGTTCGTGAACCTGCTCCTGGC
TGGGTTGAAGGCGTGAAAGTTGCGGATGCCTTGATCTATGCTTACGCTAAAGGTCGTGTT
AGCATCTTTCCCGGTCGTGATGAAGGTATCTTGGATGTCATCCCTGTTGATTTGGTTGCT
AATGCCGCCGCATTGTCCGCTGCTCAGCTTATGGAATCTAACCAGCAAACTGGCTATCGT
ATCTATCAATGCTGTTCTGGTTCCCGTAATCCGATCAAGCTGAAAGAGTTCATTCGTCAC
ATTCAGAATGTTGCTCAAGCCCGTTACCAAGAATGGCCAAAGTTGTTTGCTGACAAACCT
CAGGAAGCCTTCAAGACCGTGTCTCCTAAACGTTTCAAGCTGTACATGTCTGGTTTCACT
GCTATCACATGGGCTAAGACCATCATTGGTCGTGTCTTTGGATCTAATGCTGCCTCCCAA
CACATGTTGAAGGCTAAGACCACAGCATCTTTGGCGAACATCTTTGGTTTCTACACTGCT
CCTAACTACCGTTTCTCCTCTCAGAAGTTGGAACAGTTGGTCAAACAGTTCGATACTACC
GAACAACGTCTTTACGACATTCGTGCTGACCATTTCGATTGGAAGTACTACTTGCAGGAA
GTTCACATGGATGGTCTTCACAAGTATGCGTTGGCCGATCGTCAAGAATTGAAGCCCAAA
CATGTGAAGAAGCGTAAACGTGAAACGATTCGTCAAGCTGCTTAA

FIG. 5

Codon optimized *Oceanobacter sp.* RED65 FAR DNA (SEQ ID NO: 7)

```
ATGTCCCAGTACTCGGCTTTCTCTGTTTCTCAATCTCTGAAGGGCAAGCACATCTTTCTC
ACTGGTGTCACTGGCTTTCTCGGAAAGGCAATTCTGGAGAAGCTCTTGTACTCGGTTCCC
CAGCTGGCACAGATCCATATCCTTGTGAGAGGCGGCAAAGTTTCTGCCAAGAAGCGGTTT
CAGCACGACATCCTGGGCTCTAGCATCTTCGAGAGACTTAAGGAGCAACACGGAGAGCAC
TTTGAGGAATGGGTTCAGTCCAAGATCAACCTTGTGGAGGGAGAACTGACTCAACCAATG
TTTGACCTCCCTTCTGCTGAGTTCGCTGGACTTGCTAACCAGCTGGACCTGATCATCAAC
TCTGCCGCTTCGGTTAACTTTCGAGAGAACCTGGAGAAGGCTCTGAACATCAACACCCTG
TGCCTGAACAACATCATCGCTCTGGCTCAGTACAATGTCGCTGCCCAGACTCCTGTGATG
CAGATTTCCACCTGCTACGTGAACGGCTTCAACAAGGGCCAGATCAACGAAGAAGTTGTG
GGACCTGCTTCTGGACTGATCCCTCAGCTGTCTCAAGATTGCTACGACATCGACTCCGTC
TTCAAGAGAGTGCATTCCCAGATTGAGCAGGTGAAGAAGAGAAAGACAGACATTGAGCAG
CAGGAACAAGCCCTTATCAAGCTCGGTATCAAGACTTCCCAGCACTTTGGCTGGAATGAC
ACTTACACCTTCACCAAATGGCTCGGCGAACAGCTGTTGATTCAGAAGCTCGGCAAGCAA
TCTCTCACCATTCTTCGACCTTCGATCATTGAGTCTGCTGTGAGAGAGCCTGCGCCCGGA
TGGGTCGAAGGAGTGAAAGTCGCTGACGCCCTTATCTACGCTTATGCTAAGGGAAGAGTC
TCGATCTTTCCTGGAAGAGACGAGGGCATCCTTGATGTGATTCCCGTTGACCTTGTTGCC
AATGCTGCTGCTCTTTCTGCTGCACAACTCATGGAGTCCAACCAACAGACTGGCTACCGA
ATCTACCAATGCTGCTCTGGATCTCGAAACCCCATCAAGCTGAAGGAGTTCATCCGACAC
ATCCAGAACGTGGCTCAGGCCCGATACCAGGAATGGCCTAAGCTGTTTGCCGATAAGCCT
CAAGAGGCCTTCAAGACTGTCTCTCCCAAGAGATTCAAGCTGTACATGTCCGGCTTCACT
GCCATCACCTGGGCTAAGACCATCATTGGCCGAGTGTTCGGCTCTAACGCAGCCTCCCAG
CACATGCTGAAGGCAAAGACCACAGCTTCCCTGGCCAACATCTTCGGCTTCTACACTGCA
CCCAACTACCGGTTCTCTTCCCAGAAGTTGGAACAGCTGGTGAAGCAGTTCGACACTACC
GAGCAGCGACTGTACGACATTCGAGCTGACCACTTCGACTGGAAGTACTACCTGCAAGAG
GTTCACATGGATGGCCTTCACAAGTACGCTTTGGCCGATCGTCAGGAGCTGAAACCCAAG
CACGTGAAGAAGAGAAAGCGGGAGACTATCCGACAAGCTGCG
```

FIG. 6

FAR peptide (SEQ ID NOs: 2 and 4) from codon optimized (SEQ ID NOs: 1 and 3) DNA

```
MATQQQQNGASASGVLEQLRGKHVLITGTTGFLGKVVLEKLIRTVPDIGGIHLLIRGNKR
HPAARERFLNEIASSSVFERLRHDDNEAFETFLEERVHCITGEVTESRFGLTPERFRALA
GQVDAFINSAASVNFREELDKALKINTLCLENVAALAELNSAMAVIQVSTCYVNGKNSGQ
ITESVIKPAGESIPRSTDGYYEIEELVHLLQDKISDVKARYSGKVLEKKLVDLGIREANN
YGWSDTYTFTKWLGEQLLMKALSGRSLTIVRPSIIESALEEPSPGWIEGVKVADAIILAY
AREKVSLFPGKRSGIIDVIPVDLVANSIILSLAEALSGSGQRRIYQCCSGGSNPISLGKF
IDYLMAEAKTNYAAYDQLFYRRPTKPFVAVNRKLFDVVVGGMRVPLSIAGKAMRLAGQNR
ELKVLKNLDTTRSLATIFGFYTAPDYIFRNDSLMALASRMGELDRVLFPVDARQIDWQLY
LCKIHLGGLNRYALKERKLYSLRAADTRKKAA
```

FIG. 7

FAR peptide (SEQ ID NOs: 6 and 8) from codon optimized DNA (SEQ ID NOs: 5 and 7)

MSQYSAFSVSQSLKGKHIFLTGVTGFLGKAILEKLLYSVPQLAQIHILVRGGKVSAKKRF
QHDILGSSIFERLKEQHGEHFEEWVQSKINLVEGELTQPMFDLPSAEFAGLANQLDLIIN
SAASVNFRENLEKALNINTLCLNNIIALAQYNVAAQTPVMQISTCYVNGFNKGQINEEVV
GPASGLIPQLSQDCYDIDSVFKRVHSQIEQVKKRKTDIEQQEQALIKLGIKTSQHFGWND
TYTFTKWLGEQLLIQKLGKQSLTILRPSIIESAVREPAPGWVEGVKVADALIYAYAKGRV
SIFPGRDEGILDVIPVDLVANAAALSAAQLMESNQQTGYRIYQCCSGSRNPIKLKEFIRH
IQNVAQARYQEWPKLFADKPQEAFKTVSPKRFKLYMSGFTAITWAKTIIGRVFGSNAASQ
HMLKAKTTASLANIFGFYTAPNYRFSSQKLEQLVKQFDTTEQRLYDIRADHFDWKYYLQE
VHMDGLHKYALADRQELKPKHVKKRKRETIRQAA

FIG. 8

B. mori FAR DNA (SEQ ID NO: 9)

ATGTCCCACAATGGTACTCTTGATGAGCATTATCAGACAGTTCGTGAATTTTATGACGGT
AAGAGCGTTTTTATTACTGGCGCCACTGGCTTTCTTGGAAAAGCCTACGTTGAGAAACTG
GCATATTCTTGTCCCGGAATTGTCTCTATTTATATTTTGATTCGTGATAAAAGGGCTCC
AACACGGAGGAGCGTATGCGTAAATATTTGGACCAACCCATTTTCTCTCGTATTAAATAT
GAGCATCCAGAGTACTTCAAAAAGATTATCCCCATTTCTGGCGATATTACCGCCCCTAAA
CTTGGTCTTTGCGACGAGGAGCGTAACATCCTGATTAATGAAGTGTCCATCGTTATCCAC
TCTGCTGCCAGCGTTAAACTGAACGATCATCTTAAATTCACCTTGAACACCAACGTTGGT
GGTACTATGAAAGTCTTGGAGCTTGTTAAGGAGATGAAAAATTTGGCGATGTTTGTGTAC
GTTTCTACGGCTTATTCTAACACCAGCCAACGTATTTTGGAAGAAAAATTGTACCCTCAG
TCTCTGAATTTGAACGAAATTCAGAAATTCGCTGAAGAGCACTACATTCTGGGTAAGGAT
AACGACGAAATGATTAAATTCATTGGAAACCATCCTAACACTTACGCCTACACGAAAGCC
CTGGCTGAGAATCTTGTCGCTGAAGAACATGGAGAAATTCCTACTATTATTATTCGTCCT
TCTATCATCACAGCCTCCGCCGAGGAACCCGTTCGTGGATTTGTTGATTCTTGGAGCGGA
GCCACGGCTATGGCTGCATTTGCACTTAAAGGCTGGAACAACATCATGTATTCCACCGGT
GAAGAGAACATTGACTTGATCCCCCTGGATTACGTTGTCAACTTGACACTGGTGGCTATT
GCTAAATATAAGCCAACGAAAGAGGTTACGGTGTACCATGTTACAACGAGCGACTTGAAC
CCGATTAGCATCCGTCGTATTTTCATCAAACTGAGCGAGTTCGCCTCCAAAAACCCAACT
AGCAACGCTGCCCCATTCGCTGCCACTACATTGCTGACCAAACAGAAACCGCTTATTAAA
CTGGTGACATTTCTTATGCAGACCACACCAGCTTTTTTGGCAGACTTGTGGATGAAAACG
CAGCGTAAAGAGGCCAAGTTCGTGAAACAGCACAACTTGGTCGTTCGTTCTCGTGATCAG
CTGGAGTTCTTTACATCTCAGAGCTGGCTTTTGCGTTGTGAGCGTGCACGTGTCCTGTCC
GCGGCCTTGTCCGATTCCGACCGTGCTGTCTTCCGTTGCGATCCTTCCACGATTGATTGG
GATCAGTATCTTCCTATCTACTTCGAAGGTATTAATAAACACCTGTTCAAAAATAAGTTG
TAG

FIG. 9

*B. mori* FAR peptide (SEQ ID NO: 10)

MSHNGTLDEHYQTVREFYDGKSVFITGATGFLGKAYVEKLAYSCPGIVSIYILIRDKKGS
NTEERMRKYLDQPIFSRIKYEHPEYFKKIIPISGDITAPKLGLCDEERNILINEVSIVIH
SAASVKLNDHLKFTLNTNVGGTMKVLELVKEMKNLAMFVYVSTAYSNTSQRILEEKLYPQ
SLNLNEIQKFAEEHYILGKDNDEMIKFIGNHPNTYAYTKALAENLVAEEHGEIPTIIIRP
SIITASAEEPVRGFVDSWSGATAMAAFALKGWNNIMYSTGEENIDLIPLDYVVNLTLVAI
AKYKPTKEVTVYHVTTSDLNPISIRRIFIKLSEFASKNPTSNAAPFAATTLLTKQKPLIK
LVTFLMQTTPAFLADLWMKTQRKEAKFVKQHNLVVRSRDQLEFFTSQSWLLRCERARVLS
AALSDSDRAVFRCDPSTIDWDQYLPIYFEGINKHLFKNKL

FIG. 10

Codon optimized *B. mori* FAR DNA (SEQ ID NO: 11)

ATGTCTCACAACGGAACTCTTGACGAGCATTACCAAACTGTGCGAGAGTTCTACGACGGCAAATC
CGTGTTCATCACCGGAGCCACTGGATTTCTTGGTAAGGCATACGTGGAGAAGCTCGCTTACAGCT
GTCCCGGTATCGTTTCTATCTACATCCTGATTAGAGATAAGAAGGGCTCCAACACAGAAGAGCGG
ATGCGAAAGTACCTGGACCAGCCCATCTTCTCCCGGATCAAGTACGAACACCCTGAGTACTTCAA
GAAGATCATCCCCATTAGCGGAGACATTACTGCCCCAAAGCTGGGCTTGTGTGACGAGGAGCGGA
ACATCCTGATCAACGAGGTGTCCATCGTGATTCATTCCGCCGCCTCTGTTAAGCTGAACGACCAC
CTGAAGTTCACCCTGAACACTAACGTGGGTGGAACGATGAAGGTCCTGGAGCTGGTGAAGGAGAT
GAAGAACCTGGCCATGTTCGTGTACGTGTCCACCGCTTACTCCAACACCTCTCAGAGAATCCTGG
AGGAGAAGCTGTACCCTCAGTCCCTGAACCTGAACGAGATCCAGAAGTTCGCCGAGGAACACTAC
ATCCTGGGCAAGGACAACGACGAGATGATCAAGTTCATCGGCAACCACCCCAACACCTACGCTTA
CACCAAAGCCCTGGCTGAGAACCTTGTTGCCGAAGAGCATGGAGAGATCCCCACCATCATCATCC
GACCCTCTATCATTACTGCATCCGCGGAGGAGCCTGTGCGAGGCTTCGTCGATTCTTGGTCTGGC
GCTACTGCTATGGCTGCTTTCGCTCTCAAGGGATGGAACAACATCATGTATTCCACCGGCGAAGA
GAACATTGACCTGATCCCTCTCGACTACGTGGTGAACCTTACCCTGGTGGCCATCGCTAAGTACA
AGCCTACCAAAGAGGTGACCGTGTACCACGTCACGACTTCGGATCTGAATCCCATCTCCATCCGG
CGAATCTTCATCAAGCTGTCTGAGTTTGCTTCTAAGAACCCGACTTCTAATGCTGCTCCTTTCGC
TGCCACTACTCTGCTTACCAAGCAGAAACCCCTGATCAAGCTGGTTACGTTTCTGATGCAAACCA
CTCCTGCCTTCCTCGCTGACCTGTGGATGAAGACCCAGCGAAAGGAGGCCAAGTTCGTCAAACAG
CATAACCTCGTCGTTAGATCGCGAGATCAGTTGGAGTTCTTTACCTCCCAGTCCTGGCTGCTTCG
TTGTGAAAGAGCCAGAGTGCTGTCTGCTGCTCTTAGCGACTCTGATCGTGCCGTGTTTAGATGTG
ACCCCTCGACAATCGACTGGGATCAGTACCTGCCCATCTACTTCGAGGGCATCAACAAGCACCTG
TTCAAGAACAAGCTC

FIG. 11

Codon optimized *Marinobacter aquaeolei* FAR DNA (SEQ ID NO: 13)

ATGGCTATCCAGCAGGTTCATCACGCCGACACATCCTCCTCTAAAGTCCTGGGTCAACTT
CGTGGTAAACGTGTCTTGATTACCGGCACTACTGGATTCTTGGGTAAAGTCGTCTTGGAA
CGTTTGATTCGTGCCGTTCCTGACATCGGTGCTATCTACCTGCTGATTCGTGGTAACAAG
CGTCACCCGGATGCTCGTTCTCGTTTCTTGGAGGAGATTGCTACCTCCTCTGTCTTTGAT
CGTTTGCGTGAAGCTGATTCCGAAGGTTTCGATGCTTTCCTGGAAGAACGTATTCACTGT
GTTACTGGTGAAGTTACTGAAGCTGGTTTCGGTATTGGTCAAGAGGACTATCGTAAGTTG
GCCACCGAATTGGACGCAGTCATCAATTCTGCTGCCTCCGTCAACTTCCGTGAGGAGTTG
GATAAGGCTCTGGCCATCAACACTCTGTGTTTGCGTAACATCGCTGGTATGGTGGATCTT
AACCCTAAGCTGGCCGTTCTTCAAGTCTCTACGTGTTACGTCAACGGTATGAACTCTGGT
CAAGTTACTGAATCCGTCATCAAACCAGCTGGTGAAGCTGTTCCTCGTTCTCCTGATGGA
TTCTACGAGATCGAGGAATTGGTTCGTCTGCTGCAAGACAAGATTGAAGACGTTCAAGCA
CGTTACTCTGGTAAGGTGTTGGAGCGTAAGTTGGTTGATTTGGGTATTCGTGAGGCTAAT
CGTTACGGTTGGTCTGATACATACACCTTCACGAAATGGTTGGGTGAACAACTTCTGATG
AAAGCCTTGAATGGTCGTACCTTGACTATTCTGCGTCCTAGCATCATTGAATCTGCTTTG
GAAGAACCAGCACCTGGTTGGATTGAAGGCGTGAAAGTTGCAGATGCGATCATCTTGGCT
TATGCTCGTGAGAAGGTTACTTTGTTTCCGGGTAAACGTTCTGGTATCATTGATGTGATT
CCTGTTGACTTGGTTGCCAATTCCATCATCTTGTCTTTGGCTGAGGCTCTGGGCGAACCT
GGTCGTCGTCGTATCTACCAATGTTGTTCTGGTGGTGGTAATCCTATCTCCCTGGGCGAG
TTCATTGATCACCTGATGGCTGAATCCAAAGCCAACTATGCCGCATACGATCATCTGTTC
TACCGTCAACCCTCCAAGCCTTTCCTTGCTGTCAACCGTGCTTTGTTCGACTTGGTTATC
TCTGGTGTCCGTCTGCCTTTGTCTTTGACCGACCGTGTCTTGAAGCTGCTGGGCAACTCC
CGTGACCTGAAGATGCTGCGTAACCTGGATACTACGCAATCCCTGGCTACTATCTTTGGC
TTCTACACAGCCCCCGACTACATCTTCCGTAATGACGAGTTGATGGCCCTGGCTAACCGT
ATGGGCGAGGTTGATAAGGGTTTGTTCCCCGTTGATGCTCGTCTGATTGATTGGGAATTG
TACCTGCGTAAGATTCACCTGGCTGGTTTGAACCGTTACGCCTTGAAGGAGCGTAAGGTT
TACTCTTTGAAGACAGCCCGTCAGCGTAAGAAGGCAGCTTAA

FIG. 12

*Marinobacter aquaeolei* FAR peptide (SEQ ID NO: 14)

```
MAIQQVHHADTSSSKVLGQLRGKRVLITGTTGFLGKVVLERLIRAVPDIGAIYLLIRGNK
RHPDARSRFLEEIATSSVFDRLREADSEGFDAFLEERIHCVTGEVTEAGFGIGQEDYRKL
ATELDAVINSAASVNFREELDKALAINTLCLRNIAGMVDLNPKLAVLQVSTCYVNGMNSG
QVTESVIKPAGEAVPRSPDGFYEIEELVRLLQDKIEDVQARYSGKVLERKLVDLGIREAN
RYGWSDTYTFTKWLGEQLLMKALNGRTLTILRPSIIESALEEPAPGWIEGVKVADAIILA
YAREKVTLFPGKRSGIIDVIPVDLVANSIILSLAEALGEPGRRRIYQCCSGGGNPISLGE
FIDHLMAESKANYAAYDHLFYRQPSKPFLAVNRALFDLVISGVRLPLSLTDRVLKLLGNS
RDLKMLRNLDTTQSLATIFGFYTAPDYIFRNDELMALANRMGEVDKGLFPVDARLIDWEL
YLRKIHLAGLNRYALKERKVYSLKTARQRKKAA
```

US 8,216,815 B2

PRODUCTION OF FATTY ALCOHOLS WITH FATTY ALCOHOL FORMING ACYL-COA REDUCTASES (FAR)

CROSS REFERENCE TO RELATED APPLICATIONS

This application claims benefit of provisional application No. 61/221,934 filed Jun. 30, 2009 and provisional application No. 61/315,380 filed Mar. 18, 2010, the entire contents of which are incorporated herein by reference.

REFERENCE TO SEQUENCE LISTING

The "Sequence Listing" submitted electronically concurrently herewith pursuant to 37 C.F.R. §1.821 in a computer readable form (CRF) via file name CX3-017US-ST25.txt is incorporated herein by reference. The electronic copy of the Sequence Listing was created Jun. 28, 2010, and the size on disk is 82 Kbytes.

BACKGROUND

Diesel fuel is any fuel used in diesel engines and includes both petrodiesel and biodiesel. Petrodiesel is a specific fractional distillate of fossil fuel oil. It is comprised of about 75% saturated hydrocarbons and 25% aromatic hydrocarbons. Biodiesel is not derived from petroleum but from vegetable oil or animal fats and contains long chain alkyl esters. Biodiesel is made by the transesterification of lipids (e.g., spent vegetable oil from fryers or seed oils) with an alcohol and burns cleaner than petrodiesel. Biodiesel can be used alone or mixed with petrodiesel in any amount for use in modern engines.

Kerosene is a combustible hydrocarbon that is also a specific fractional distillate of fossil fuel and contains hydrocarbons having 6 to 16 carbon atoms. Kerosene has a heat of combustion comparable to that of petrodiesel and is widely used in jet fuel to power jet engines and for heating in certain countries. Kerosene-based fuels can also be burned with liquid oxygen and used as rocket fuel (e.g., RP-1).

Reliance on petroleum-derived fuels has depleted the supply of natural resources and has required increased reliance on imported gasoline and diesel products. In addition, the burning of petroleum-based fuels has increased the amount of greenhouse gasses (e.g., carbon dioxide and methane) in the atmosphere that is contributing to the gradual warming of the earth's climate.

Fuels, such as biodiesel, that are made from animal or vegetable products burn cleaner than petroleum-derived fuels and do not produce a net increase in greenhouse gases. Furthermore, they are a sustainable energy source and have the potential to reduce the United States' reliance on imported petroleum-based products. However, there is a concern that using land to produce fuel crops rather than food crops will contribute to world hunger.

Fatty acids are the principle component of cell membranes and are used by nearly all organisms as a primary source of energy storage. Fatty alcohols are the reduction products of fatty acids and, like fatty acids, can be produced enzymatically by cultured cells. Fatty alcohols can be reacted with acids to form ester compositions similar to those present in biodiesel fuel, or reduced to form kerosene-like compositions, or hydrocarbon compositions similar to petrodiesel. Enzymes that convert fatty acyl-thioester substrates (e.g., fatty acyl-CoA or fatty acyl-ACP) to fatty alcohols are commonly referred to as fatty alcohol forming acyl-CoA reductases or fatty acyl reductases ("FARs").

PCT Publication No. WO 2007/136762 discloses genetically engineered microorganisms for the production of fatty acid derivatives and methods of their use.

PCT Publication No. WO 2009/140695 discloses compositions comprising cyanobacterial genes encoding enzymes involved in hydrocarbon biosynthesis and methods of using then in the production of aldehydes and alcohols.

Steen et al., 2010, Nature 463:559-563 discloses the engineering of *E. coli* to produce specific fatty esters, fatty alcohols and waxes directly from simple sugars.

Schirmer, 2009, Current Opinion in Microbiology 12:274-281 describes the fermentative and nonfermentative metabolism of heterotrophic microorganisms used in the production of fuel-like molecules, biocatalysts that convert metabolic intermediates into fuel-like molecules, and the parameters that govern the cost effective production of such fuel-like molecules.

U.S. Pat. No. 5,370,996 and Metz et al. (2000) *Plant Physiology* 122:635-644 disclose isolation and characterization of a fatty acyl reductase (FAR) enzyme from the desert shrub *Simmondsia chinensis*, more commonly known as jojoba.

Moto et al. (2003) *Proc. Nat'l Acad. Sci. USA* 100(16): 9156-9161 discloses the isolation and characterization of a FAR enzyme from the silk moth *Bombyx mori*.

Reiser et al. (1997) *J. Bacteriol.* 179(9):2969-2975 discloses the isolation and characterization of a fatty acyl CoA reductase enzyme from the wax ester producing bacterium *Acinetobacter calcoaceticus* that reduces a fatty acyl-CoA substrate with chain lengths from C14 to C22 to the corresponding fatty aldehyde, requiring a dehydrogenase enzyme for conversion of the fatty aldehyde to the fatty alcohol.

In theory, these FAR enzymes could be expressed in heterologous hosts as a means of producing a non-petroleum-based, renewable source of fatty alcohols or derivative compositions for use in biofuels. However, when expressed in heterologous hosts such as *E. coli* and yeast, the yields of fatty alcohols obtained have been insufficient for certain applications. In addition, at most, only a small fraction of the produced fatty alcohols are secreted by the microorganisms, increasing substantially the cost of purification.

Accordingly, there remains a need in the art for enzymes such as FAR enzymes that can be used to efficiently produce fatty alcohols for use in industrial applications such as, but not limited to applications in the food industry, cosmetic industry, medical industry, and fuels industry.

SUMMARY

The present disclosure provides isolated fatty acyl reductase (FAR) enzymes, nucleic acids encoding the FAR enzymes, recombinant microorganisms engineered to express the FAR enzymes, methods of producing fatty alcohols and other compositions utilizing the FAR enzymes and/or recombinant microorganisms, and compositions comprising and/or that are derived from the fatty alcohols. The various inventions described herein are based, in part, on the inventors' surprising discovery that certain genera of the class of gammaproteobacteria found in seawater contain FAR enzymes that are capable of generating high yields of total and secreted fatty alcohols when expressed in heterologous cells.

In particular, the present inventors have discovered that *Marinobacter* species algicola (strain DG893) ("FAR_Maa"), *Marinobacter aquaeolei* VT8 ("FAR_Maq"), and *Oceanobacter* species strain RED65 (recently reclassified as

*Bermanella marisrubri* RED65) ("FAR_Ocs") possess FAR enzymes capable of producing approximately 150- to 400-times more total fatty alcohol, respectively, than FAR enzymes from *B. mori*, when expressed in an *E. coli* host. Significantly greater yields of fatty alcohols are also achieved in yeast. Based on this surprising discovery, it is expected that other genera of marine bacteria and particularly marine gammaproteobacteria will likewise contain FAR enzymes that are especially suitable for the production of fatty alcohols, especially when expressed in heterologous host microorganisms. In certain embodiments, FAR enzymes that are especially suitable for the production of fatty alcohols may be identified using Hidden Markov Models ("HMMs"), which identify proteins by similarity to patterns found in pre-complied sets of protein sequences. The patterns inherent in each pre-complied set are encapsulated in HMMs. It is the HMM for a given sequence set that defines a protein domain or protein family. Using this technique it is possible to classify portions of a given protein sequence that share common domains with previously-identified suitable FAR enzymes. See, e.g., the website pfam.sanger.ac.uk/. In certain embodiments, the HMMs are used to identify NAD binding domains and/or sterile domains.

Accordingly, in one aspect the present disclosure provides isolated FAR enzymes derived from or obtained from marine bacteria, such as marine gammaproteobacteria, and/or functional fragments thereof having FAR activity. In some embodiments, the FAR enzyme is isolated directly from the marine gammaproteobacteria in which it occurs naturally. In some embodiments, the FAR enzyme and/or a function fragment is isolated from a heterologous host microorganism engineered to express the FAR enzyme or functional fragment.

In another aspect, the present invention relates to a FAR enzyme and functional fragment thereof derived or obtained from *M. algicola* strain DG893. In one embodiment, the FAR enzyme or functional fragment thereof has an amino acid sequence that is at least 30% identical, at least 75% identical, at least 80% identical and at least 90% identical to SEQ ID NO: 2 or a functional fragment thereof. In another specific embodiment, the isolated FAR enzyme has an amino acid sequence that is identical to SEQ ID NO: 2.

In a further aspect, the present invention relates to a FAR enzyme and functional fragment thereof derived or obtained from a strain of *Oceanobacter*. In one specific embodiment, the FAR enzyme is obtained or derived from *Oceanobacter* strain RED65 and has an amino acid sequence that is at least 30% identical, at least 75% identical, at least 80% identical, and at least 90% identical to SEQ ID NO: 6. In another specific embodiment, the isolated FAR enzyme has an amino acid sequence that is identical to SEQ ID NO: 6.

In an additional aspect, the present disclosure provides polynucleotides encoding a marine gammaproteobacterial FAR enzyme, or functional fragment thereof, as described above. The polynucleotide can be a DNA or RNA, and can be single-stranded or double-stranded. It can be isolated from a naturally occurring microorganism, or prepared wholly or partially via synthetic means. In one embodiment, the nucleic acid sequence encodes a fatty acyl-CoA reductase (FAR) enzyme comprising an amino acid sequence having at least 30% sequence identity to SEQ ID NO: 2, SEQ ID NO: 6, SEQ ID NO: 14 or functional fragments thereof. In other embodiments, the nucleic acid encodes a FAR enzyme comprising at least 75% sequence identity (that is at least 75%, at least 80%, at least 90%, at least 95% and even 100% sequence identity) to SEQ ID NO: 2, SEQ ID NO: 6, SEQ ID NO: 14 or a functional fragment thereof. In some embodiments of this aspect, a vector comprises the nucleic acid encoding the FAR enzyme. In some embodiments, the polynucleotide encoding the FAR enzyme or functional fragment thereof is operably linked to a promoter, and optionally, to other control sequences and elements that control expression. In some embodiments, the vector is designed or selected so as to remain distinct from the genome of the host microorganism (for example, a plasmid) or to integrate into the genome of the host microorganism for example by either homologous recombination or site-specific integration. In a specific embodiment, the codons of the portion of the construct encoding the FAR enzyme or functional fragment are optimized for expression in a particular host microorganism.

In one more aspect, the present disclosure provides recombinant microorganisms engineered to express a heterologous marine gammaproteobacterial FAR gene, or a functional fragment thereof, as described herein. In some embodiments, recombinant host cells include bacteria, filamentous fungi and yeast. In particular embodiments, bacteria are *E. coli*. In other particular embodiments, the yeast is an oleaginous yeast. In certain embodiments, the oleaginous yeast is *Y. lipolytica*. In still other particular embodiments, the yeast is *S. cerevisiae*. In certain aspects, the microorganisms are wild-type microorganisms. In other aspects, the microorganisms are genetically modified.

In certain specific embodiments, the genetically modified microorganism further over expresses a gene encoding a protein that increases the rate at which the microorganism produces the substrate of a FAR enzyme, i.e., a fatty acyl-thioester substrate. In certain embodiments, the enzyme encoded by the over expressed gene is directly involved in fatty acid synthesis. In particular embodiments, the enzyme encoded by the over expressed gene is selected from a fatty acid synthase, an acyl-ACP thioesterase, a fatty acyl-CoA synthase and an acetyl-CoA carboxylase. In some embodiments, the protein encoded by the over expressed gene is endogenous to the microorganism. In other embodiments, the protein encoded by the over expressed gene is heterologous to the microorganism.

In yet another aspect, the present disclosure provides methods of producing compositions comprising fatty alcohols and/or acid esters and/or alkanes and/or alkenes derived from the fatty alcohols. In certain embodiments, the fatty alcohols are produced in a cell-free system where a FAR enzyme as described above is provided with a fatty acyl-thioester substrate and necessary cofactors under suitable conditions of temperature, pH and ionic strength for a time sufficient to produce fatty alcohols. In various embodiments, fatty alcohols are produced by a recombinant host cell comprising a heterologous gene encoding a FAR enzyme described above. In these embodiments, the host cell is cultured in an aqueous nutrient medium comprising an assimilable carbon source under conditions suitable for production of fatty alcohols. In certain specific embodiments, the recombinant host cell is a bacterium or yeast. In various embodiments, the yeast is an oleaginous yeast. In particular embodiments, the bacterium is *E. coli* and the yeast is selected from *S. cerevisiae* and *Y. lipolytica*.

In some embodiments, the fatty alcohols are produced by a recombinant host cell comprising a heterologous gene encoding a FAR enzyme and one or more proteins that increase the rate at which the recombinant host cell produces the acyl-thioester substrate for FAR. In some embodiments, the one or more proteins are directly involved in fatty acid biosynthesis. In certain particular embodiments, the one or more proteins are selected from a fatty acid synthase, an acyl-ACP thioesterase, a fatty acyl-CoA synthase and an acetyl-CoA carboxylase. In some aspects, the fatty alcohols produced by the recombinant microorganisms are secreted from the cells into the aqueous nutrient medium. In certain embodiments, the methods described herein include a step of isolating the fatty alcohols.

In an additional aspect, the invention relates to a method of producing a fatty alcohol composition comprising culturing a recombinant microorganism in a suitable culture medium wherein the recombinant microorganism comprises a gene encoding a heterologous fatty acyl reductase (FAR) enzyme having at least 30% sequence identity to SEQ ID NO: 2, SEQ ID NO: 6, SEQ ID NO: 14 or a functional fragment thereof and allowing expression of said gene wherein said expression results in the production of a composition of fatty alcohols. In some embodiments of this aspect, the method further comprises isolating the produced fatty alcohols. In particular embodiments, the methods described herein produce at least about 0.5 g/L of fatty alcohols, also at least 5 g/L and even at least 15 g/L of fatty alcohols.

In yet another aspect, the invention relates to a method of producing a fatty alcohol composition by an acyl-CoA independent pathway comprising culturing a recombinant E. coli in a nutrient medium under suitable conditions, wherein said recombinant E. coli comprises a nucleic acid sequence encoding a heterologous fatty acyl-CoA reductase (FAR) enzyme comprising an amino acid sequence having at least 75% (such as at least 75%, at least 80%, at least 85%, at least 90%, at least 95%, at least 97% and even 100%) sequence identity to SEQ ID NO: 2, SEQ ID NO: 6, SEQ ID NO: 14 or functional fragments thereof; allowing expression of said FAR; and producing a fatty alcohol composition.

In yet a further aspect, the recombinant microorganism engineered to express a FAR encompassed by the invention is a bacterium and particularly an E. coli comprising an inactivated or silenced endogenous fatty acyl-CoA synthetase fadD gene. In other embodiments, the recombinant E. coli will comprise an inactivated or silenced endogenous short chain fatty acyl-CoA synthetase fadK gene. In still other embodiments, both genes will be inactivated or silenced.

In yet another aspect, the present disclosure provides for fatty alcohol compositions produced by a method described above. In some embodiments, the fatty alcohol composition is produced in a cell-free system. In other embodiments, the fatty alcohol composition is produced by a recombinant host cell. In particular embodiments, the compositions comprise fatty alcohols with saturated, unsaturated, linear, branched or cyclic hydrocarbon chains. In certain embodiments, the compositions comprise saturated fatty alcohols and/or monounsaturated fatty alcohols.

In still other aspects, the present disclosure provides for compositions comprising alkanes and/or alkenes derived by reducing the fatty alcohol compositions described herein. In certain embodiments, the reduction reaction is carried out chemically. In other embodiments, the reduction reaction is carried out using a microorganism that has a biosynthetic pathway for reducing fatty alcohols. In certain embodiments, the compositions produced by reduction of fatty alcohols comprise substantially all alkanes and/or alkenes. In other embodiments, the compositions comprise a mixture of fatty alcohols and alkanes and/or alkenes derived there from.

In yet another aspect, the present disclosure provides for fuel compositions comprising fatty alcohols and/or acid esters and/or alkanes and/or alkenes derived there from. In certain embodiments, the fatty alcohol compositions produced by the methods described above are used directly in fuel compositions. In various embodiments, the fatty alcohols are reacted with a carboxylic acid to produce acid esters for use as biodiesel fuel compositions. In other embodiments, the fatty alcohols are reacted with a reducing agent to produce alkanes and/or alkenes. In certain embodiments, the fatty alcohols undergo esterification to form fatty esters. In some embodiments, the alkanes and/or alkenes derived from the fatty alcohol compositions are used as components of jet fuel compositions. In other embodiments, the alkanes and/or alkenes derived are used as components of rocket fuel. In still other embodiments, alkanes and/or alkenes derived from the fatty alcohol compositions are used as components of petrodiesel-like fuel compositions.

BRIEF DESCRIPTION OF THE FIGURES

FIG. 2 shows a codon optimized polynucleotide sequence (SEQ ID NO: 1) encoding a FAR enzyme of *Marinobacter algicola* strain DG893 having the amino acid sequence shown in FIG. 6 (SEQ ID NO: 2).

FIG. 3 shows a codon optimized polynucleotide sequence (SEQ ID NO: 3) encoding a FAR enzyme of *Marinobacter algicola* strain DG893 having the amino acid sequence shown in FIG. 6 (SEQ ID NO: 4) and optimized for expression in *Y. lipolytica*.

FIG. 4 shows a codon optimized polynucleotide sequence (SEQ ID NO: 5) encoding a FAR enzyme of *Oceanobacter* sp. strain RED65 having the amino acid sequence shown in FIG. 7 (SEQ ID NO: 6).

FIG. 5 shows a codon optimized polynucleotide sequence (SEQ ID NO: 7) encoding a FAR enzyme of *Oceanobacter* sp. strain RED65 having the amino acid sequence shown in FIG. 7 (SEQ ID NO: 8) and optimized for expression in *Y. lipolytica*.

FIG. 6 shows the amino acid sequence of a FAR polypeptide of *Marinobacter algicola* strain DG893. The amino acid sequence (SEQ ID NO: 2) encoded by the polynucleotide sequence of SEQ ID NO: 1 is identical to the amino acid sequence (SEQ ID NO: 4) encoded by the polynucleotide sequence of SEQ ID NO: 3. While it is understood that both SEQ ID NO: 2 and SEQ ID NO: 4 are identical and interchangeable, reference will generally be made to SEQ ID NO: 2 in this disclosure.

FIG. 7 shows the amino acid sequence of a FAR polypeptide of *Oceanobacter* sp. strain RED65. The amino acid sequence (SEQ ID NO: 6) encoded by the polynucleotide sequence of SEQ ID NO: 5 is identical to the amino acid sequence (SEQ ID NO: 8) encoded by the polynucleotide sequence of SEQ ID NO: 7. While it is understood that both SEQ ID NO: 6 and SEQ ID NO: 8 are identical and interchangeable reference will generally be made to SEQ ID NO: 6 in this disclosure. The amino acid sequence of SEQ ID NO: 2 and the amino acid sequence of SEQ ID NO: 6 are about 47% identical.

FIG. 8 shows a codon optimized polynucleotide sequence (SEQ ID NO: 9) encoding a FAR polypeptide (SEQ ID NO: 10) from the silk moth *B. mori*.

FIG. 9 shows the amino acid sequence (SEQ ID NO: 10 and SEQ ID NO: 12) of a FAR polypeptide from the silk moth *B. mori*.

FIG. 10 shows a codon optimized polynucleotide sequence (SEQ ID NO: 11) encoding a FAR enzyme of *B. mori* having the amino acid sequence shown in SEQ ID NO: 12 and optimized for expression in *Y. lipolytica*.

FIG. 11 shows a codon optimized polynucleotide sequence (SEQ ID NO: 13) encoding a FAR enzyme of *Marinobacter aquaeolei* having the amino acid sequence shown in SEQ ID NO: 14.

FIG. 12 shows the amino acid sequence of a FAR polypeptide of *Marinobacter aquaeolei* (SEQ ID NO: 14). The amino acid sequence of *M. aquaeolei* (SEQ ID NO: 14) has about 78% sequence identity to the amino acid sequence of *M. algicola* DG893 (SEQ ID NO: 2).

DETAILED DESCRIPTION

Figure 1:
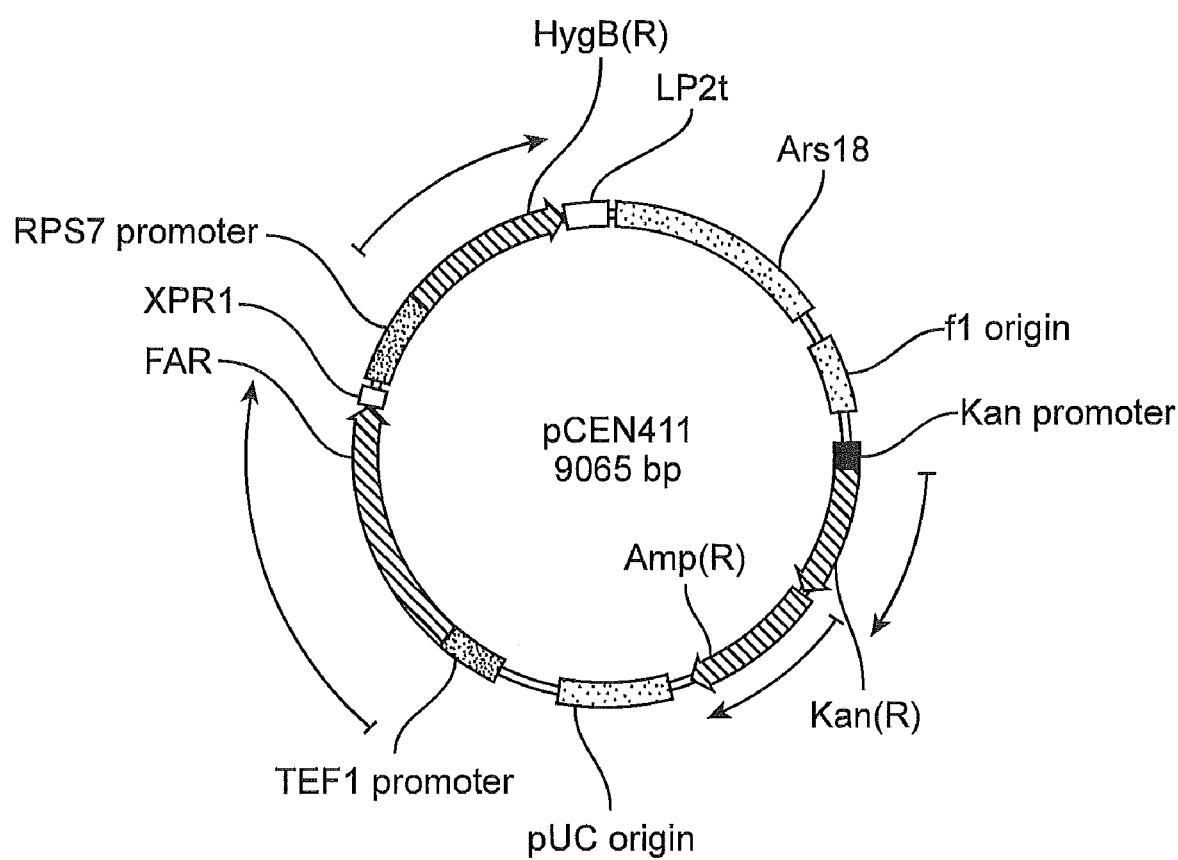
FIG. 1 shows the replicative *Y. lipolytica* vector pCEN411 (approximately 9065 bp) containing cassettes encoding hygromycin (HygB) resistance and FAR expression. Ars18 is an autonomous replicating sequence isolated from *Y. lipolytica* chromosomal DNA.

The present disclosure provides FAR enzymes, recombinant host cells comprising a nucleic acid encoding a heterologous FAR enzyme, processes for the biosynthesis of fatty alcohols including the conversion of fatty acyl-thioester complexes (such as fatty acyl-CoA substrates and fatty acyl-ACP substrates) to fatty alcohols, and compositions comprising fatty alcohols produced by the biosynthetic methods.

DEFINITIONS

Unless defined otherwise, all technical and scientific terms used herein generally have the same meaning as commonly understood by one of ordinary skill in the art to which this invention pertains. Generally, the nomenclature used herein and the laboratory procedures of cell culture, molecular genetics, organic chemistry, analytical chemistry and nucleic acid chemistry described below are those well known and commonly employed in the art.

As used herein, the following terms are intended to have the following meanings: The following abbreviations are used herein: "FAR" denotes fatty acyl reductase or fatty alcohol forming acyl-CoA reductase; "ACP" denotes acyl carrier protein; "CoA" denotes coenzyme A; "TE" denotes thioesterase; "FAS" denotes fatty acid synthase; "FACR" denotes fatty acyl-CoA reductase; "FACS" denotes fatty acyl-CoA synthase (synthetase) and acyl-CoA synthase (synthetase) as used interchangeably herein; and "ACC" denotes acetyl-CoA carboxylase.

"Fatty alcohol forming acyl-CoA reductase" or "fatty acyl reductase" as used interchangeably herein refers to an enzyme that catalyzes the reduction of a fatty acyl-CoA, a fatty acyl-ACP, or other fatty acyl thioester complex to a fatty alcohol, which is linked to the oxidation of NAD(P)H to NAD(P)$^+$, as shown in Scheme I:

Scheme I

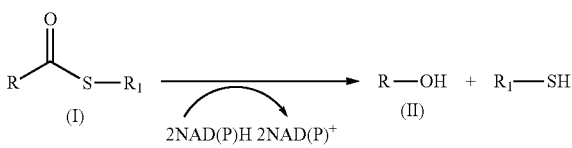

wherein "R" represents a C8 to C24 saturated, unsaturated, linear, branched or cyclic hydrocarbon, and "R$_1$" represents CoA, ACP or other fatty acyl thioester substrates. CoA is a non-protein acyl carrier group factor (or moiety) involved in the synthesis and oxidation of fatty acids. "ACP" is a polypeptide or protein subunit of fatty acid synthase used in the synthesis of fatty acids. FARs are distinct from FACRs. FACRs reduce only fatty acyl-CoA intermediates to fatty aldehydes and require an additional oxidoreductase enzyme to generate the corresponding fatty alcohol. "Fatty aldehyde" as used herein refers to a saturated or unsaturated aliphatic aldehyde and reference is made to FIG. 13, wherein R is as defined above.

The term "fatty acid" as used herein refers to a compound of formula III:

wherein "R" is as defined above. Saturated or unsaturated fatty acids can be described as "Ca:b", wherein "a" is an integer that represents the total number of carbon atoms and "b" is an integer that refers to the number of double bonds in the carbon chain.

The term "fatty alcohol" as used herein refers to an aliphatic alcohol of the formula (II) wherein R is as defined above. Saturated or unsaturated fatty alcohols can be described as "Ca:b-OH", wherein "a" is an integer that represents the total number of carbon atoms in the fatty alcohol and "b" is an integer that refers to the number of double bonds in carbon chain.

Unsaturated fatty acids or fatty alcohols can be referred to as "cis $\Delta^x$" or "trans $\Delta^x$" wherein "cis" and "trans" refer to the carbon chain configuration around the double bond and "x" indicates the number of the first carbon of the double bond, wherein carbon 1 is the carboxylic acid carbon of the fatty acid or the carbon bound to the —OH group of the fatty alcohol.

The term "fatty acyl-thioester" or "fatty acyl-thioester complex" refers to a compound of formula (I), wherein a fatty acyl moiety is covalently linked via a thioester linkage to a carrier moiety. Fatty acyl-thioesters are substrates for the FAR enzymes described herein.

The term "fatty acyl-CoA" refers to a compound of formula (I) wherein R$_1$ is Coenzyme A.

The term "fatty acyl-ACP" refers to a compound of formula (I) wherein R$_1$ is acyl carrier protein.

The phrase "acyl-CoA independent pathway" refers to the production of fatty alcohols by the direct enzymatic conversion of fatty acyl-ACP substrates to fatty alcohols and does not involve the use of free fatty acids or fatty acyl-CoA intermediates. This biosynthetic pathway differs from a) the fatty acyl-CoA dependent pathway which converts fatty acyl-ACP directly to fatty acyl CoA via an acyl-transfer reaction, such as in yeast, and b) the fatty acyl-CoA dependent pathway which converts fatty acyl-ACP to fatty acyl-CoA via a free fatty acid intermediate, such as in bacteria and reference is made to FIG. 13.

The acyl-CoA independent pathway has the advantage of bypassing the step of form a fatty acyl-CoA substrate from free fatty acid, which requires the use of ATP. Therefore, the acyl-CoA independent pathway may use less energy than the acyl-CoA dependent pathway that utilizes a free fatty acid intermediate.

"Conversion" refers to the enzymatic conversion of the substrate to the corresponding product. "Percent conversion"

refers to the percent of the substrate that is reduced to the product within a period of time under specified conditions. Thus, the "enzymatic activity" or "activity" of a polypeptide can be expressed as "percent conversion" of the substrate to the product.

"Percentage of sequence identity," "percent identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which may also contain gaps to optimize the alignment) for alignment of the two sequences. The percentage may be calculated by determining the number of positions at which the identical nucleic acid base or amino acid residue occurs in both sequences to yield the number of matched positions, dividing the number of matched positions by the total number of positions in the window of comparison (including positions where one of the sequences has a gap) and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences and that different methods may give slightly different results.

Alignment of sequences for comparison can be conducted, e.g., by the local homology algorithm of Smith and Waterman, 1981, Adv. Appl. Math. 2:482, by the homology alignment algorithm of Needleman and Wunsch, 1970, J. Mol. Biol. 48:443, by the search for similarity method of Pearson and Lipman, 1988, Proc. Natl. Acad. Sci. USA 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). The Clustral (Chema R., Sugawara H., Koike T., Lopez R., Gibson T. J., Higgins D. G., Thompson J. D., (2003) Multiple sequence alignment with the Clustral series of programs, Nucleic Acids Res., 31, 3497-3500.) and T-Coffee (T-COFFEE: A novel method for multiple sequence alignments. Notredame, Higgins, Heringa, J M B 302 (205-217) 2000 software packages may also be used to align sequences.

Examples of algorithms that are suitable for determining percent sequence identity and sequence similarity are the BLAST and BLAST 2.0 algorithms, which are described in Altschul et al., 1990, J. Mol. Biol. 215: 403-410 and Altschul et al., 1977, Nucleic Acids Res. 3389-3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, Proc Natl Acad Sci USA 89:10915). Exemplary determination of sequence alignment and % sequence identity can employ the BESTFIT or GAP programs in the GCG Wisconsin Software package (Accelrys, Madison Wis.), using default parameters provided.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a "comparison window" to identify and compare local regions of sequence similarity.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Conservative" amino acid substitutions or mutations refer to the interchangeability of residues having similar side chains, and thus typically involves substitution of the amino acid in the polypeptide with amino acids within the same or similar defined class of amino acids. However, as used herein, conservative mutations do not include substitutions from a hydrophilic to hydrophilic, hydrophobic to hydrophobic, hydroxyl-containing to hydroxyl-containing, or small to small residue, if the conservative mutation can instead be a substitution from an aliphatic to an aliphatic, non-polar to non-polar, polar to polar, acidic to acidic, basic to basic, aromatic to aromatic, or constrained to constrained residue.

Further, as used herein, A, V, L, or I can be conservatively mutated to either another aliphatic residue or to another non-polar residue. Table 1 below shows exemplary conservative substitutions.

TABLE 1

Conservative Substitutions

| Residue | Possible Conservative Mutations |
|---|---|
| A, L, V, I | Other aliphatic (A, L, V, I) |
|  | Other non-polar (A, L, V, I, G, M) |
| G, M | Other non-polar (A, L, V, I, G, M) |
| D, E | Other acidic (D, E) |
| K, R | Other basic (K, R) |
| P, H | Other constrained (P, H) |
| N, Q, S, T | Other polar (N, Q, S, T) |
| Y, W, F | Other aromatic (Y, W, F) |
| C | None |

"Non-conservative substitution" refers to substitution or mutation of an amino acid in the polypeptide with an amino acid with significantly differing side chain properties. Non-conservative substitutions may use amino acids between, rather than within, the defined groups listed above. In one embodiment, a non-conservative mutation affects (a) the structure of the peptide backbone in the area of the substitution (e.g., proline for glycine) (b) the charge or hydrophobicity, or (c) the bulk of the side chain.

"Deletion" refers to modification to the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the reference enzyme while retaining enzymatic activity and/or retaining the improved properties of an engineered enzyme. Deletions can be directed to the internal portions and/or terminal portions of the polypeptide. In various embodiments, the deletion can comprise a continuous segment or can be discontinuous. The term "deletion" is also used to refer to a DNA modification in which one or more nucleotides or nucleotide base-pairs have been removed, as compared to the corresponding reference, parental or "wild type" DNA.

"Insertion" refers to modification to the polypeptide by addition of one or more amino acids to the reference polypeptide. In some embodiments, the modification comprises insertions of one or more amino acids to the naturally occurring polypeptide as well as insertions of one or more amino acids to other modified polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide. The term "insertion" is also used to refer to a DNA modification in which or more nucleotides or nucleotide base-pairs have been inserted, as compared to the corresponding reference, parental or "wild type" DNA.

"Different from" or "differs from" with respect to a designated reference sequence refers to difference of a given amino acid or polynucleotide sequence when aligned to the reference sequence. Generally, the differences can be determined when the two sequences are optimally aligned. Differences include insertions, deletions, or substitutions of amino acid residues in comparison to the reference sequence.

As used herein in the context of a polypeptide or polynucleotide, the phrase "derived from" a particular organism refers to a wild-type polynucleotide or polypeptide that originates in the organism and to mutant and variants thereof that either originate in the organism or are produced by human manipulation of the wild-type polynucleotide or polypeptide.

"Functional fragment" as used herein refers to a polypeptide that has an amino-terminal and/or carboxy-terminal deletion, but where the remaining amino acid sequence is identical to the corresponding positions in the sequence and that retains substantially all of the activity of the full-length polypeptide. Functional fragments can comprise up to 60%, 65%, 70%, 75%, 80%, 85%, 90%, 95%, 96%, 97%, 98%, and 99% of the full-length polypeptide.

"Endogenous" polynucleotide, gene, promoter or polypeptide refers to any polynucleotide, gene, promoter or polypeptide that originates in a particular host cell. A polynucleotide, gene, promoter or polypeptide is not endogenous to a host cell if it has been removed from the host cell, subjected to laboratory manipulation, and then reintroduced into a host cell.

"Heterologous" polynucleotide, gene, promoter or polypeptide refers to any polynucleotide, gene, promoter or polypeptide that is introduced into a host cell that is not normally present in that cell, and includes any polynucleotide, gene, promoter or polypeptide that is removed from the host cell and then reintroduced into the host cell.

"Inactive" or "inactivated" in reference to a gene refers to a gene having at least one function that is impaired. Genes can be inactivated in a variety of ways known in the art, including but not limited to insertion of a mobile genetic element (e.g., a transposon); deletion of all or part of the gene, such that the gene product is not made, or is truncated and is non-functional; mutation of the gene such that the gene product is not made, or is truncated and is non-functional; deletion or mutation of one or more control elements that control expression of the gene such that the gene product is not made; and the like. In certain embodiments genes can be inactivated by methods other than genetic modification, for example, by gene silencing at the transcriptional level or at the post-transcriptional level using for example RNAi.

"Recombinant host cell" refers to a cell into which has been introduced a heterologous polynucleotide, gene, promoter, e.g., an expression vector, or to a cell having a heterologous polynucleotide or gene integrated into the genome.

"Naturally-occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation. A wild-type organism refers to an organism that has not been intentionally modified by human manipulation.

"Codon optimized" refers to changes in the codons of the polynucleotide encoding a protein to those preferentially used in a particular organism such that the encoded protein is efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding enzymes may be codon optimized for optimal production from the host organism selected for expression.

"Preferred, optimal, high codon usage bias codons" refers interchangeably to codons that are used at higher frequency in the protein coding regions than other codons that code for the same amino acid. The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. A variety of methods are known for determining the codon frequency (e.g., codon usage, relative synonymous codon usage) and codon preference in specific organisms, including multivariate analysis, for example, using cluster analysis or correspondence analysis, and the effective number of codons used in a gene (See GCG Codon Preference, Genetics Computer Group Wisconsin Package; CodonW, John Peden, University of Nottingham; McInerney, J. O, 1998, Bioinformatics 14:372-73; Stenico et al., 1994, Nucleic Acids Res. 222437-46; Wright, F., 1990, Gene 87:23-29). Codon usage tables are available for a growing list of organisms (see for example, Wada et al., 1992, Nucleic Acids Res. 20:2111-2118; Nakamura et al., 2000, Nucl. Acids Res. 28:292; Duret, et al., supra; Henaut and Danchin, "*Escherichia coli* and *Salmonella,*" 1996, Neidhardt, et al. Eds., ASM Press, Washington D.C., p. 2047-2066), all of which are incorporated herein by reference. The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTs), or predicted coding regions of genomic sequences (see for example, Mount, D., Bioinformatics: Sequence and Genome Analysis, Chapter 8, Cold Spring Harbor Laboratory Press, Cold Spring Harbor, N.Y., 2001; Uberbacher, E. C., 1996, Methods Enzymol. 266:259-281; Tiwari et al., 1997, Comput. Appl. Biosci. 13:263-270), all of which are incorporated herein by reference.

"Expression" as used herein may include any step involved in the production of the FAR polypeptides including but not limited to transcription and translation.

"Control sequence" is defined herein to include all components, which are necessary or advantageous for the expression of a polypeptide of the present disclosure. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

"Operably linked" and "operably associated" are defined herein as a configuration in which a control sequence is appropriately placed at a position relative to the coding sequence of the DNA sequence such that the control sequence directs the expression of a polynucleotide and/or polypeptide.

"Promoter sequence" is a nucleic acid sequence that is recognized by a host cell for expression of the coding region. The control sequence may comprise an appropriate promoter sequence. The promoter sequence contains transcriptional control sequences, which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either endogenous or heterologous to the host cell.

As used herein the term "transformed" or "transformation" used in reference to a cell means a cell has a non-native nucleic acid sequence integrated into its genome or as a plasmid that is maintained through multiple generations.

It should be noted that the indefinite articles "a" and "an" and the definite article "the" are used in the present application to mean one or more unless the context clearly dictates otherwise. Further, the term "or" is used in the present application to mean the disjunctive "or" and the conjunctive "and".

FAR Enzymes Useful in the Methods of the Disclosure:

In one aspect the present disclosure provides FAR enzymes derived from or obtained from gammaproteobacteria (such as marine gammaproteobacteria) and/or functional fragments thereof having FAR activity. In some embodiments, the FAR enzyme is isolated directly from the gammaproteobacteria in which it occurs naturally. In some embodiments, the FAR enzyme and/or a function fragment is isolated from a heterologous host microorganism engineered to express the FAR enzyme or functional fragment. The FAR enzyme and/or functional fragment can be derived or obtained from virtually any genus of marine gammaproteobacteria. In certain embodiments, the FAR enzyme for use in the methods disclosed herein is endogenous to a marine bacterium, i.e., a bacterium mined from a marine environment. In various embodiments, the FAR enzyme for use in the methods disclosed herein is endogenous to an organism other than a marine bacterium.

In certain embodiments, the FAR enzyme and/or functional fragment can be derived or obtained from a gammaproteobacterium of the order Alteromonadales. In some embodiments, the FAR enzyme and/or functional fragment can be derived from or obtained from the Alteromonadales family Alteromonadaceae. In certain embodiments, the FAR enzyme and/or functional fragment can be derived from or obtained from an Alteromonadaceae genus such as but not limited to the Alteromonadaceae genus *Marinobacter*. In certain specific embodiments, the FAR enzyme and/or functional fragment can be derived from the *Marinobacter* species algicola. In a particular embodiment, the FAR enzyme and/or functional fragment can be derived from or obtained from the *M. algicola* species strain DG893. In some specific embodiments, the FAR enzyme for use in the methods disclosed herein is from the marine bacterium *Marinobacter algicola* (e.g., *M. algicola*) DG893 (SEQ ID NO: 2) ("FAR_Maa").

In some embodiments, the FAR enzyme and/or functional fragment is derived or obtained from a species of *Marinobacter* including, but not limited to, a species selected from *M. algicola, M. alkaliphilus, M. aquaeolei, M. arcticus, M. bryozoorum, M. daepoensis, M. excellens, M. flavimaris, M. guadonensis, M. hydrocarbonoclasticus, M. koreenis, M. lipolyticus, M. litoralis, M. lutaoensis, M. maritimus, M. sediminum, M. squalenivirans* and *M. vinifirmus* and equivalent and synonymous species thereof.

In one specific embodiment, the FAR enzyme is derived or obtained from *M. algicola* strain DG893 and has an amino acid sequence that is at least 30% identical, at least 50% identical, at least 60% identical, at least 70% identical, at least 75%, at least 80% identical, at least 85% identical, at least 90% identical, at least 93% identical at least 95% identical, at least 97% identical and/or at least 98% identical to SEQ ID NO: 2 or a functional fragment thereof. In another specific embodiment, the isolated FAR enzyme has an amino acid sequence that is identical to SEQ ID NO: 2.

In one specific embodiment, the FAR enzyme is derived or obtained from *Marinobacter aquaeolei* and has an amino acid sequence that is at least 30% identical, at least 50% identical, at least 60% identical, at least 70% identical, at least 75%, at least 80% identical, at least 85% identical, at least 90% identical, at least 93% identical, at least 95% identical, at least 97% identical and/or at least 98% identical to SEQ ID NO: 14 or a functional fragment thereof. In another specific embodiment, the isolated FAR enzyme has an amino acid sequence that is identical to SEQ ID NO: 14.

In various embodiments, the isolated FAR enzyme and/or functional fragment is obtained or derived from a marine bacterium selected from the group of *Meptuniibacter caesariensis* species strain MED92, *Reinekea* sp. strain MED297, *Marinomonas* sp. strain MED121, unnamed gammaproteobacterium strain HTCC2207 and *Marinobacter* sp. strain ELB17 and equivalents and synonymous species thereof.

In various embodiments, the FAR enzyme and/or functional fragment can be derived or obtained from a gammaproteobacterium of the order Oceanospirillilales. In some embodiments, the FAR enzyme and/or functional fragment can be derived from or obtained from the Oceanospirillilales family Oceanospirillaceae. In certain embodiments, the FAR enzyme and/or functional fragment can be derived from or obtained from a Oceanospirillaceae genus, such as but not limited to *Oceanobacter*. In a particular embodiment, the FAR enzyme and/or functional fragment can be derived from or obtained from the *Oceanobacter* species strain RED65 and has an amino acid sequence that is at least 30% identical, at least 50% identical, at least 60% identical, at least 70% identical, at least 75% identical, at least 80% identical, at least 85% identical, at least 90% identical, at least 93% identical, at least 95% identical, at least 97% identical and/or at least 98% identical to SEQ ID NO: 6 or a functional fragment thereof. In another specific embodiment, the FAR enzyme for use in the methods disclosed herein comprises or consists of a sequence having 100% identity to the sequence of SED ID NO: 6 ("FAR_Ocs"). In other specific embodiments, the isolated FAR enzyme or functional fragment is obtained or derived from *Oceanobacter kriegii*. In still other specific embodiments, the isolated FAR enzyme or functional fragment is obtained or derived from *Oceanobacter* strain WH099.

In various embodiments, the FAR enzyme is from a marine bacterium and is selected from the group consisting of FAR_Hch (*Hahella chejuensis* KCTC 2396 GenBank YP_436183.1); FAR_Mac (from marine *actinobacterium* strain PHSC20C1), FAR_JVC (JCVI_ORF_1096697648832, GenBank Accession No. EDD40059.1; from a marine metagenome), FAR_Fer (JCVI_SCAF_1101670217388; from a marine bacterium found at a depth of 12 m in an upwelling in the area of Fernandina Island, the Galapagos Islands, Ecuador), FAR_Key (JCVI_SCAF_1097205236585, from a marine bacterium found at a depth of 1.7 m off the coast of Key West Fla.), and FAR_Gal (JCVI_SCAF_1101670289386, at a depth of 0.1 m at Isabella Island, Galapagos Islands, Ecuador). Approximate sequence identity to *M. algicola* DG893 (FAR_Maa) and *Oceanobacter* sp. RED65 (FAR_Ocs) is given in the table below.

| FAR Gene | % Sequence Identity to FAR_Maa (SEQ ID NO: 2/4) | % Sequence Identity to FAR_Ocs (SEQ ID NO: 6/8) |
| --- | --- | --- |
| FAR_Maa | 100 | 46 |
| FAR_Mac | 32 | 31 |
| FAR_Fer | 61 | 36 |
| FAR_Gal | 25 | 25 |
| FAR_JVC | 34 | 30 |
| FAR_Key | 32 | 30 |
| FAR_Maq | 78 | 45 |
| FAR_Hch | 54 | 47 |

In one particular embodiment, the FAR enzyme is isolated or derived from the marine bacterium FAR_Gal. In other embodiments, the FAR enzyme or functional fragment is isolated or derived from an organism selected from the group consisting of *Vitis vinifera* (GenBank Accession No. CAO22305.1 or CAO67776.1), *Desulfatibacillum alkenivorans* (GenBank Accession No. NZ_ABII01000018.1), *Stigmatella aurantiaca* (NZ_AAMD01000005.1) and *Phytophthora ramorum* (GenBank Accession No.: AAQX01001105.1).

In certain embodiments, a FAR enzyme or functional fragment thereof that is especially suitable for the production of fatty alcohols is identified by the presence of one or more domains, which are found in proteins with FAR activity. In various embodiments, the one or more domains is identified by multiple sequence alignments using hidden Markov models ("HMMs") to search large collections of protein families, for example, the Pfam collection available at the website pfam.sanger.ac.uk/. See R. D. Finn et al. (2008) *Nucl. Acids Res.* Database Issue 36:D281-D288.

In certain embodiments, the one or more protein domains by which FAR enzymes are identified belongs to a family of NAD binding domains found in the male sterility proteins of *arabidopsis* and *drosophila*, as well as in the fatty acyl reductase enzyme from the jojoba plant (JJFAR). See Aarts M G et al. (1997) *Plant J.* 12:615-623. This family of binding domains is designated "NAD_binding_4" (PF07993; see the website pfam.sanger.ac.uk/family?acc=PF07993). In various embodiments, the NAD_binding_4 domain is found near the N-terminus of the putative FAR enzyme. In various embodiments, the one or more protein domains by which enzymes with FAR activity are identified belongs to a family of domains known as a "sterile" domain (PF03015; see the website pfam.sanger.ac.uk/family?acc=PF03015), which are also found in the male sterility proteins of *Arabidopsis* species and a number of other organisms. See Aarts M G et al. (1997) *Plant J.* 12:615-623. In particular embodiments, the sterile domain is found near the C-terminus of the putative FAR enzyme. In certain specific embodiments, a FAR enzyme for use in the methods described herein is identified by the presence of at least one NAD_binding_4 domain near the N-terminus and the presence of at least one sterile domain near the C-terminus.

In certain embodiments, the NAD_binding_4 domain of the putative FAR enzyme has an amino acid sequence that is at least 10%, such as at least 15%, such as at least 20%, such as at least 25%, such as at least 30%, such as at least 35%, such as at least 40%, such as at least 45%, such as at least 50%, such as at least 60%, such as at least 70%, such as at least 80%, such as at least 85%, such as at least 90% or more identical to the amino acid sequence of a known NAD_binding_4 domain. See, e.g., Aarts M G et al. (1997) *Plant J.* 12:615-623. In various embodiments, the sterile domain of the putative FAR enzyme has an amino acid sequence that is at least 10%, such as at least 15%, such as at least 20%, such as at least 25%, such as at least 30%, such as at least 35%, such as at least 40%, such as at least 45%, such as at least 50% or more identical to the amino acid sequence of a known sterile domain. See id.

In some embodiments, the NAD_binding_4 domain of the putative FAR enzyme has an amino acid sequence that is at least 10%, such as at least 15%, such as at least 20%, such as at least 25%, such as at least 30%, such as at least 35%, such as at least 40%, such as at least 45%, such as at least 50%, such as at least 60%, such as at least 70%, such as at least 80%, such as at least 85%, such as at least 90% or more identical to the amino acid sequence of one or more example polypeptides that form the definition of the NAD_binding_4 Pfam domain (PF07993). In certain embodiments, the sterile domain of the putative FAR enzyme has an amino acid sequence that is at least 10%, such as at least 15%, such as at least 20%, such as at least 25%, such as at least 30%, such as at least 35%, such as at least 40%, such as at least 45%, such as at least 50% or more identical to the amino acid sequence of one or more example polypeptides that form the definition of the sterile Pfam domain (PF03015). In various embodiments, the NAD_binding_4 domain or the sterile domain of the putative FAR enzyme is identified by an E-value of $1 \times 10^{-4}$ or less, such as an E-value of $1 \times 10^{-5}$, such as an E-value of $1 \times 10^{-10}$, such as an E-value of $1 \times 10^{-15}$, such as an E-value of $1 \times 10^{-20}$, such as an E-value of $1 \times 10^{-25}$, such as an E-value of $1 \times 10^{-30}$ or lower. As used herein, the term E-value (expectation value) is the number of hits that would be expected to have a score equal or better than a particular hit by chance alone. Accordingly, the E-value is a criterion by which the significance of a database search hit can be evaluated. See, e.g., the website pfam.sanger.ac.uk/help; the www website csb.yale.edu/userguides/seq/hmmer/docs/node5.html.

The FAR enzymes described herein have not previously been recognized as FAR enzymes because of the low homology of the FAR coding sequences to the sequences coding for proteins with known FAR activity, such as the FAR enzymes from *S. chinensis* ((FAR Sim); GenBank Accession no. AAD38039.1; gi|5020215|gb|AAD38039.1|AF149917_1 acyl CoA reductase [*Simmondsia chinensis*]-Plant Physiol. 2000 March; 122(3):635-44. Purification of a jojoba embryo fatty acyl-coenzyme A reductase and expression of its cDNA in high erucic acid rapeseed; Metz J G, Pollard M R, Anderson L, Hayes T R, Lassner M W. PMID: 10712526), *B. mori* ((FAR Bom); GenBank Accession no. BAC79425.1; gi|33146307|dbj|BAC79425.1|fatty-acyl reductase [*Bombyx mori*]; Proc Natl Acad Sci USA 2003 Aug. 5; 100(16):9156-61. Epub 2003 Jul. 18. Pheromone gland-specific fatty-acyl reductase of the silkmoth, *Bombyx mori*. Moto K, Yoshiga T, Yamamoto M, Takahashi S, Okano K, Ando T, Nakata T, Matsumoto S. PMID: 12871998), *Arabidopsis thaliana* (GenBank Accession no. DQ446732.1 or NM_115529.1; gi|91806527|gb|DQ446732.1|*Arabidopsis thaliana* clone pENTR221-At3g44560; gi|18410556|ref|NM_115529.1|*Arabidopsis thaliana* male sterility protein, putative (AT3G56700); Plant Physiol. 2009 May 15; 166(8):787-96. Epub 2008 Dec. 4. Functional expression of five *Arabidopsis* fatty acyl-CoA reductase genes in *Escherichia coli*. Doan T T, Carlsson A S, Hamberg M, Büllow L, Stymne S, Olsson P. PMID: 19062129) or *Ostrinia scapulalis* (GenBank Accession no. EU817405.1; gi|210063138|gb|EU817405.11 *Ostrinia scapulalis* FAR-like protein XIII; Insect Biochem. Mol. Biol. 2009 February; 39(2):90-5. Epub 2008 Oct. 26 Pheromone-gland-specific fatty-acyl reductase in the adzuki bean borer, *Ostrinia scapulalis* (Lepidoptera: Crambidae) Antony B, Fujii T, Moto K, Matsumoto S, Fukuzawa M, Nakano R, Tatsuki S, Ishikawa Y.).

In certain embodiments, the FAR enzyme for use in the disclosed methods of producing fatty alcohols is endogenous to a marine bacterium and has an amino acid sequence having less than about 35% sequence identity to the amino acid sequence of a known FAR enzyme, such as those described above. In various embodiments, the FAR enzyme for use in the methods disclosed herein is endogenous to a marine bacterium and has an amino acid sequence having less than about 33% sequence identity, such as less than 31% sequence identity, such as less than about 29% sequence identity, such as less than about 27% sequence identity, such as less than about 25% sequence identity, such as less than about 23% sequence identity, even such as less than about 22% sequence identity to the amino acid sequence of a polypeptide previously recognized as possessing FAR enzyme activity.

In various embodiments, the FAR enzyme for use in the disclosed methods of producing fatty alcohols is endogenous to an organism selected from the group consisting *Vitis vinifera*, *Desulfatibacillum alkenivorans*, *Stigmatella aurantiaca*, and *Phytophthora ramorum* and has an amino acid sequence having less than about 65% sequence identity to the amino acid sequence of a known FAR enzyme, such as those described above. In various embodiments, the FAR enzyme for use in the methods disclosed herein is endogenous to a marine bacterium and has an amino acid sequence having less than about 60% sequence identity, such as less than 55% sequence identity, such as less than about 50% sequence identity, such as less than about 45% sequence identity, such as less than about 40% sequence identity, such as less than about 35% sequence identity, even such as less than about 34% sequence identity, such as less than about 33% sequence identity, such as less than about 32% sequence identity, such as less than about 31% sequence identity, such as less than about 30% sequence identity to the amino acid sequence of a polypeptide previously recognized as possessing FAR enzyme activity.

In certain embodiments, the FAR enzyme endogenous to *Marinobacter algicola* DG893 for use in the methods disclosed herein is the full-length polypeptide having the amino acid set forth in SEQ ID NO: 2. In various embodiments, the full-length FAR enzyme has an amino acid sequence that is at least about 75% identical, such as at least about 80% identical, such as at least about 85% identical, such as at least about 90% identical, such as at least about 91%, such as at least about 92%, such as at least about 93%, such as at least about 94%, such as at least about 95%, such as at least about 96%, such as at least about 97%, such as at least about 98%, such as at least about 99% identical to the sequence set forth in SEQ ID NO: 2. In certain preferred embodiments, where the amino acid sequence is less than 100% identical to that shown in SEQ ID NO: 2, all amino acid substitutions are conservative.

In various embodiments, the FAR enzyme endogenous to *M. algicola* DG893 for use in the methods disclosed herein is a functional fragment of the full-length polypeptide, the amino acid sequence of which is set forth in SEQ ID NO: 2. In certain embodiments, the amino acid sequence of the functional fragment is at least about 70%, such as at least about 75%, such as at least about 80%, such as at least about 90%, such as at least about 91%, such as at least about 92%, such as at least about 93%, such as at least about 94%, such as at least about 95%, such as at least about 96%, such as at least about 97%, such as at least about 98%, such as at least about 99% identical to the amino acid sequence of the corresponding region of SEQ ID NO: 2.

In certain embodiments, the FAR enzyme endogenous to *Marinobacter aquaeolei* for use in the methods disclosed herein is the full-length polypeptide having the amino acid set forth in SEQ ID NO: 14. In various embodiments, the full-length FAR enzyme has an amino acid sequence that is at least about 75% identical, such as at least about 75% identical, such as at least about 80% identical, such as at least about 85% identical, such as at least about 90% identical, such as at least about 91%, such as at least about 92%, such as at least about 93%, such as at least about 94%, such as at least about 95%, such as at least about 96%, such as at least about 97%, such as at least about 98%, such as at least about 99% identical to the sequence set forth in SEQ ID NO: 14. In certain preferred embodiments, where the amino acid sequence is less than 100% identical to that shown in SEQ ID NO: 14, all amino acid substitutions are conservative.

In various embodiments, the FAR enzyme endogenous to *M. aquaeolei* for use in the methods disclosed herein is a functional fragment of the full-length polypeptide, the amino acid sequence of which is set forth in SEQ ID NO: 14. In certain embodiments, the amino acid sequence of the functional fragment is at least about 70%, such as at least about 75%, such as at least about 80%, such as at least about 90%, such as at least about 91%, such as at least about 92%, such as at least about 93%, such as at least about 94%, such as at least about 95%, such as at least about 96%, such as at least about 97%, such as at least about 98%, such as at least about 99% identical to the amino acid sequence of the corresponding region of SEQ ID NO: 14.

In certain embodiments, the FAR enzyme endogenous to *Oceanobacter* sp. RED65 for use in the methods disclosed herein is the full-length polypeptide having the amino acid set forth in SEQ ID NO: 6. In various embodiments, the FAR enzyme has an amino acid sequence that is at least about 75% identical, such as at least 80% identical, such as at least about 85% identical, such as at least about 90% identical, such as at least about 91%, such as at least about 92%, such as at least about 93%, such as at least about 94%, such as at least about 95%, such as at least about 96%, such as at least about 97%, such as at least about 98%, such as at least about 99% identical to the sequence set forth in SEQ ID NO: 6. In certain preferred embodiments, where the sequence identity is less than 100%, all amino acid substitutions are conservative.

In various embodiments, the FAR enzyme endogenous to *Oceanobacter* sp. RED65 for use in the methods disclosed herein is a functional fragment of the full-length polypeptide, the amino acid sequence of which is set forth in SEQ ID NO: 6. In certain embodiments, the functional fragment has an amino acid sequence that is at least about 70%, such as at least about 75%, such as at least about 80%, such as at least about 90%, such as at least about 91%, such as at least about 92%, such as at least about 93%, such as at least about 94%, such as at least about 95%, such as at least about 96%, such as at least about 97%, such as at least about 98%, such as at least about 99% identical to the amino acid sequence of the corresponding region of SEQ ID NO: 6.

Nucleic Acids for Expression of FAR Enzymes:

In another aspect, the present disclosure provides polynucleotides encoding a FAR enzyme, or functional fragment thereof, as described above. The polynucleotide can be a DNA or RNA, and can be single-stranded or double-stranded. The polynucleotide can be isolated from a naturally occurring microorganism, or prepared wholly or partially via synthetic means. In some embodiments, the polynucleotide is a construct designed to provide for expression of the encoded FAR enzyme or functional fragment in a host microorganism. The FAR enzyme or the specific or functional fragment encoded by the polynucleotide construct may be endogenous or heterologous to the host microorganism.

In various aspects of the disclosure, the availability of a polypeptide sequence of a specific FAR enzyme provides a description of all polynucleotides capable of encoding the polypeptide of known sequence because of the known correspondence of particular codons and the amino acids they encode. In certain embodiments, the degeneracy of the genetic code is used to produce a large number of polynucleotides that encode the gamma proteobacterial FAR polypeptides described herein. Thus, for example, the codons AGA, AGG, CGA, CGC, CGG, and CGU all encode the amino acid arginine (R). Thus, at every position in the nucleic acids of the invention where an arginine is specified by a codon, the codon can be altered to any of the corresponding codons described above without altering the encoded polypeptide. In some embodiments, the polynucleotides that encode the FAR enzymes described herein are codon optimized for expression in a recombinant host cells. In particular embodiments, the polynucleotides that encode the FAR enzymes described herein are codon optimized for expression in bacteria, yeast or filamentous fungi. In various embodiments, the polynucleotides that encode the FAR enzymes described herein are codon optimized for expression in oleaginous yeast. In certain specific embodiments, the polynucleotides that encode the FAR enzymes are codon optimized for expression in *E. coli*, *S. cerevisiae* or *Y. lipolytica*.

In certain embodiments, the present disclosure provides an isolated nucleic acid encoding a FAR enzyme from a marine bacterium. In some embodiments, the nucleic acid encodes a FAR enzyme having an amino acid sequence that is at least about 75% identical, at least about 80% identical, such as at least about 85% identical, such as at least about 90% identical, such as at least about 91%, such as at least about 92%, such as at least about 93%, such as at least about 94%, such as at least about 95%, such as at least about 96%, such as at least about 97%, such as at least about 98%, such as at least about 99% identical to the sequence set forth in SEQ ID NO: 2. In some embodiments, the nucleic acid encodes a FAR enzyme having an amino acid sequence that is at least about 75% identical, at least about 80% identical, such as at least about 85% identical, such as at least about 90% identical, such as at least about 91%, such as at least about 92%, such as at least about 93%, such as at least about 94%, such as at least about 95%, such as at least about 96%, such as at least about 97%, such as at least about 98%, such as at least about 99% identical to the sequence set forth in SEQ ID NO: 14. In other embodiments, the nucleic acid encodes a FAR enzyme having an amino acid sequence that is at least about 75% identical, such as at least 80% identical, such as at least about 85% identical, such as at least about 90% identical, such as at least about 91%, such as at least about 92%, such as at least about 93%, such as at least about 94%, such as at least about 95%, such as at least about 96%, such as at least about 97%, such as at least about 98%, such as at least about 99% identical to the sequence set forth in SEQ ID NO: 6.

In various embodiments, the present disclosure provides DNA constructs, vectors and polynucleotides encoding FAR enzymes for expression in heterologous recombinant host cells. In certain embodiments, the DNA constructs, vectors and polynucleotides comprise a sequence that encodes a FAR enzyme endogenous to a marine bacterium. In some embodiments, the DNA constructs, vectors and polynucleotides comprise a sequence that encodes a FAR enzyme endogenous to a *Marinobacter* species. In various embodiments, the DNA constructs, vectors and polynucleotides comprise a sequence that encodes a FAR enzyme endogenous to an *Oceanobacter* species. In some particular embodiments, the DNA constructs, vectors and polynucleotides comprise a sequence that encodes a FAR enzyme endogenous to *M. algicola* DG893 or *M. aquaeolei*. In other particular embodiments, the DNA constructs, vectors and polynucleotides comprise a sequence that encodes a FAR enzyme endogenous to *Oceanobacter* sp. RED65. In some particular embodiments, the polynucleotide is a codon optimized polynucleotide, such as a polynucleotide having at least 90% (at least 93%, at least 95%, at least 96%, at least 97%, at least 98%, at least 99% and even 100%) sequence identity to SEQ ID NOs: 1, 3, 5, 7 or 13.

In certain embodiments, the DNA constructs, vectors and polynucleotides comprise a sequence that encodes the full length FAR polypeptide encompassed by the invention. In some embodiments, the DNA construct, vector or polynucleotide comprises a sequence that encodes a full length FAR endogenous to a *Marinobacter* strain. In some embodiments the strain is *M. algicola* DG893 and in other embodiments the strain is a *M. aquaeolei*. In other embodiments, the DNA constructs, vectors and polynucleotides comprise a sequence that encodes a functional fragment of the FAR polypeptide of *M. algicola* DG893 or a *M. aquaeolei*. In various embodiments, the DNA constructs, vectors and polynucleotides comprise a sequence that encodes the full length FAR polypeptide endogenous to *Oceanobacter* sp. RED65. In some embodiments, the DNA constructs, vectors and polynucleotides comprise a sequence that encodes a functional fragment of the FAR polypeptide of *Oceanobacter* sp. RED65.

In certain embodiments, the DNA constructs, vectors and polynucleotides comprise a sequence that encodes a full-length FAR polypeptide endogenous to *M. algicola* DG893 having an amino acid sequence that is at least about 75% identical, such as at least 80% identical, such as at least about 85% identical, such as at least about 90% identical, such as at least about 91%, such as at least about 92%, such as at least about 93%, such as at least about 94%, such as at least about 95%, such as at least about 96%, such as at least about 97%, such as at least about 98%, such as at least about 99% identical to the amino acid sequence set forth in SEQ ID NO: 2.

In some embodiments, the DNA constructs, vectors and polynucleotides comprise a sequence that encodes a functional fragment of the FAR enzyme having an amino acid sequence that is at least about 80% identical, such as at least about 85% identical, such as at least about 90% identical, such as at least about 91%, such as at least about 92%, such as at least about 93%, such as at least about 94%, such as at least about 95%, such as at least about 96%, such as at least about 97%, such as at least about 98%, such as at least about 99% identical to the amino acid sequence of the corresponding region of SEQ ID NO: 2.

In certain embodiments, the DNA constructs, vectors and polynucleotides comprise a sequence that encodes a full-length FAR polypeptide endogenous to *M. aquaeolei* having an amino acid sequence that is at least about 75% identical, such as at least 80% identical, such as at least about 85% identical, such as at least about 90% identical, such as at least about 91%, such as at least about 92%, such as at least about 93%, such as at least about 94%, such as at least about 95%, such as at least about 96%, such as at least about 97%, such as at least about 98%, such as at least about 99% identical to the amino acid sequence set forth in SEQ ID NO: 14.

In some embodiments, the DNA constructs, vectors and polynucleotides comprise a sequence that encodes a functional fragment of the FAR enzyme having an amino acid sequence that is at least about 80% identical, such as at least about 85% identical, such as at least about 90% identical, such as at least about 91%, such as at least about 92%, such as at least about 93%, such as at least about 94%, such as at least about 95%, such as at least about 96%, such as at least about 97%, such as at least about 98%, such as at least about 99% identical to the amino acid sequence of the corresponding region of SEQ ID NO: 14.

In various embodiments, the DNA constructs, vectors and polynucleotides comprise a sequence that encodes a full-length FAR polypeptide endogenous to *Oceanobacter* sp. RED65 having an amino acid sequence that is at least about 80% identical, such as at least about 85% identical, such as at least about 90% identical, such as at least about 91%, such as at least about 92%, such as at least about 93%, such as at least about 94%, such as at least about 95%, such as at least about 96%, such as at least about 97%, such as at least about 98%, such as at least about 99% identical to the amino acid sequence set forth in SEQ ID NO: 6.

In some embodiments, the DNA constructs, vectors and polynucleotides comprise a sequence that encodes a functional fragment of the FAR enzyme that has an amino acid sequence that is at least about 80% identical, such as at least about 85% identical, such as at least about 90% identical, such as at least about 91%, such as at least about 92%, such as at least about 93%, such as at least about 94%, such as at least about 95%, such as at least about 96%, such as at least about 97%, such as at least about 98%, such as at least about 99% identical to the amino acid sequence of the corresponding region of SEQ ID NO: 6.

In still other embodiments, the present disclosure provides DNA constructs, vectors and polynucleotides encoding FAR enzymes endogenous to a marine bacterium, wherein the FAR enzyme is selected from the group consisting of FAR_Mac (from marine actinobacterium species PHSC20C1), FAR_JVC (JCVI_ORF__1096697648832, GenBank Accession No. EDD40059.1; from a marine metagenome), FAR_Fer (JCVI_SCAF__1101670217388; from a marine bacterium found at a depth of 12 m in an upwelling in the area of Fernandina Island, the Galapagos Islands, Ecuador), FAR_Key (JCVI_SCAF__1097205236585, from a marine bacterium found at a depth of 1.7 m off the coast of Key West Fla.), and FAR_Gal (JCVI_SCAF__1101670289386, at a depth of 0.1 m at Isabella Island, Galapagos Islands, Ecuador).

In still other embodiments, the present disclosure provides DNA constructs, vectors and polynucleotides encoding FAR enzymes endogenous to a marine bacterium selected from the group consisting of *M. alkaliphilus, M. aquaeolei, M. arcticus, M. bryozoorum, M. daepoensis, M. excellens, M. flavimaris, M. guadonensis, M. hydrocarbonoclasticus, M. koreenis, M. lipolyticus, M. litoralis, M. lutaoensis, M. maritimus, M. sediminum, M. squalenivirans, M. vinifirmus, Meptuniibacter caesariensis* species strain MED92, *Reinekea* sp. strain MED297, *Marinomonas* sp. strain MED121, unnamed gammaproteobacterium strain HTCC2207, *Marinobacter* sp. strain ELB17, *Oceanobacter kriegii*, and *Oceanobacter* strain WH099.

In yet other embodiments, the present disclosure provides DNA constructs, vectors and polynucleotides encoding a FAR enzyme endogenous to an organism selected from the group consisting of *Vitis vinifera, Desulfatibacillum alkenivorans, Stigmatella aurantiaca* and *Phytophthora ramorum*.

In some embodiments, the polynucleotide of the invention encodes a FAR enzyme encompassed by the invention and comprises a nucleic acid comprising at least 70%, at least 75%, at least 80%, at least 85%, at least 90%, at least 93%, at least 95%, at least 96%, at least 97%, and at least 99% sequence identity with SEQ ID NOs: 1, 3, 5, 7, or 13 and hybridizes with SEQ ID NOs: 1, 3, 5, 7, or 13. Nucleic acids "hybridize" when they associate, typically in solution. Nucleic acids hybridize due to a variety of well-characterized physico-chemical forces, such as hydrogen bonding, solvent exclusion, base stacking and the like. As used herein, the term "stringent hybridization wash conditions" in the context of nucleic acid hybridization experiments, such as Southern and Northern hybridizations, are sequence dependent, and are different under different environmental parameters. An extensive guide to the hybridization of nucleic acids is found in Tijssen, 1993, "Laboratory Techniques in Biochemistry and Molecular Biology-Hybridization with Nucleic Acid Probes," Part I, Chapter 2 (Elsevier, New York), which is incorporated herein by reference. For polynucleotides of at least 100 nucleotides in length, low to very high stringency conditions are defined as follows: prehybridization and hybridization at 42° C. in 5×SSPE, 0.3% SDS, 200 μg/ml sheared and denatured salmon sperm DNA, and either 25% formamide for low stringencies, 35% formamide for medium and medium-high stringencies, or 50% formamide for high and very high stringencies, following standard Southern blotting procedures. For polynucleotides of at least 100 nucleotides in length, the carrier material is finally washed three times each for 15 minutes using 2×SSC, 0.2% SDS at least at 50° C. (low stringency), at least at 55° C. (medium stringency), at least at 60° C. (medium-high stringency), at least at 65° C. (high stringency), and at least at 70° C. (very high stringency).

The polynucleotides encoding FAR enzymes for expression in heterologous recombinant host cells as described herein are operably linked to a promoter, and optionally, to other control sequences. Suitable promoters include constitutive promoters, regulated promoters, and inducible promoters. Appropriate promoter sequences can be obtained from genes encoding extracellular or intracellular polypeptides which are either endogenous or heterologous to the host cell. Methods for the isolation, identification and manipulation of promoters of varying strengths are available in or readily adapted from the art. See e.g., Nevoigt et al. (2006) *Appl. Environ. Microbiol.* 72:5266-5273, the disclosure of which is herein incorporated by reference in its entirety.

In certain embodiments, the DNA constructs, vectors and polynucleotides are suitable for expression of a heterologous FAR enzyme in bacteria. For bacterial host cells, suitable promoters for directing transcription of the nucleic acid constructs of the present disclosure, include the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, *Bacillus megaterium* promoters, and prokaryotic beta-lactamase gene (Villa-Kamaroff et al., *Proc. Natl. Acad. Sci. USA* 75: 3727-3731 (1978)), as well as the tac promoter (DeBoer et al., *Proc. Natl. Acad. Sci. USA* 80: 21-25 (1993)). Additional promoters include tip promoter, phage lambda PL, T7 promoter, promoters found at PromEC (the website margalit.huji.acil/promec/index.html) and the like. Promoters suitable for use in the present disclosure are described in "Useful proteins from recombinant bacteria" in *Scientific American* 242:74-94 (1980); and in Sambrook et al (2001) *Molecular Cloning: A Laboratory Manual*, 3$^{rd}$ ed., Cold Spring Harbor Laboratory Press, New York.

In various embodiments, the DNA constructs, vectors and polynucleotides are suitable for expression of a heterologous FAR enzyme in yeast. In certain embodiments, the DNA constructs, vectors and polynucleotides are suitable for expression of a heterologous FAR enzyme in oleaginous yeast. In various embodiments, the DNA constructs, vectors and polynucleotides are suitable for expression of a heterologous FAR enzyme in the oleaginous yeast *Y. lipolytica*. In certain embodiments, the DNA constructs, vectors and polynucleotides are suitable for expression of a heterologous FAR enzyme in *S. cerevisiae*. For yeast host cells, suitable promoters for directing transcription of the nucleic acid constructs of the present disclosure are known to the skilled artisan and include, but are not limited to, an enolase (ENO-1_gene) promoter, a galactokinase (GAL1) promoter, an alcohol dehydrogenase/glyceraldehyde-3-phosphate dehydrogenase (ADH2/GAP) promoter, a translation elongation factor EF-1 alpha (TEF1) promoter as well as those described by Romanos et al. (1992) *Yeast* 8:423-488. In other embodiments, promoters include the TEF1 promoter and an RPS7 promoter.

For filamentous fungal host cells, suitable promoters for directing the transcription of the nucleic acid constructs of the present disclosure include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans acetamidase*, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof. Examples of suitable promoters useful for directing the transcription of the nucleotide constructs of the present invention in a filamentous fungal host cell are promoters such as cbh1, cbh2, egl1, egl2, pepA, hfb1, hfb2, xyn1, amy, and glaA (Nunberg et al., Mol. Cell. Biol., 4:2306-2315 (1984), Boel et al., EMBO J. 3:1581-1585 ((1984) and EPA 137280).

In various embodiments, an expression vector optionally contains a ribosome binding site (RBS) for translation initiation, and a transcription terminator, such as PinII. The vector also optionally includes appropriate sequences for amplifying expression, e.g., an enhancer.

In various embodiments, the polynucleotides useful for expressing heterologous FAR enzymes in recombinant host cells are operably linked to other control sequences, including but not limited to, a transcription terminator sequence, a signal sequence that when translated directs the expressed polypeptide into the secretory pathway of the recombinant host cell, and a polyadenylation sequence (eukaryotes). The choice of appropriate control sequences for use in the polynucleotide constructs of the present disclosure is within the skill in the art and in various embodiments is dependent on the recombinant host cell used and the desired method of recovering the fatty alcohol compositions produced.

The instant disclosure further relates to recombinant expression vectors for use in the methods described herein. A recombinant expression vector can be any vector, e.g., a plasmid or a virus, which can be manipulated by recombinant DNA techniques to facilitate expression of a heterologous FAR enzyme in a recombinant host cell. In certain embodiments, the expression vectors is integrated into the chromosome of the recombinant host cell and comprises one or more heterologous genes operably linked to one or more control sequences useful for production of a FAR enzyme. In other embodiments, the expression vector is an extra chromosomal replicative DNA molecule, e.g., a linear or closed circular plasmid, that is found either in low copy number (e.g., from about 1 to about 10 copies per genome equivalent) or in high copy number (e.g., more than about 10 copies per genome equivalent). In various embodiments, the expression vector includes a selectable marker, such as a gene that confers antibiotic resistance (e.g., ampicillin, kanamycin, chloramphenicol or tetracycline resistance) to the recombinant host organism that comprises the vector.

Expression vectors which, in certain embodiments, are useful for expressing FAR enzymes as disclosed herein are commercially available, e.g., from Sigma-Aldrich Chemicals, St. Louis Mo. and Stratagene, LaJolla Calif. In some embodiments, examples of suitable expression vectors are plasmids which are derived from pBR322 (Gibco BRL), pUC (Gibco BRL), pREP4, pCEP4 (Invitrogen) or pPoly (Lathe et al., 1987, *Gene* 57:193-201).

In certain embodiments, the present disclosure provides a plasmid for expression of heterologous genes in *E. coli*. Expression vector pCK110900, which comprises a P15A origin of replication (P15A ori), lac a CAP binding site, a lac promoter, a T7 ribosomal binding site (T7g10 RBS) and a chloramphenicol resistance gene (camR). This expression vector is depicted in FIG. 3 of U.S. Patent Publication No. 2006/0195947, which is incorporated herein by reference in its entirety.

In particular embodiments, the present disclosure provides an autonomous replicating plasmid for expression of heterologous genes in *Yarrowia*, and particularly in *Y. lipolytica*. This plasmid vector (pCEN411; FIG. 1) was engineered with cassettes for expression of a gene encoding resistance to hygromycin (HygB$^R$) and for expression of a FAR gene optimized for *Y. lipolytica*. In these embodiments, expression of each gene is independently regulated by a strong, constitutive promoter isolated from *Y. lipolytica*: pTEF1 for FAR expression and pRPS7 for HygB$^R$ expression. When this plasmid was transformed into *Y. lipolytica*, it conferred resistance to hygromycin and directed expression of FAR. This plasmid can be further modified for expression of heterologous genes useful for fatty alcohol production in yeast, inter alia, *Y. lipolytica*.

In some embodiments, expression vectors as described herein are adapted for over expression of genes encoding enzymes other than FAR that are directly involved in fatty acid biosynthesis. In particular embodiments, the over expressed gene encodes a protein selected from a fatty acid synthase (FAS), an acyl-ACP thioesterase (TE), a fatty acyl-CoA synthase (FACS) and an acetyl-CoA carboxylase (ACC). In some embodiments, the expression vector encoding the FAR enzyme and the expression vector encoding a second enzyme (e.g., an FAS, TE, FACS or ACC) are separate nucleic acids. In other embodiments, the heterologous FAR enzyme and the second enzyme are encoded on the same expression vector, and expression of each enzyme is independently regulated by a different promoter.

Methods, reagents and tools for transforming host cells described herein, such as bacteria, yeast (including oleaginous yeast) and filamentous fungi are known in the art. General methods, reagents and tools for transforming, e.g., bacteria can be found, for example, in Sambrook et al (2001) *Molecular Cloning: A Laboratory Manual*, 3$^{rd}$ ed., Cold Spring Harbor Laboratory Press, New York. Methods, reagents and tools for transforming yeast are described in "Guide to Yeast Genetics and Molecular Biology," C. Guthrie and G. Fink, Eds., *Methods in Enzymology* 350 (Academic Press, San Diego, 2002). Methods, reagents and tools for transforming *Y. lipolytica* are found in "*Yarrowia lipolytica*," C. Madzak, J. M. Nicaud and C. Gaillardin in "Production of Recombinant Proteins. Novel Microbial and Eucaryotic Expression Systems," G. Gellissen, Ed. 2005. In some embodiments, introduction of the DNA construct or vector of the present invention into a host cell can be effected by calcium phosphate transfection, DEAE-Dextran mediated transfection, electroporation, or other common techniques (See Davis et al., 1986, *Basic Methods in Molecular Biology*, which is incorporated herein by reference). The present invention also provides a method for producing a recombinant host cell, wherein the method comprises: (a) providing a nucleic acid construct of the present invention, wherein the nucleic acid construct comprises a polynucleotide encoding a FAR polypeptide as described herein; and (b) transforming a host cell with the nucleic acid construct to produce a recombinant cell. In particular embodiments, the host cell will be a bacterial cell and in other particular embodiments the host cell will be a yeast cell.

Recombinant Microorganisms for Production of Fatty Alcohols:

In yet another aspect, the present disclosure provides recombinant microorganisms engineered to express a heterologous FAR enzyme, or functional fragment thereof, as described herein. In certain particular aspects, the present disclosure provides recombinant microorganisms engineered to express a heterologous FAR enzyme from a marine gammaproteobacterium, or functional fragment thereof, as described herein for the production of fatty alcohols from fatty acyl-ACP substrates. In other embodiments, the present disclosure provides recombinant microorganisms engineered to express a heterologous FAR enzyme from an organism selected from the group consisting of *Vitis vinifera, Desulfatibacillum alkenivorans, Stigmatella aurantiaca* and *Phytophthora ramorum*. In certain embodiments, the FAR enzyme can be expressed in the host cell in which it is found naturally. In various embodiments, the FAR enzyme can be expressed in a heterologous host cell. In particular, when expressed in heterologous host cells described herein, the FAR enzymes are capable of generating high yields of total and secreted fatty alcohols from fatty acyl-ACP substrates.

In various embodiments, the heterologous host cells useful for expressing the FAR enzymes described herein are selected from bacteria, yeast or filamentous fungi. In certain embodiments, the yeast is an oleaginous yeast.

In certain embodiments, microorganisms useful as recombinant host cells are wild-type microorganisms.

In various embodiments, microorganisms useful as recombinant host cells are genetically modified. As used herein, "genetically modified" microorganisms include microorganisms having one or more endogenous genes removed, microorganisms having one or more endogenous genes with reduced expression compared to the parent or wild-type microorganism, or microorganisms having one or more genes over expressed compared to the parent or wild-type microorganism. In certain embodiments, the one or more genes that are over expressed are endogenous to the microorganism. In some embodiments, the one or more genes that are over expressed are heterologous to the microorganism.

In certain embodiments, the genetically modified microorganism comprises an inactivated or silenced endogenous gene that codes for a protein involved in the biosynthesis of fatty acyl-CoA substrates. In particular embodiments, the inactive or silenced gene encodes a fatty acyl-ACP thioesterase or a fatty acyl-CoA synthetase (FACS).

In some embodiments, the host cell is a prokaryotic cell. Suitable prokaryotic cells include gram positive, gram negative and gram-variable bacterial cells. In certain embodiments, host cells include, but are not limited to, species of a genus selected from the group consisting of *Agrobacterium, Alicyclobacillus, Anabaena, Anacystis, Acinetobacter, Acidothermus, Arthrobacter, Azobacter, Bacillus, Bifidobacterium, Brevibacterium, Butyrivibrio, Buchnera, Campestris, Camplyobacter, Clostridium, Corynebacterium, Chromatium, Coprococcus, Cyanobacteria, Escherichia, Enterococcus, Enterobacter, Erwinia, Fusobacterium, Faecalibacterium, Francisella, Flavobacterium, Geobacillus, Haemophilus, Helicobacter, Klebsiella, Lactobacillus, Lactococcus, Ilyobacter, Micrococcus, Microbacterium, Mesorhizobium, Methylobacterium, Methylobacterium, Mycobacterium, Neisseria, Pantoea, Pseudomonas, Prochlorococcus, Rhodobacter, Rhodopseudomonas, Rhodopseudomonas, Roseburia, Rhodospirillum, Rhodococcus, Scenedesmun, Streptomyces, Streptococcus, Synechooccus, Synechocystis, Saccharomonospora, Staphylococcus, Serratia, Salmonella, Shigella, Thermoanaerobacterium, Tropheryma, Tularensis, Temecula, Thalassiosira, Thermosynechococcus, Thermococcus, Ureaplasma, Xanthomonas, Xylella, Yersinia* and *Zymomonas*. In particular embodiments, the host cell is a species of a genus selected from the group consisting of *Agrobacterium, Arthrobacter, Clostridium, Corynebacterium, Escherichia, Erwinia, Geobacillus, Klebsiella, Lactobacillus, Mycobacterium, Pantoea, Rhodococcus, Streptomyces* and *Zymomonas*.

In certain embodiments, the recombinant host cell is an industrial bacterial strain. Numerous bacterial industrial strains are known and suitable for use in the methods disclosed herein. In some embodiments, the bacterial host cell is a species of the genus *Bacillus*, e.g., *B. thuringiensis, B. anthracis, B. megaterium, B. subtilis, B. lentils, B. circulans, B. pumilus, B. lautus, B. coagulans, B. brevis, B. firmus, B. alkaophius, B. licheniformis, B. clausii, B. stearothermophilus, B. halodurans* and *B. amyloliquefaciens*. In particular embodiments, the host cell is a species of the genus *Bacillus* and is selected from the group consisting of *B. subtilis, B. pumilus, B. licheniformis, B. clausii, B. stearothermophilus, B. megaterium* and *B. amyloliquefaciens*.

In some embodiments the bacterial host cell is a species of the genus *Erwinia*, e.g., *E. uredovora, E. carotovora, E. ananas, E. herbicola, E. punctata* or *E. terreus*.

In other embodiments the bacterial host cell is a species of the genus *Pantoea*, e.g., *P. citrea* or *P. agglomerans*.

In still other embodiments, the bacterial host cell is a species of the genus *Streptomyces*, e.g., *S. ambofaciens, S. achromogenes, S. avermitilis, S. coelicolor, S. aureofaciens, S. aureus, S. fungicidicus, S. griseus* or *S. lividans*.

In further embodiments, the bacterial host cell is a species of the genus *Zymomonas*, e.g., *Z. mobilis* or *Z. lipolytica*.

In further embodiments, the bacterial host cell is a species of the genus *Rhodococcus*, e.g. *R. opacus*.

In particular embodiments, the bacterial host cell is a species of the genus *Escherichia*, e.g., *E. coli*. In certain embodiments, the *E. coli* is a wild-type bacterium. In various embodiments, the wild-type *E. coli* bacterial strain useful in the processes described herein is selected from, but not limited to, strain W3110, strain MG1655 and strain BW25113. In other embodiments, the *E. coli* is genetically modified. Examples of genetically modified *E. coli* useful as recombinant host cells include, but are not limited to, genetically modified *E. coli* found in the Keio Collection, available from the National BioResource Project at NBRP *E. coli*, Microbial Genetics Laboratory, National Institute of Genetics 1111 Yata, Mishima, Shizuoka, 411-8540 Japan (www at shigen.nig.ac.jp/ecoli/strain/top/top.jsp).

In particular embodiments, the genetically modified *E. coli* comprises an inactivated or silenced endogenous fadD gene, which codes for an acyl-CoA synthetase protein. In other embodiments the genetically modified *E. coli* comprises an inactivated of silenced endogenous fadK gene, which codes for an endogenous short-chain acyl-CoA synthetase. In still other embodiments, the genetically modified *E. coli* comprises an inactivated or silenced endogenous fadD gene and an inactivated or silenced endogenous fadK gene. In other embodiments, the genetically modified *E. coli* comprises an endogenous fadD gene that has reduced expression compared to the parent or wild-type strain. In various embodiments, the genetically modified *E. coli* comprises an endogenous fadK gene that has reduced expression compared to the parent or wild-type strain.

In certain embodiments, the recombinant host cell is a yeast. In various embodiments, the yeast host cell is a species of a genus selected from the group consisting of *Candida, Hansenula, Saccharomyces, Schizosaccharomyces, Pichia, Kluyveromyces*, and *Yarrowia*. In particular embodiments, the yeast host cell is a species of a genus selected from the group consisting of *Saccharomyces, Candida, Pichia* and *Yarrowia*.

In various embodiments, the yeast host cell is selected from the group consisting of *Hansenula polymorpha, Saccharomyces cerevisiae, Saccaromyces carlsbergensis, Saccharomyces diastaticus, Saccharomyces norbensis, Saccharomyces kluyveri, Schizosaccharomyces pombe, Pichia pastoris, Pichia finlandica, Pichia trehalophila, Pichia ferniemtans, Pichia kodamae, Pichia membranaefaciens, Pichia opuntiae, Pichia thermotolerans, Pichia salictaria, Pichia quercuum, Pichia pijperi, Pichia stipitis, Pichia methanolica, Pichia angusta, Kluyveromyces lactis, Candida albicans, Candida krusei, Candida ethanolic* and *Yarrowia lipolytica* and synonyms or taxonomic equivalents thereof.

In certain embodiments, the yeast host cell is a wild-type cell. In various embodiments, the wild-type yeast cell strain is selected from, but not limited to, strain BY4741, strain FL100a, strain INVSC1, strain NRRL Y-390, strain NRRL Y-1438, strain NRRL YB-1952, strain NRRL Y-5997, strain NRRL Y-7567, strain NRRL Y-1532, strain NRRL YB-4149 and strain NRRL Y-567. In other embodiments, the yeast host cell is genetically modified. Examples of genetically modified yeast useful as recombinant host cells include, but are not limited to, genetically modified yeast found in the Open Biosystems collection found at the www website openbiosystems.com/GeneExpression/Yeast/YKO/. See Winzeler et al. (1999) Science 285:901-906.

In other embodiments, the recombinant host cell is an oleaginous yeast. Oleaginous yeasts are organisms that accumulate lipids such as tri-acyl glycerols. Examples of oleaginous yeast include, but are not limited to, organisms selected from the group consisting of *Yarrowia lipolytica, Yarrowia paralipolytica, Candida revkaufi, Candida pulcherrima, Candida tropicalis, Candida utilis, Candida curvata D, Candida curvata R, Candida diddensiae, Candida boldinii, Rhodotorula glutinous, Rhodotorula graminis, Rhodotorula mucilaginosa, Rhodotorula minuta, Rhodotorula bacarum, Rhodosporidium toruloides, Cryptococcus (terricolus) albidus* var. *albidus, Cryptococcus laurentii, Trichosporon pullans, Trichosporon cutaneum, Trichosporon cutancum, Trichosporon pullulans, Lipomyces starkeyii, Lipomyces lipoferus, Lipomyces tetrasporus, Endomycopsis vernalis, Hansenula ciferri, Hansenula saturnus*, and *Trigonopsis variables*. In particular embodiments, the oleaginous yeast is *Y. lipolytica*. In certain embodiments, *Yarrowia lipolytica* strains include, but are not limited to, DSMZ 1345, DSMZ 3286, DSMZ 8218, DSMZ 70561, DSMZ 70562, DSMZ 21175, and also strains available from the Agricultural Research Service (NRRL) such as but not limited to NRRL YB-421, NRRL YB-423, NRRL YB-423-12 and NRRL YB-423-3.

In certain embodiments, the oleaginous yeast is a wild-type organism. In other embodiments, the oleaginous yeast is genetically modified.

In yet other embodiments, the recombinant host cell is a filamentous fungus. In certain embodiments, the filamentous fungal host cell is a species of a genus selected from the group consisting of *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora, Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Trametes, Tolypocladium, Trichoderma, Verticillium, Volvariella*, and teleomorphs, synonyms or taxonomic equivalents thereof.

In some embodiments, the filamentous fungal host cell is an *Aspergillus* species, a *Chrysosporium* species, a *Corynascus* species, a *Fusarium* species, a *Humicola* species, a *Myceliophthora* species, a *Neurospora* species, a *Penicillum* species, a *Tolypocladium* species, a *Tramates* species, or *Trichoderma* species. In other embodiments, the *Trichoderma* species is selected from *T. longibrachiatum, T. viride, Hypocrea jecorina* and *T. reesei*; the *Aspergillus* species is selected from *A. awamori, A. fumigatus, A. japonicus, A. nidulans, A. niger, A. aculeatus, A. foetidus, A. oryzae, A. sojae*, and *A. kawachi*; the *Chrysosporium* species is *C. lucknowense*; the *Fusarium* species is selected from *F. graminum, F. oxysporum* and *F. venenatum*; the *Myceliophthora* species is *M. thermophilia*; the *Neurospora* species is *N. crassa*; the *Humicola* species is selected from *H. insolens, H. grisea*, and *H. lanuginosa*; the *Penicillum* species is selected from *P. purpurogenum, P. chrysogenum*, and *P. verruculosum*; the *Thielavia* species is *T. terrestris*; and the *Trametes* species is selected from *T. villosa* and *T. versicolor*.

In some embodiments, the filamentous fungal host is a wild-type organism. In other embodiments, the filamentous fungal host is genetically modified.

In certain particular embodiments, recombinant host cells for use in the methods described herein are derived from strains of *Escherichia coli, Bacillus, Saccharomyces, Streptomyces* and *Yarrowia*.

In various embodiments, recombinant host cells which are useful in the practice of the present disclosure include prokaryotic and eukaryotic cells which are readily accessible from a number of culture collections, e.g., the American Type Culture Collection (ATCC), Deutsche Sammlung von Mikroorganismen und Zellkulturen GmbH (DSMZ) (German Collection of Microorganisms and Cell Culture), Centraalbureau Voor Schimmelcultures (CBS), and Agricultural Research Service Patent Culture Collection, Northern Regional Research Center (NRRL).

In various embodiments, the recombinant microorganism over expresses a gene that encodes a FAR enzyme. In some embodiments, the FAR enzyme is endogenous to the microorganism. In other embodiments, the FAR enzyme is heterologous to the microorganism.

In certain embodiments, the recombinant microorganism over expresses a gene that encodes one or more proteins other than a FAR enzyme. In various embodiments, the one or more over expressed protein increases the rate at which the recombinant cell produces the acyl-thioester FAR substrate, e.g., the compound of formula (I) shown above. In some embodiments, the one or more over expressed genes encodes a protein directly involved in fatty acid biosynthesis. In particular embodiments, the one or more over expressed genes encode a protein selected from a fatty acid synthase (FAS), an acyl-ACP thioesterase (TE), a fatty acyl-CoA synthase (FACS) and an acetyl-CoA carboxylase (ACC). In some embodiments, the over expressed gene is endogenous to the microorganism. In other embodiments, the over expressed gene is heterologous to the microorganism.

Figure 13:
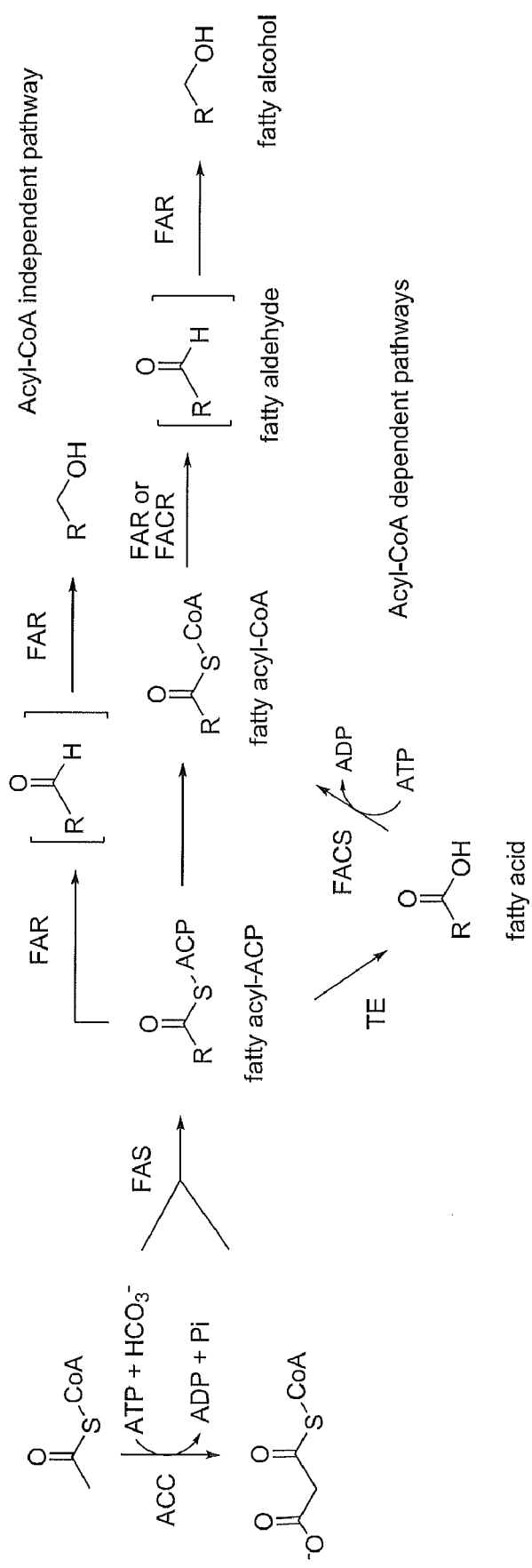
FIG. 13 depicts biosynthetic pathways for fatty alcohol production via a) an acyl-CoA dependent pathway utilizing fatty acyl-ACP and fatty acyl-CoA intermediates and b) an acyl-CoA independent pathway utilizing fatty acyl-ACP intermediates but not a fatty acyl-CoA intermediate, wherein "R" as used in the compound formulas is a C8 to C24 saturated, unsaturated, linear, branched or cyclic hydrocarbon.

"Fatty acid synthase (FAS)" refers to an enzyme or enzyme complex that catalyzes the conversion of acetyl-CoA and malonyl-CoA units to fatty acyl-ACP as set forth in Scheme II, and reference is also made to FIG. 13:

Scheme II

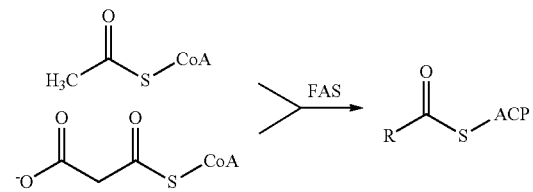

wherein R has the same meaning as set forth above in the definitions. In certain embodiments, the FAS is composed of more than one distinct enzymatic activity. In various embodiments, the distinct enzymatic activities reside in separate polypeptides. In some embodiments, the separate polypeptides form one or more protein complexes.

The term "acyl-ACP thioesterase (TE)" refers to an enzyme that catalyzes the cleavage of acyl-ACP to form a fatty acid, as shown in Scheme III and reference is also made to FIG. 13, wherein R has the same meaning as set forth above:

Scheme III

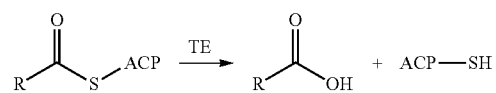

"FACS" refers to an enzyme that catalyzes the formation of the covalent complex between the acyl portion of the fatty acid and Coenzyme A as shown below in Scheme IV, wherein R has the same meaning as set forth above:

Scheme IV

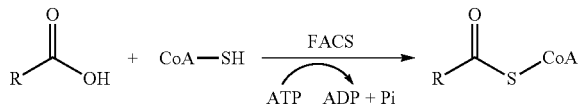

The term "acetyl-CoA carboxylase (ACC)" refers to an enzyme that catalyzes the conversion of acetyl-CoA to malonyl-CoA as shown below in Scheme V:

Scheme V

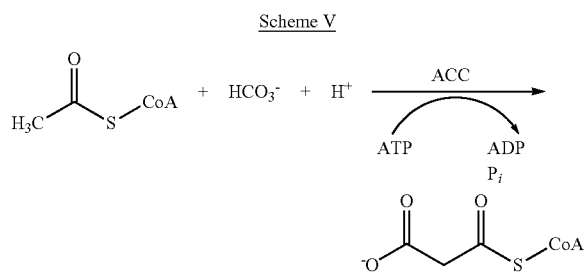

Synthesis of Fatty Alcohols by an Acyl-CoA Independent Pathway:

FIG. 13 illustrates the biosynthetic pathways for fatty alcohol formation. FAR enzymes can act directly on fatty acyl-CoA substrates to form fatty alcohols. However, as described in more detail herein, the present inventors have discovered that the amount of fatty alcohols produced in certain microorganisms comprising a gene encoding a FAR encompassed by the invention and lacking a functional endogenous fatty acyl-CoA synthetase (FACS) is comparable to the amount of fatty alcohol produced by the microorganism that has a functional endogenous FACS gene. Referring to FIG. 13, a recombinant microorganism that lacks a functional FACS gene does not catalyze the formation of fatty acyl-CoA substrates from fatty acids. Accordingly, the present inventors have posited that FAR enzymes (such as marine gammaproteobacterium FAR enzymes) as described herein catalyze the biosynthesis of fatty alcohols from fatty acyl-ACP substrates via an acyl-CoA independent pathway in lieu of, or in addition to, using fatty acyl-CoA substrates.

In certain embodiments, the present disclosure relates to the use of a FAR enzyme as described herein, e.g., a FAR enzyme from a marine bacterium, for producing a fatty alcohol composition. The discovery that FAR enzymes described herein utilized fatty acyl-ACP substrates instead of or in addition to, fatty acyl-CoA substrates provided for more efficient methods for producing fatty alcohol. In hosts, such as *E. coli* which convert fatty acyl-ACP to fatty acyl-CoA via free fatty acids, the formation of fatty acyl-CoA complexes requires ATP. Thus, in the acyl-CoA independent pathway because production of fatty alcohols by FAR enzymes (e.g., marine bacterial FAR enzymes) from fatty acyl-ACP as described herein bypasses this step, less energy is used to form the fatty alcohol compositions. The present inventors' discovery of the mechanism of action of FARs as encompassed by the invention further allows for the production of fatty alcohols in recombinant cells that do not produce fatty acyl-CoA substrates or that produce low levels of the acyl-CoA substrates compared to wild-type or parent microorganisms. Accordingly fatty alcohols can be produced by a recombinant microorganism that lacks a functional endogenous enzyme involved in the biosynthesis of fatty acyl-CoA substrates. Thus in some aspects, fatty alcohols can be produced by a recombinant microorganism that express a gene encoding a FAR enzyme described herein and that lacks a gene encoding a fatty acyl-CoA synthetase (FACS) and/or a gene encoding a fatty acyl-ACP thioesterase (TE).

Thus, in some embodiments, the present disclosure provides for a mechanism of action for the production of fatty alcohols by an acyl-CoA independent pathway, wherein certain FAR enzymes encompassed by the invention may act on fatty acyl-ACP substrates in lieu of, or in addition to, acting on fatty acyl-CoA substrates, to produce fatty alcohols. In some embodiments of this aspect, the FAR enzymes from as encompassed by the invention herein including but not limited to FAR enzymes from *Marinobacter* species, such as *Marinobacter* species *algicola* (DG893) and *Marinobacter aquaeolei*, and *Oceanobacter* species strain RED65 or functional fragments thereof can produce levels of fatty alcohols in the absence of, or in the presence of low levels of fatty acyl-CoA substrates, which were thought to be the main substrates of FAR enzymes that are comparable to the levels of fatty alcohols produced in the presence of normal levels of fatty acyl-CoA substrates. In further embodiments of this aspect, the invention relates to a recombinant host cell comprising a nucleic acid encoding a FAR enzyme according to the invention and an inactivated or silenced endogenous fatty acyl-ACP thioesterase gene, an inactivated or silenced endogenous fatty acyl-CoA synthetase gene or both. In some embodiments, the recombinant microorganisms provided herein above do not produce detectable levels of fatty acyl-CoA substrates and in other embodiments the recombinant microorganisms produce reduced levels of fatty acyl-CoA substrates as compared to wild-type cells.

In one preferred embodiment, fatty alcohols are produced by an acyl-CoA independent pathway comprising culturing a recombinant bacterial cells under suitable culture conditions, wherein the recombinant bacterial cell comprises a gene encoding a heterologous FAR polypeptide encompassed by the invention and wherein the recombinant bacterial cell comprises one or more endogenous polynucleotides that have been inactivated or silenced selected from a fadD gene, which codes for an acyl-CoA synthetase protein, a fadK gene, which codes for an endogenous short-chain acyl-CoA synthetase or both; allowing expression of the gene encoding the heterologous FAR enzyme and producing fatty alcohols by the conversion of fatty acyl-ACP substrates.

In certain embodiments, the recombinant host cell is an *E. coli* cell. In some embodiments of this aspect, the FAR enzymes are derived from *Marinobacter algicola* (DG893), *Marinobacter aquaeolei*, and *Oceanobacter* species strain RED65 or functional fragments thereof. In certain embodiments, the FAR enzyme for use in the methods disclosed herein has an amino acid that has an amino acid sequence that is at least about 75% identical, at least about 80% identical, such as at least about 85% identical, such as at least about 90% identical, such as at least about 91%, such as at least about 92%, such as at least about 93%, such as at least about 94%, such as at least about 95%, such as at least about 96%, such as at least about 97%, such as at least about 98%, such as at least about 99% identical to the sequence set forth in SEQ ID NO: 2, SEQ ID NO: 6, SEQ ID NO: 14, or functional fragments thereof.

Methods of Producing Fatty Alcohols and Compositions of Fatty Alcohols:

In various aspects of the present disclosure, fatty alcohols can be produced in cell-free systems. In certain embodiments, a FAR enzyme as described herein is provided with a substrate and all necessary cofactors to carry out the production of a fatty alcohol from a fatty acyl-thioesterase substrate. In certain aspects, fatty alcohols can be produced by recombinant microorganisms that express a heterologous FAR enzyme as described herein. In particular aspects, fatty alcohols can be produced by recombinant microorganisms that express a heterologous FAR enzyme and one or more proteins other than a FAR enzyme. In some embodiments, the fatty alcohols produced by the recombinant microorganisms are secreted into the nutrient medium. In other embodiments, the fatty alcohols produced by the recombinant microorganisms are extracted from the microorganisms.

In certain embodiments, the present disclosure relates to the use of a FAR enzyme as described herein, e.g., a FAR enzyme from a marine gamma proteobacterium, for producing a fatty alcohol composition in a cell-free system. In some embodiments, the FAR enzyme is provided with a substrate, e.g., a fatty acyl-thioester of the formula (I) and NAD(P)H under suitable conditions of temperature, pH, and ionic strength and time sufficient for the production of a fatty alcohol composition. In some embodiments, the FAR enzyme is provided with a composition of a fatty acid, Coenzyme A, ATP, NAD(P)H, and a fatty acyl-CoA synthase under suitable conditions of temperature, pH and ionic strength and time sufficient for production of the fatty acyl-CoA substrate of the FAR enzyme by the fatty acyl-CoA synthase and for production of a fatty alcohol composition from the fatty acyl-CoA substrate.

In certain embodiments of the present disclosure, a fatty alcohol composition is produced by a recombinant host cell comprising a heterologous gene encoding a FAR enzyme as described above, which is cultured in an aqueous nutrient medium comprising an assimilable source of carbon under conditions suitable for production of a fatty alcohol composition. In some embodiments, the fatty alcohol is produced by a recombinant host cell comprising a heterologous gene encoding a FAR enzyme as described above and the recombinant host cell comprises an inactivated or silenced gene selected from an acyl-ACP thioesterase and a fatty acyl-CoA synthetase.

In various embodiments, the recombinant host cell is a bacterium. In particular embodiments, the bacterium is *E. coli*. In other embodiments, the recombinant host cell is a yeast. In particular embodiments, the yeast is *S. cerevisiae*. In certain embodiments, the yeast is an oleaginous yeast. In certain particular embodiments, the oleaginous yeast is *Y. lipolytica*.

In various embodiments, a fatty alcohol composition is produced by a recombinant host cell comprising a heterologous gene encoding a FAR enzyme from a marine bacterium and which over expresses a gene encoding one or more proteins that increases the rate at which the recombinant host cell produces the acyl-thioester FAR substrate, e.g., the compound of formula (I) above. In some embodiments, the one or more over expressed genes encode a protein directly involved in fatty acid biosynthesis. In particular embodiments, the one or more over expressed genes encode a protein selected from a fatty acid synthase (FAS), an acyl-ACP thioesterase (TE), a fatty acyl-CoA synthase (FACS) and an acetyl-CoA carboxylase (ACC).

"Culturing" or "cultivation" refers to growing a population of microbial cells under suitable conditions in a liquid or solid medium. In particular embodiments, culturing refers to the fermentative bioconversion of a substrate to an end-product. Culturing media are well known and individual components of such culture media are available from commercial sources, e.g., under the Difco™ and BBL™ trademarks. In one non-limiting example, the aqueous nutrient medium is a "rich medium" comprising complex sources of nitrogen, salts, and carbon, such as YP medium, comprising 10 g/L of peptone and 10 g/L yeast extract of such a medium.

In other non-limiting embodiments, the aqueous nutrient medium comprises a mixture of Yeast Nitrogen Base (Difco) supplemented with an appropriate mixture of amino acids, e.g. SC medium. In particular aspects of this embodiment, the amino acid mixture lacks one or more amino acids, thereby imposing selective pressure for maintenance of an expression vector within the recombinant host cell.

Fermentation of the recombinant host cell comprising a heterologous FAR gene for production of fatty alcohols is carried out under suitable conditions and for a time sufficient for production of fatty alcohols. Conditions for the culture and production of cells, including bacterial and yeast cells, are readily available. Cell culture media in general are set forth in Atlas and Parks (eds.) *The Handbook of Microbiological Media* (1993) CRC Press, Boca Raton, Fla., which is incorporated herein by reference. Additional information for cell culture is found in available commercial literature such as the *Life Science Research Cell Culture Catalogue* (1998) from Sigma-Aldrich, Inc (St Louis, Mo.) ("Sigma-LSRCCC") and, for example, *The Plant Culture Catalogue and supplement* (1997) also from Sigma-Aldrich, Inc (St Louis, Mo.) ("Sigma-PCCS"), all of which are incorporated herein by reference.

In some embodiments, cells expressing the heterologous FAR genes as described herein are grown under batch or continuous fermentations conditions. Classical batch fermentation is a closed system, wherein the compositions of the medium is set at the beginning of the fermentation and is not subject to artificial alternations during the fermentation. A variation of the batch system is a fed-batch fermentation which also finds use in the present invention. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth. Continuous fermentation systems strive to maintain steady state growth conditions. Methods for modulating nutrients and growth factors for continuous fermentation processes as well as techniques for maximizing the rate of product formation are well known in the art of industrial microbiology.

In some embodiments, fermentations are carried out a temperature within the range of from about 10° C. to about 60° C., from about 15° C. to about 50° C., from about 20° C. to about 45° C., and from about 25° C. to about 40° C. In a particular aspect, the fermentation is carried out at a temperature of from about 28° C. and also from about 30° C. In other embodiments, the fermentation is carried out for a period of time within the range of from about 8 hours to 240 hours, from about 8 hours to about 168 hours, from about 16 hours to about 144 hours, from about 16 hours to about 120 hours, or from about 24 hours to about 72 hours. It will be understood that, in certain embodiments where thermostable host cells are used, fermentations may be carried out at higher temperatures. In other embodiments, the fermentation will be carried out at a pH in the range of 4 to 8, in the range of 4.5 to 7.5, in the range of 5 to 7, and also in the range of 5.5 to 6.5.

Carbon sources useful in the aqueous fermentation medium or broth of the disclosed process in which the recombinant microorganisms are grown are those assimilable by the recombinant host strain. Assimilable carbon sources are available in many forms and include renewable carbon sources and the cellulosic and starch feedstock substrates obtained there from. Such examples include for example monosaccharides, disaccharides, oligosaccharides, saturated and unsaturated fatty acids, succinate, acetate and mixtures thereof. Further carbon sources include, without limitation, glucose, galactose, sucrose, xylose, fructose, glycerol, arabinose, mannose, raffinose, lactose, maltose, and mixtures thereof. In some embodiments, the term "fermentable sugars" is used interchangeably with the term "assimilable carbon source". In one aspect, fermentation is carried out with a mixture of glucose and galactose as the assimilable carbon source. In another aspect, fermentation is carried out with glucose alone to accumulate biomass, after which the glucose is substantially removed and replaced with an inducer, e.g., galactose for induction of expression of one or more heterologous genes involved in fatty alcohol production. In still another aspect, fermentation is carried out with an assimilable carbon source that does not mediate glucose repression, e.g., raffinose, to accumulate biomass, after which the inducer, e.g., galactose, is added to induce expression of one or more heterologous genes involved in fatty alcohol production. In some preferred embodiments, the assimilable carbon source is from cellulosic and starch feedstock derived from but not limited to, wood, wood pulp, paper pulp, grain, corn stover, corn fiber, rice, paper and pulp processing waste, woody or herbaceous plants, fruit or vegetable pulp, distillers grain, grasses, rice hulls, wheat straw, cotton, hemp, flax, sisal, corn cobs, sugar cane bagasse, switch grass and mixtures thereof.

In various embodiments, the present disclosure relates to methods of producing a fatty alcohol composition comprising culturing a recombinant host cell comprising a gene expressing a heterologous FAR enzyme in an aqueous nutrient medium comprising an assimilable source of carbon under conditions in which a fatty alcohol composition of produced, and isolating the fatty alcohols.

In certain embodiments of the disclosed processes, at least 10%, such as at least 20%, such as at least 25%, such as at least 30%, such as at least 40%, such as at least 50%, such as at least 60%, such as at least 70%, such as at least 80%, such as at least 90% of the fatty alcohols produced by the methods described herein are secreted into the culture medium. In particular embodiments, when the recombinant microorganism is *E. coli, Yarrowia* (e.g., *Y. lipolytica*) or *Saccharomyces* (e.g., *S. cerevisiae*) at least 25% and also at least 50% of the fatty alcohols produced by the methods encompassed by the invention will be secreted into the culture medium.

In various embodiments, fatty alcohols produced by the methods of the invention are further recovered or isolated. Recovery or isolating the produced fatty alcohols refers to substantially separating the fatty alcohols from other components of the culture medium or fermentation process. Recovery or isolation may be by solvent extraction of the aqueous nutrient medium with a suitable water immiscible solvent. Extraction may occur simultaneously with fatty alcohol production and extraction may be continuous. Phase separation followed by solvent removal provides the fatty alcohol which may then be further purified and fractionated using methods and equipment known in the art. In other aspects of the disclosure, the secreted fatty alcohols coalesce to form a water immiscible phase that can be directly separated from the aqueous nutrient medium either during the fermentation or after its completion.

In some embodiments, less than 60%, less than about 50%, such as less than about 40%, such as less than about 30%, such as less than about 20%, such as less than about 10% of the fatty alcohols produced by the methods described herein are secreted from the recombinant host cells. In some embodiments, at least about 30%, such as at least about 40%, such as at least 45%, such as at least about 50%, such as at least about 60%, such as at least about 65%, such as at least about than 70%, such as at least about 75%, such a least about 80%, such as at least about 85%, such as at least about 90% of the fatty alcohols produced by the methods described herein are secreted from the recombinant host cells. In certain embodiments, fatty alcohols are isolated by separating the cells from the aqueous nutrient medium, for example by centrifugation, resuspension and extraction of the fatty alcohols from the recombinant host cells using an organic solvent or solvent mixture. Suitable protocols for recovering fatty alcohols from recombinant host cells and/or culture medium are known to the skilled artisan. In some embodiments, fatty alcohols may be recovered by first lysing the cells to release the fatty alcohols and then extracting the fatty alcohol from the lysate using conventional means. Reference is also made to Yeast Protocols Handbook, (2009) Clontech Laboratories, Inc. A Takara Bio Company, Mt. View Calif. 94043 and PNAS 2003 Vol. 100, 16:9156-9161.

In some embodiments, the present disclosure relates to fatty alcohol compositions produced by recombinant host cells comprising a gene encoding any one of the FAR enzymes as encompassed by the invention and described hereinabove. In some particular embodiments, the FAR enzyme is derived from a *Marinobacter* or *Oceanobacter* species of gammaproteobacterium. In some embodiments, the FAR enzyme is derived from a *Marinobacter* species selected from, but not limited to, *M. algicola* DG893, *M. alkaliphihis, M. aquaeoli, M. arcticus, M. bryozoorum, M. daepoensis, M. excellens, M. flavimaris, M. guadonensis, M. hydrocarbonoclasticus, M. koreensis, M. lipolyticus, M. litoralis, M. lutaoensis, M. maritimus, M. sediminum, M. squalenivirans* and *M. vinifirmus*. In various embodiments, the FAR enzyme is obtained from a marine bacterium selected from the group consisting of *Meptuniibacter caesariensis* species strain MED92, *Reinekea* sp. strain MED297, *Marinomonas* sp. strain MED121, unnamed gammaproteobacterium strain HTCC2207 and *Marinobacter* sp. strain ELB17. In some specific embodiments, the FAR enzyme is derived from or endogenous to an *Oceanobacter* species selected from, but not limited to, *Oceanobacter kriegii* and *Oceanobacter* strain WH099.

In various embodiments, the compositions produced by the methods described herein comprise both saturated and unsaturated fatty alcohols. In certain embodiments, the unsaturated fatty alcohols are monounsaturated fatty alcohols. In some embodiments, the fatty alcohol compositions comprise both saturated and unsaturated fatty alcohols, and the amount of unsaturated fatty alcohols is less than about 30%, such as less than about 20%, such as less than about 10%, such as less than about 5%, such as less than about 1% of the fatty alcohols present in the composition. In other embodiments, the fatty alcohol compositions comprise both saturated and unsaturated fatty alcohols, and the amount of saturated fatty alcohols is less than about 30%, such as less than about 20%, such as less than about 10%, such as less than about 5%, such as less than about 1% of the fatty alcohols present in the composition.

In some typical embodiments, the fatty alcohol compositions produced by the methods described herein comprise one or more alcohols selected from the group consisting of 1-octanol (C8:0), 1-decanol (C10:0), 1-dodecanol (C12:0), 1-tetradecanol (C14:0), 1-hexadecanol (C16:0), 1-octadecanol (C18:0), 1-icosanol (C20:0), 1-docosanol, 1-tetracosanol, cis $\Delta^9$-1-hexadecanol, and cis $\Delta^{11}$-1-octadecanol.

In typical embodiments, C8 to C20 fatty alcohols comprise at least about 80%, such as at least about 85%, such as at least about 90%, such as at least about 92%, such as at least about 95%, such as at least about 97%, such as at least about 99% by weight of the total isolated fatty alcohols. In certain embodiments, C10 to C18 fatty alcohols comprise about 80%, such as at least about 85%, such as at least about 90%, such as at least about 92%, such as at least about 95%, such as at least about 97%, such as at least about 99% by weight of the total isolated fatty alcohols. In certain embodiments, C14 to C18 fatty alcohols comprise about 80%, such as at least about 85%, such as at least about 90%, such as at least about 92%, such as at least about 95%, such as at least about 97%, such as at least about 99% by weight of the total isolated fatty alcohols. It is understood that a reference to a "Cx fatty alcohol" includes both saturated and unsaturated fatty alcohols having "x" carbon atoms.

In various embodiments, C16 to C18 fatty alcohols comprise at least about 80%, such as at least about 85%, such as at least about 90%, such as at least about 91%, such as at least about 92%, such as at least about 93%, such as at least about 94%, such as at least about 95%, such as at least about 96%, such as at least about 97%, such as at least about 98%, such as at least about 99% by weight of the total isolated fatty alcohols. In certain embodiments, the C16 to C18 fatty alcohols are saturated. In other embodiments the C16 to C18 fatty alcohols are a mixture of saturated and unsaturated fatty alcohols.

In certain embodiments, the amount of fatty alcohols produced by the methods described herein comprise saturated and/or unsaturated C8 to C24 alcohols produced by a recombinant host cell comprising a heterologous gene encoding a FAR as described herein in a range of about 10 mg/L to about 50 g/L of aqueous nutrient medium, such as in a range of about 10 mg/L to about 5 g/L, such as in a range of about 10 mg/L to about 2 g/L of medium by routine modification of culturing conditions. In particular embodiments, the amount of fatty alcohols produced by the methods described herein is at least about 0.5 g/L, such as at least about 1 g/L, such as at least about 1.5 g/L, such as at least about 2.0 g/L, such as at least about 2.5 g/L, such as at least about 3 g/L, such as at least about 3.5 g/L, such as at least about 4 g/L, such as at least about 4.5 g/L, such as at least about 5 g/L, such as at least about 10 g/L of medium. In various embodiments, the amount of fatty alcohols produced by the methods described herein is at least about 20 g/L, such as at least about 30 g/L, such as at least about 40 g/L, such as at least about 50 g/L of medium. In particular embodiments, the recombinant microorganism comprising a gene encoding FAR enzyme as encompassed by the invention is E. coli, Yarrowia lipolytica or Saccharomyces cerevisiae and the amount of fatty alcohol produced is at least 1.0 g/L, at least 5.0 g/L, at least 10 g/L, at least 15 g/L, at least 20 g/L, at least 25 g/L and at least 30 g/L of medium.

In some embodiments, the amount of fatty alcohols produced by the methods described herein is in the range of about 100 mg/g to about 5 g/g of dry cell weight. In other embodiments, the amount of fatty alcohols produced by the methods described herein is in the range of about 1 g/g to about 4 g/g of dry cell weight, such as in the range of about 2 g/g to about 3 g/g of dry cell weight by routine modification of culturing conditions.

In certain embodiments, the amount of fatty alcohols produced by the methods described herein is in the range of about 10% to about 20% of dry cell weight, such as in the range of about 20% to about 30% of dry cell weight, such as in the range of about 30% to about 40% of dry cell weight, such as in the range of about 40% to about 50% of dry cell weight, such as in the in range of about 50% to about 60% of dry cell weight, such as in the range of about 60% to about 70% of dry cell weight, such as in the range of about 70% to about 80% of dry cell weight by routine modification of culturing conditions. Fatty alcohol compositions produced by the methods described herein may also include fatty acid derived components, such as but not limited to esters (e.g. acetate and waxes) and fatty acids.

Methods of Producing Alkane and/or Alkene Compositions:

In various embodiments, the fatty alcohol compositions produced by the methods described herein are subjected to reduction to produce alkanes and/or alkenes having the same carbon chain length as the fatty alcohol starting materials. Without being bound by any particular theory, the hydroxyl group of an alcohol is a poor leaving group, and therefore, in principle a chemical moiety that binds to the oxygen atom of the hydroxyl group to make it a better leaving group can be used to reduce the fatty alcohols described herein.

Any method known in the art can be used to reduce the fatty alcohols present in the compositions described herein. In some embodiments, reduction of fatty alcohols can be carried out chemically, for example, by a Barton deoxygenation (or Barton-McCombie deoxygenation), a two-step reaction in which the alcohol is first converted to a methyl xanthate or thioimidazoyl carbamate, and the xanthate or thioimidazoyl carbamate is reduced with a tin hydride or trialkylsilane reagent under radical conditions to produce the alkane and/or alkene. See J. J. Li, C. Limberakis, D. A. Pflum *Modern Organic Synthesis in the Laboratory* (Oxford University Press, 2007) at pp. 81-83.

In some embodiments, reduction of fatty alcohols to the corresponding alkanes and/or alkenes can be accomplished using a microorganism that has a biosynthetic pathway for reducing fatty alcohols. In certain embodiments, the microorganism is a bacterium. In specific embodiments, the bacterium is *Vibrio furnissii* strain M1. In some embodiments, the fatty alcohol compositions produced by the methods described herein are contacted with the appropriate microorganism for reduction to alkanes and/or alkenes. In other embodiments, the fatty alcohol compositions produced by the methods described herein are contacted with membrane fractions from the appropriate microorganism so that the reduction is carried out in a cell free system. See e.g., Park (2005) *J. Bacteriol.* 187(4): 1426-1429.

In certain embodiments, alkanes and/or alkenes produced by the reduction of fatty alcohols described herein are isolated from the reaction mixture and unreduced fatty alcohol starting materials to produce a composition that comprises substantially all alkanes and/or alkenes. In some embodiments, the alkanes and/or alkenes produced by the reduction of fatty alcohols described herein and the unreacted fatty alcohol starting materials are isolated from the reaction mixture to produce a composition comprising alkanes and/or alkenes and fatty alcohols.

In certain embodiments, the resulting compositions comprise at least about 60% alkanes and/or alkenes, such as at least about 70% alkanes and/or alkenes, such as at least about 80% alkanes and/or alkenes, such as at least about 85% alkanes and/or alkenes, such as at least about 90% alkanes and/or alkenes, such as at least about 92% alkanes and/or alkenes, such as at least about 95% alkanes and/or alkenes, such as at least about 96% alkanes and/or alkenes, such as at least about 97% alkanes and/or alkenes, such as at least about 98% alkanes and/or alkenes, such as at least about 99% alkanes and/or alkenes by weight of the composition after reduction.

In other embodiments, the resulting compositions comprise at least about 10% alkanes and/or alkenes, such as at least about 20% alkanes and/or alkenes, such as at least about 30% alkanes and/or alkenes, such as at least about 40% alkanes and/or alkenes, such as at least about 50% alkanes and/or alkenes by weight of the composition after reduction.

In some typical embodiments, the compositions produced by the methods described herein comprise one or more alkanes selected from the group consisting of octane, decane, dodecane, tetradecane, hexadecane, octadecane, icosane, docosane, and tetracosane. In other typical embodiments, the compositions produced by the methods described herein comprise one or more alkenes selected from the group consisting of octane, decene, dodecene, tetradecene, hexadecene, octadecene, icosene, docosene, and tetracosene.

In typical embodiments, C8 to C20 alkanes and/or alkenes comprise at least about 80%, such as at least about 85%, such as at least about 90%, such as at least about 92%, such as at least about 95%, such as at least about 97%, such as at least about 99% by weight of the total alkanes and/or alkenes in the composition. In certain embodiments, C10 to C18 alkanes and/or alkenes comprise about 80%, such as at least about 85%, such as at least about 90%, such as at least about 92%, such as at least about 95%, such as at least about 97%, such as at least about 99% by weight of the total alkanes and/or alkenes in the composition.

In certain embodiments, alkanes and/or alkenes having particular carbon chain lengths can be isolated from longer and/or shorter alkanes and/or alkenes, for example by HPLC. In certain embodiments, alkane and/or alkene compositions that are suitable, e.g., for use in jet fuels, comprise C10 to C14 alkanes and/or alkenes. In other embodiments, alkane and/or alkene compositions that are suitable, e.g., for use in diesel fuels comprise alkanes and/or alkenes that have 16 or more carbons (e.g., C16 or longer-chain alkanes and/or alkenes).

Fuel Compositions:

In certain embodiments, the fatty alcohol compositions described herein and compounds derived there from can be used as components of fuel compositions. In certain embodiments, the fatty alcohol compositions produced by the methods described above can be used directly in fuel compositions. In various embodiments, the fatty alcohols can be reacted with a carboxylic acid to produce acid esters. In particular embodiments, the acid esters are used as components of biodiesel fuel compositions. In other embodiments, the fatty alcohols are reacted with a reducing agent to produce alkanes and/or alkenes. In some embodiments, alkanes and/or alkenes derived from the fatty alcohol compositions are used as components of jet fuel compositions. In other embodiments, alkanes and/or alkenes derived from fatty alcohol compositions are used as components of rocket fuel. In still other embodiments, alkanes and/or alkenes derived from the fatty alcohol compositions are used as components in petrodiesel-like fuel compositions.

In some embodiments, the fuel compositions comprise an alkane and/or alkene derived from the fatty alcohol compositions described herein. In certain embodiments, the alkanes and/or alkenes have from 6 to 16 carbons and the fuel composition is a kerosene-like fuel composition. In various embodiments, the kerosene-like fuel compositions are included in jet fuel compositions. In particular embodiments, the kerosene-like fuel compositions are included in various grades of jet fuel, including but not limited to, grades Avtur, Jet A, Jet A-1, Jet B, JP-4, JP-5, JP-7 and JP-8. In other embodiments, the kerosene-like fuel compositions are included in fuel compositions for heating. In still other embodiments, the kerosene-like fuel compositions derived from the fatty alcohol compositions described above are burned with liquid oxygen to provide rocket fuel. In particular embodiments, the kerosene-like fuel compositions are used in RP-1 rocket fuel.

In some embodiments, the alkanes and/or alkenes derived from the fatty alcohol compositions described herein are used in fuel compositions that are similar to petrodeisel fuel compositions, e.g., that contain saturated and aromatic hydrocarbons. In certain embodiments, the fuel compositions comprise only alkanes and/or alkenes derived from the fatty alcohol compositions described herein. In other embodiments, the fuel compositions comprise alkanes and/or alkenes derived from the fatty alcohol compositions described herein mixed with other components, such as petrodiesel fuel.

In certain embodiments, the fatty alcohols are further processed with a carboxylic acid to form acid esters. Esterification reactions of fatty alcohols are well-known in the art. In certain embodiments, the transesterification reaction is carried out in the presence of a strong catalyst, e.g., a strong alkaline such as sodium hydroxide. In other embodiments, the reaction is carried out enzymatically using an enzyme that catalyzes the conversion of fatty alcohols to acid esters, such as lipoprotein lipase. See, e.g., Tsujita et al. (1999) *J. Biochem.* 126(6):1074-1079. In various embodiments, the acid esters are used as biodiesel fuel without being mixed with other components. In certain embodiments, the fatty acid esters are mixed with other components, such as petrodiesel fuel.

In certain embodiments, fatty alcohols, or acid esters or alkanes and/or alkenes derived there from, are combined with other fuels or fuel additives to produce compositions having desired properties for their intended use. Exemplary fuels and fuel additives for particular applications are well-known in the art. Exemplary fuels which can be combined with the compositions described herein include, but are not limited to, traditional fuels such as ethanol and petroleum-based fuels. Exemplary fuel additives which can be combined with the compositions described herein include, but are not limited to, cloud point lowering additives, surfactants, antioxidants, metal deactivators, corrosion inhibitors, anti-icing additives, anti-wear additives, deposit-modifying additives and octane enhancers.

EXAMPLES

Various features and embodiments of the disclosure are provided in the following representative examples of the disclosure are provided in the following representative examples, which are intended to illustrative and not limiting.

Example 1

Gene Acquisition

Wild-type *B. mori*, *M. algicola* DG893, and *Oceanobacter* sp. RED65 fatty acyl reductase (FAR) genes were designed for expression in *E. coli*, *S. cerevisiae*, and *Y. lipolytica* based on the reported amino acid sequences (*B. mori* FAR: Moto et al. (2003) *Proc. Nat'l Acad. Sci.* 100:9156-61; Reiser (1997) GenBank accession number BAC79425.1; *M. algicola* DG893 FAR: GenBank genome accession number NZ_ABCP01000001.1; and *Oceanobacter* sp RED65 FAR: GenBank genome accession number NZ_AAQH01000001.1). *M. aquaeolei* FAR gene having GenBank accession number YP_959486 was codon optimized for expression in *E. coli*. Codon optimization was performed using an algorithm as described in Example 1 of WO2008/042876, incorporated herein by reference in its entirety. Input codon usage information for the algorithm was either a hybrid of *E. coli*, *S. cerevisiae*, and *Y. lipolytica* usages, or the codon usage for the individual organisms. The genes were synthesized by Genscript (Piscataway, N.J.) with flanking restriction sites for cloning into *E. coli* vector pCK 110900 described in US Patent Publication No. 2006/0195947. Nucleotide sequences for SfiI restriction sites were added to the 5' end and the 3' end of the gene as well as to the t7g10 RBS in front of the ATG start codon.

(SEQ ID NO: 15)
5' ACAATCTGGATCCGGCCAGCCTGGCCATAAGGAGATATACAT
and (SEQ ID NO: 16)
3' TAATGAGGCCAAACTGGCCGTCGACACCAGTATG.

The genes were provided in the vector pUC57 by Genscript (Piscataway, N.J.) and the sequences verified by DNA sequencing. The sequences of the codon optimized genes for recombinant host cells for M. algicola DG893 FAR, M. aquaeolei, Oceanobacter sp. RED65 FAR, and B. mori FAR are set forth respectively in SEQ ID NOs: 1 and 3 for FAR_Maa, SEQ ID NO: 13 for FAR_Maq, SEQ ID NOs: 5 and 7 for FAR_Osc and SEQ ID NO: 11 for B. mori and the corresponding polypeptide sequences are set forth respectively in SEQ ID NOs: 2 and 4 for FAR_Maa, SEQ ID NO: 14 for FAR_Maq, SEQ ID NOs: 6 and 8 for FAR_Osc and SEQ ID NO: 12 for B. mori.

Example 2

Expression and Activity of FARs in E. coli a. Construction of Vectors to Express FARs in E. coli The FAR genes were cloned into the vector pCK110900 (shown in FIG. 3 of US Patent Publication No. 2006/0195947) under the control of a lac promoter using the Sfi I restriction sites. The expression vector also contained the P15a origin of replication and the chloramphenicol resistance gene. The resulting plasmids were introduced into E. coli BW25113 (ΔfadE) (Baba et al., Molecular Systems Biology, 2006 doi:10,1038/msb4100050, Article Number: 2006.0008) using routine transformation methods.

b. In Vivo Activity of FARs in Recombinant E. coli Using Shake Flasks

Recombinant E. coli host strains comprising a plasmid containing a heterologous gene encoding either the B. mori, M. algicola DG893, M. aquaeolei or Oceanobacter sp. RED65 fatty acyl-CoA reductase, were grown in Luria Bertani Broth (LB) medium supplemented with 1% glucose and 30 μg/mL chloramphenicol (CAM), for approximately 16-18 hours (overnight) at 30° C., 200 rpm. A 5% inoculum was used to initiate fresh 50 mL 2xYT Broth culture supplemented with 30 μg/mL CAM and 0-0.4% glucose. The culture was incubated in a shaker for 2.5 hours at 30° C. and 200 rpm to an $OD_{600}$ of about 0.6 to about 0.8, at which point expression of the heterologous FAR was induced with isopropyl-β-D-thiogalactoside (IPTG) (1 mM final concentration). Incubation was continued for about 16 hours (overnight) under the same conditions. Cells were collected by centrifugation for 10 minutes at 6000 rpm in F15B-8×50C rotor. The cell pellets were resuspended in 0.5 mL of 6.7% $Na_2SO_4$ and then extracted with 1 mL of isopropanol:methyl t-butyl ether (4/6 ratio) for 2 hrs. The extract was centrifuged and analyzed either directly by GC-FID or GC-MS or derivatized with BSTFA before analysis. For derivatization, a 400 μL sample was taken off the top organic layer, evaporated under a nitrogen stream and the residue was derivatized with 100 μL N,O-Bis(trimethylsilyl)trifluoroacetamide) (BSTFA) at 37° C. for 1 hour, and then diluted with 100 μL of heptanes before analysis by GC-FID or GC-MS. 0.5 mL of the culture medium (after removal of cells by centrifugation) was also extracted with 1 mL methyl t-butyl ether for 1 hr. The organic phase was either analyzed directly by GC-FID or GC-MS or derivatized with BSTFA as described above before analysis. In addition, 0.5 mL of the cell culture (before removal of cells by centrifugation) was directly extracted with 1 mL of isopropanol:hexane (4:6 ratio) for 2 hrs. The organic phase was either analyzed directly by GC-FID or GC-MS or derivatized with BSTFA as described above before analysis.

A 1 μL sample was analyzed by GC-FID with the split ratio 1:10 using the following conditions: GC-6890N from Agilent Technologies equipped with FID detector and HP-5 column (length 30 m, I.D. 0.32 mm, film 0.25 μm). GC method: start at 100° C., increase the temperature with a rate of 25° C./min to 246° C. and hold for 1.96 min. Total run time, 7.8 min. Under the above GC conditions the approximate retention times (min) of produced fatty alcohols and acids are as follows: 5.08, C14:0-OH; 5.40; C14:0-OOH; 5.74, C16:1-OH, 5.93; C16:0-OH, 6.11; C16:0-OOMe (internal standard); 6.16, C16:1-OOH, 6.29; C16:0-OOH, 6.80; C18:1-OH, 6.90; C18:0-OH, 7.3; C18:0- and C18:1-OOH. Under the conditions tested, expression of the B. mori, M. algicola DG893 and Oceanobacter sp. RED65, FARs in E. coli BW25113 ΔfadE resulted production of fatty alcohols (see Table 2). Identification of individual fatty alcohol was done by comparison to commercial standards (Sigma Chemical Company, 6050 Spruce St. Louis, Mo. 63103). In addition the total production of fatty alcohols by FAR_Maq was similar to that obtained from FAR_Maa (M. algicola DG893) and produced fatty alcohols include C14:0 (2.5%), C16:1 (10%), C16:0 (34%), C18:1 (53%) and C18:0 (0.5%).

TABLE 2

Fatty alcohol profile exhibited by recombinant E. coli BW25113 ΔfadE host cells over expressing heterologous FAR genes

| FAR Enzyme | Fatty alcohol composition[a] | | | | | | Total[b] (mg/L) | Secreted[b] (mg/L) |
|---|---|---|---|---|---|---|---|---|
| | C12:0 | C14:0 | C16:1 | C16:0 | C18:1 | C18:0 | | |
| B. mori | <10 | <10 | <10 | >40 | 10-20 | <10 | 2 | ND |
| Oceanobacter RED65 | ND | 3 | 10 | 33 | 54 | ND | 320 | 220 |
| M. algicola DG893 | ND | 8 | 30 | 30 | 32 | ND | 820 | 720 |

[a]The relative amounts of each fatty alcohol component are expressed as a % of the total fatty alcohols detected via GC-FID. Fatty alcohols include: C12:0 (1-dodecanol), no C12:1 (1-dodecenol) was detected, C14:0 (1-tetradecanol), no C14:1 (1-tetradecenol) was detected, C16:1 (cis $\Delta^9$-1-hexadecenol), C16:0 (1-hexahecanol), C18:1 (cis $\Delta^{11}$-1-octadecenol), 18:0 (1-octadecanol).
ND: not detected.
[b]Enzyme productivity was estimated using both internal and external standards.

c. In Vivo Activity of FARs in Recombinant *E. coli* Using Fermentors

In an aerated, agitated stirred tank fermentor, 1.0 L of growth medium containing 11.28 g/L 5×M9 minimal salts (BD, Franklin Lakes, N.J.); 2 g/L yeast extract (BD, Franklin Lakes, N.J.); 3 g/L glucose (Sigma Chemical Co., St. Louis, Mo.); 2 mM MgSO$_4$ (Sigma Chemical Co., St. Louis, Mo.); 0.1 mM CaCl$_2$ (Sigma Chemical Co., St. Louis, Mo.); and 30 µg/ml chloramphenicol (Sigma Chemical Co., St. Louis, Mo.) was brought to a temperature of 30° C. The fermentor was inoculated with a late exponential culture of *E. coli* BW25113 ΔfadE equipped with plasmid containing *M. algicola* DG893 (as described in Example 2b) to a starting optical density at 600 nm (OD$_{600}$) of 0.8 to 1.0. The inoculum was grown in a shake flask containing TB (BD, Franklin Lakes, N.J.); 0.4% glycerol (Sigma Chemical Co., St. Louis, Mo.), and 30 µg/ml chloramphenicol (Sigma Chemical Co., St. Louis, Mo.) at 30° C. and 250 rpm until OD600 reached around 5.0. The fermentor was agitated at 400-1000 rpm and air supplied at 1.0 L/min to maintain a minimum dissolved oxygen level of 30% of saturation. The pH of the culture was controlled at 7.0 initially by addition of mixture of 14% v/v ammonium hydroxide and 10% w/v sodium hydroxide. The base for pH control was switched to 20% w/v sodium hydroxide when ammonium concentration in the broth reached 1.5-2.0 g/L. After the culture reached an OD$_{600}$ of 5.0, the expression of *M. algicola* DG893 FAR was induced by addition of isopropyl-β-D-thiogalactoside (IPTG) (Sigma Chemical Corp., St. Louis, Mo.) to a final concentration of 1 mM. Growth of the culture and production of fatty alcohol were maintained by addition of a feed solution containing 500 g/L glucose. Addition of glucose (6 g/L per pulse) was triggered whenever pH reached 7.2. Culture was then grown for another 135-140 hours at 30° C. 3 g/L yeast extract shots were added at 55 and 95 hours. Samples were taken at different time points for analysis. Extraction and quantification of fatty alcohols were performed as described in Example 2b. Under the conditions tested, total production and secretion of fatty alcohols were estimated to be ~12-15 and 9-13 g/L, respectively.

Example 3

Expression and Activity of FAR Enzymes in Various *E. coli* Strains a. Construction of Vectors to Express FARs in Various *E. coli* Strains The FAR genes were cloned into the vector pCK110900-I (shown in FIG. 3 of U.S. Patent Publication No. 2006/0195947) under the control of a lac promoter as described above. The resulting plasmids were introduced into *E. coli* BW25113 parent and knock-out strains (ΔfadE and ΔfadD, ΔfadK) derived from BW25113 (Baba et al., Molecular Systems Biology (2006) doi:10.1038/msb4100050, Article No. 2006.0008; Morgan-Kiss et al., J. Biol. Chem. (2004), 279: 37324-37333 and Campbell, et al., Molecular Microbiology (2003), 47(3): 793-805) by routine transformation methods.

b. In Vivo Activity of FARs in Various Recombinant *E. coli* Strains Using Shake Flasks Recombinant *E. coli* BW25113 strains (parent, ΔfadE, ΔfadD, and ΔfadK knock-outs) comprising a plasmid containing a heterologous gene encoding either *M. algicola* DG893 or *Oceanobacter* sp. RED65 fatty acyl reductase (FAR), were grown on Luria Bertani (LB) medium supplements with 1% glucose and 30 µg/ml chloramphenicol (CAM) for approximately 16-18 hours (overnight) at 30° C.,
200 rpm. A 5% inoculums was used to initiate fresh 50 mL LB culture supplemented with 30 µg/mL CAM. The culture was incubated for 2.5 hrs at 30° C. and 200 rpm to an OD600 of 0.6-0.8, at which point expression of the heterologous FAR gene was induced with isopropyl-β-D-thiogalactoside (IPTG) (1 mM final concentration). Incubation was continued for about 24 hours under the same conditions. Extraction and quantitation of fatty alcohols were performed as described in Example 2b except the use of following GC method: start at 80° C. for 3 mins, increase the temperature at a rate of 50° C./min to 200° C., then increase the temperature at a rate of 10° C./min to 270° C. and finally, increase at 20° C./min to 300° C. and hold for 5 min (total rum time 18.8 min). Under the above GC conditions the approximate retention times (mins) of produced fatty alcohols and acids were as follows: 6.90, C12:0-OH; 8.04, C14:0-OH; 8.42, d27-C14:0-OOH (internal standard); 8.53, C14:0-OOH; 9.11, C16:1-OH; 9.23, C16:0-OH; 9.68, C16:1-OOH, 9.80; C16:0-OOH; 10; 46, C18:1-OH; 10.57, C18:0-OH; 11.10, C18:1-OOH, and 11.25, C18:0-OOH. Identification of individual fatty alcohol was done by comparison to commercial standards (Sigma Chemical Company, St Louis, Mo. 63103). Under the conditions tested, expression of the *M. algicola* DG893 and *Oceanobacter* sp. RED65 FAR in *E. coli* BW25113 and the corresponding ΔfadD, ΔfadE and ΔfadK strains resulted in production of fatty alcohols (Tables 3a and 3b). Typical shake flask titer for *E. coli* BW25113 expressing *M. algicola* DG893 and *Oceanobacter* sp. RED65 FARs was 100-200 mg/L. Since both FARs are able to produce significant amounts of fatty alcohols in the absence of the fadD and fadK acyl-CoA synthetases in *E. coli*, these FARs are able to reduce non acyl-CoA substrates.

TABLE 3A

Fatty alcohol profile exhibited by recombinant *E.coli* host cells expressing a heterologous *M. algicola* FAR gene

| Recombinant *E.coli* cells | Deleted protein | Relative production of fatty alcohols[a] |
|---|---|---|
| BW25113 | — | 1.0 |
| BW25113 ΔfadE | Acyl-CoA dehydrogenase | 1.0 |
| BW25113 ΔfadD | Acyl-CoA synthetase | 0.78 |
| BW25113 ΔfadKlydiD | Short chain acyl-CoA synthetase, anaerobic | 0.64[b] |

[a]Fatty alcohols include: 15-17% C14:0 (1-tetradecanol), approximately 38% C16:1 (cis Δ$^9$-1-hexadeconal), 23-24% C16:0 (1-hexacecanol), 21-22% C18:1 (cis Δ$^{11}$-1-octadeconal), 0-1% C18:0 (1-octadecanol).
[b]Data obtained from evaluation of strains in microtiter plates.

TABLE 3B

Fatty alcohol profile exhibited by recombinant *E.coli* host cells expressing a heterologous *Oceanobacter* sp. RED65 FAR

| Recombinant *E.coli* cells | Deleted protein | Relative production of fatty alcohols[a] |
|---|---|---|
| BW25113 | — | 1.0 |
| BW25113 ΔfadE | Acyl-CoA dehydrogenase | 0.78 |
| BW25113 ΔfadD | Acyl-CoA synthetase | 0.60 |

[a]Fatty alcohols include: 0-2% C14:0 (1-tetradecanol), 2-10% C16:1 (cis Δ$^9$-1-hexadeconal), 32-36% C16:0 (1-hexacecanol), 56-62% C18:1 (cis Δ$^{11}$-1-octadeconal), 0-1% C18:0 (1-octadecanol).

c. Extraction and Quantitation of acyl-CoAs from *E. coli* Strains

Strains were grown as described above in Example 3b. 10 OD$_{600}$ units of cells were resuspended in 0.6 ml of ice-cold freshly made extraction buffer (100 mM $KH_2PO_4$, pH 4.9: isopropanol, 1:1), containing 200 ng/mL C17:0-CoA (heptadecanoyl-CoA) as an internal standard, and 0.6 ml of acetonitrile. The cell suspension was vortexed for 5 minutes and centrifuged at 4° C. and 14,000 rpm for 20 minutes. The supernatant was collected and evaporated under a nitrogen stream. The dry residue was resuspended in 200 µl of isopropanol/1 mM acetic acid (4:1) and centrifuged as described above. Supernatant was transferred into a glass vial, and 10 µl was injected into an LC-MS system (AB Sciex 5500 QTRAP) equipped with a Zorbax Extend C18, 4.6 mm×50 mm, 18 µm analytical column. HPLC separation was conducted using a binary gradient with 10% acetonitrile/90% water containing 0.1% $NH_4OH$ (A) and acetonitrile containing 0.1% $NH_4OH$ (B) at flow rate 0.5 mL/min. The chromatographic conditions were as follows: 0-1 min 5% solvent B, 1-7 min linear gradient to 95% solvent B, 7-9 min 95% solvent B, The post equilibrium time was 2.5 min. Total run time was 11.5 minutes. LC-MS/MS was performed in a negative mode using parameters described in Table 4. All fatty acyl-CoA standards were obtained from Sigma (St. Louis, Mo.).

TABLE 4

MS parameters for determination of fatty acyl-CoAs

| Fatty acyl-CoA | Ms/MS transition | Declustering potential | Entrance potential | Collison energy | Collision cell exit potential |
|---|---|---|---|---|---|
| C14:1 | 486.7/79 | −90 | −10 | −20 | −11 |
| C14:0 | 487.7/79 | −90 | −10 | −106 | −11 |
| C16:1 | 500.7/79 | −75 | −10 | −100 | −9 |
| C16:0 | 501.7/134 | −70 | −10 | −34 | −10 |
| C17:0 | 508.7/79 | −70 | −10 | −100 | −10 |
| C18:1 | 514.6/79 | −70 | −10 | −20 | −10 |
| C18:0 | 515.6/134 | −70 | −10 | −34 | −10 |

Relative fatty-acyl-CoA concentrations of different *E. coli* strains are shown in Table 5. Results indicate that disruption of ΔfadD significantly reduces the intracellular concentration of acyl-CoAs. In this example the level of acyl-CoA is reduced by ~8 fold in *E. coli* BW25113 ΔfadD containing *M. algicola* DG893 FAR compared to the strain without the deletion. However, fatty alcohol production, as reported above, is not substantially affected. Therefore, *M. algicola* DG893 FAR appears to be capable of reducing non-CoA substrates, most likely acyl-ACPs, to fatty alcohols.

TABLE 5

Fatty acyl-CoA profile exhibited by recombinant *E. coil* cells with and without expressing a heterologous *M. algicola* DG893 FAR

| Recombinant E.coli cells | Deleted protein | FAR enzyme | Total amount of acyl-CoA (ng/OD$_{600}$)[a] |
|---|---|---|---|
| BW25113 | — | — | 4.7 |
| BW25113 | — | M. algicola DG893 | 1.5 |
| BW25113 ΔfadE | Acyl-CoA dehydrogenase | — | 4.3 |
| BW25113 ΔfadD | Acyl-CoA synthetase | — | Not detectable/trace |

[a]Fatty acyl-CoA production was estimated using both internal and external standards. Fatty acyl-CoAs detected by LC-MS/MS include: 11-16% C14:0 (tetradecanoyl-CoA), 2-11% C14:1 (tetradecenoyl-CoA), 28-31% C16:1 (cis Δ$^9$-1-hexadecenoyl-CoA), 14-26% C16:0 (hexadecanoyl-CoA), 14-20% C18:1 (cis Δ$^{11}$-octadecenoyl-CoA),9-15% C18:0 (octadecanoyl-CoA).

Example 4

Expression and Activity of FARs in *S. cerevisiae* a. Construction of Vectors to Express FARs in *S. cerevisiae*

The FAR genes were PCR amplified and cloned downstream of the TEF1 promoter with BamHI and SalI sites into pCEN318 to create pCEN319 (*B. mori* FAR), pCEN328 (M algicola DG896 FAR), and pCEN333 (*Oceanobacter* sp. RED65 FAR). pCEN318 was constructed by replacing the KanMX gene of p427-TEF (Sunrise Science Products, San Diego, Calif.) with the hygromycin resistance gene. All FAR plasmids were transformed into *S. cerevisiae* FL100 by routine transformation methods.

b. In Vivo Activity of FARs in Recombinant *S. cerevisiae* Using Shake Flasks

The recombinant *S. cerevisiae* strains comprising a plasmid containing a heterologous gene encoding either the *B. mori*, *M. algicola* DG893 or *Oceanobacter* sp. RED65 FAR were inoculated into 5 ml of YPD containing 200 µg/mL hygromycin, grown at 30° C. for 48 hours (OD ~8-10). Approximately 2.5 ml were subcultured into 50 ml of YPD media (20× dilution) containing 200 µg/mL hygromycin and grown in a shaker at 30° C. and 250 rpm for 96 hours. Cell cultures were centrifuged at ~3000-4000 rpm (F15B-8×50C rotor) for 10 minutes, the supernatant was separated from cells. The pellets were washed with 20 ml of 50 mM Tris-HCl pH 7.5. Extraction and analysis of fatty alcohols were performed as described in Example 2b. Under the conditions tested, expression of *B. mori*, *M. algicola* DG893 and *Oceanobacter* sp. RED65 FAR genes in *S. cerevisiae* FL100 resulted in the production of fatty alcohols as shown in Table 6.

TABLE 6

Fatty Alcohol profile exhibited by recombinant *S. cerevisiae* FL100 host cells over-expressing the heterologous FAR enzyme genes

| FAR Enzyme | Fatty alcohol composition[a] | | | | Total (mg/L) | Secreted (mg/L) |
|---|---|---|---|---|---|---|
| | C14:0 | C16:0 | C16:1 | C18:0 | | |
| B. mori | 8 | 88 | 1 | 3 | 67 | 20 |
| Oceanobacter sp. RED65 | trace | 48 | trace | 52 | 157 | 78 |
| M. algicola DG893 | trace | 52 | trace | 48 | 300 | 150 |

[a]The relative amounts of each fatty alcohol component are expressed as a % of the total fatty alcohols detected using via GC-FID or GC-MS. Endogenous fatty alcohols include: C14:0 (1-tetradecanol), C16:0 (1-hexahecanol), and 18:0 (1-octadecanol). No unsaturated fatty alcohols were detected.
[b]Enzyme productivity was estimated using internal and external standards.

Example 5

Expression and Activity of FAR Enzymes in *Yarrowia lipolytica* a. Construction of Vectors to Express FARs in *Yarrowia lipolytica*

An autonomous replicating plasmid for expression of genes in *Y. lipolytica* was engineered with two antibiotic selection marker cassettes for resistance to hygromycin and phleomycin (HygB(R) or Ble(R), respectively) (named plasmid pCEN354). Expression of each cassette was independently regulated by a strong, constitutive promoter isolated from *Y. lipolytica*: pTEF1 for Ble(R) expression and pRPS7 for HygB(R) expression. Plasmid pCEN354 was used to assemble *Y. lipolytica* expression plasmids. Using "restriction free cloning" methodology, the FAR gene was inserted into pCEN354 to provided plasmid pCEN411 (FIG. 1). In pCEN411, heterologous gene expression is under control of the constitutive TEF1 promoter. The HygB$^R$ gene allows for selection in media containing hygromycin. Ars18 is an autonomous replicating sequence isolated from *Y. lipolytica* genomic DNA. The resulting plasmid was transformed into *Y. lipolytica* 1345 obtained from the German Resource Centre for Biological Material (DSMZ) using routine transformation methods [(Madzak, C. et al. (2003) *Yarrowia lipolytica*. In G. Gellissen (Ed.), *Production of Recombinant Proteins Novel Microbial and Eukaryotic Expression Systems* (p 163-189).].

b. In Vivo Activity of Heterologous *M. algicola* FAR in Recombinant *Y. lipolytica* Using Shake Flasks The recombinant *Y. lipolytica* strain comprising plasmid containing a heterologous gene encoding *M. algicola* DG893 FAR, was inoculated in 200 mL YPD media containing 8% glucose and 500 µg/mL hygromycin. The cultures were grown at 30° C. to an OD600 of 4-7. Cells were then harvested by centrifugation and washed with 20 ml of 50 mM Tris-HCl pH 7.5. Extraction and identification of intra- and extra-cellular fatty alcohols were performed as described in Example 2b. Under the conditions tested 14 mg/L of 1-hexadecanol was detected. Secreted fatty alcohols were not detected. Using 8% glycerol as carbon source, the total production and secretion of fatty alcohols was estimated to be ~0.8 and 0.2 g/L, respectively. Fatty alcohols include: 30% C16:0 (1-hexahecanol), 56% 18:0 (1-octadecanol) and 12% C18:1 (cis Δ$^9$-1-octadecenol).

c. In Vivo Activity of Integrated *M. algicola* FAR in *Y. lipolytica* Genome Using 96-Well Microtiter Plates An improved *Y. lipolytica* strain (YL1415) for production of fatty alcohols was identified from a library of UV-mutagenized strains defective in growth on media with hexadecane as the sole carbon source. When transformed with pCEN411, YL1415 strain showed 7-10-fold increase in fatty alcohol titer and a significant reduction in the rate of degradation of exogenous 1-hexadecanol in YPD media containing 8% glucose and 500 µg/mL hygromycin compared to that detected from *Y. lipolytica* 1345. Expression of *M. algicola* DG893 FAR was improved in the YL1415 strain by integrating the *M. algicola* DG893 FAR gene at random locations in the genome by non-homologous recombination. An integration cassette consisting of *M. algicola* FAR under control of the TEF promoter and the HygBR gene under control of the RPS promoter was amplified from pCEN411 using primers 411-F1 (AGAGACCGGGTTGGCGG) (SEQ ID NO: 17) and 411-R1 (CATTTGCCATTCGTAACGCTG) (SEQ ID NO: 18).

Transformation of YL1415 with this integration cassette yielded a library of hygromycin-resistant strains with FAR integrated at various locations in the *Y. lipolytica* genome [(Madzak, C. et al. (2003) *Yarrowia lipolytica*. In G. Gellissen (Ed.), *Production of Recombinant Proteins Novel Microbial and Eukaryotic Expression Systems* (p 163-189)]. This collection of strains with integrated *M. algicola* DG893 FAR in the YL1415 UV mutant strain was grown in 96-well Axygen 96-well plates containing 250 µL YPD supplemented with the total of 2% glucose and 500 µg/mL hygromycin. Plates were incubated in a Kuhner shaker for approximately 40-48 hours at 30° C., 200 rpm and 85% relative humidity. The cell cultures were diluted by transferring 50 µL of overnight grown cultures into the Axygen 96-well plates containing 250 µL YPD supplemented with the total of 2% glucose and 500 µg/mL hygromycin. The plates were incubated for approximately 24-28 hours in a Kuhner shaker under the similar conditions. 20 µL of the cell cultures were then transferred into deep 96-well plates containing 380 µL YPD supplemented with the total of 8% glucose and 500 µg/mL hygromycin. The Ppates were incubated for approximately 22-26 hours under similar conditions. Cells were collected by centrifugation for 10 minutes at 3500 rpm. Cell pellets were then resuspended in 400 µL of nitrogen limitation media (1.7 g/L yeast nitrogen base, 1.4 g/L (NH$_4$)$_2$SO$_4$, 30 g/L glucose) containing 500 µg/mL Hygromycin and incubated for 22-26 hours in a Kuhner shaker at 30° C., 200 rpm and 85% relative humidity. The cell cultures were then extracted with 1 mL of isopropanol:hexane (4:6 ratio) for 2 hrs. The extracts were centrifuged and the upper organic phase was transferred into polypropylene 96-well plates. Samples were then analyzed using GC-FID method as described in Example 2b. Under the conditions tested, *M. algicola* FAR integrant strains with up to ~5× improvement in total fatty alcohol production (~0.5-1 g/L) compared to plasmid-based expression were identified. Fatty alcohols include: 70-80% C16:0 (1-hexahecanol), 10-15% 18:0 (1-octadecanol) and 10-15% C18:1 (cis Δ$^9$-1-octadecenol).

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A method of producing a fatty alcohol-containing composition, the method comprising:
culturing recombinant *Escherichia coli* (*E. coli*) cells comprising a gene encoding a heterologous fatty acyl reductase (FAR) enzyme, wherein said heterologous FAR enzyme has a sequence with at least 90% amino acid sequence identity to SEQ ID NO:2, under conditions in which the FAR enzyme is expressed by said cells,
wherein said expression results in the secretion from the cells of fatty alcohols into a cell culture medium, thereby resulting in a fatty alcohol-containing composition.

2. The method of claim 1, wherein the FAR enzyme has at least 95% amino acid sequence identity to SEQ ID NO:2.

3. The method of claim 1, wherein the gene encoding the FAR enzyme comprises a nucleic acid sequence codon-optimized for expression in *E. coli*.

4. The method of claim 3, wherein the gene encoding the FAR enzyme has the sequence of SEQ ID NO:1.

5. The method of claim 1, wherein the gene encoding the FAR enzyme is integrated into the chromosome of the recombinant *E. coli* cells.

6. The method of claim 1, wherein the gene encoding the FAR enzyme is contained in an expression vector in said *E. coli* cells.

7. The method of claim 1, further comprising a step of isolating fatty alcohols from the cell culture medium.

8. The method of claim 1, wherein the fatty alcohol-containing composition comprises at least 80% by weight of C14-C18 fatty alcohols.

9. The method of claim 1, wherein at least 50% of the fatty alcohols produced by the *E. coli* cells are secreted into the culture medium.

10. The method according to claim 1, wherein the fatty alcohol-containing composition comprises at least 0.5 g/L of fatty alcohol.

11. The method according to claim 10, wherein the fatty alcohol-containing composition comprises at least 5.0 g/L of fatty alcohol.

12. The method of claim 1, wherein the cells are cultured at a temperature in the range of 20° C. to 45° C.; a pH in the range of pH 5 to pH 7, and for a time in the range of from 16 hours to 144 hours.

13. The method of claim 12, wherein the cells are cultured in the presence of fermentable sugars obtained from a cellulosic feedstock.

14. The method of claim 7, wherein
a) the FAR enzyme has at least 95% amino acid sequence identity to SEQ ID NO:2;
b) at least 50% of the fatty alcohols produced by the *E. coli* cells are secreted into the culture medium;
c) the fatty alcohol-containing composition comprises at least 80% by weight of C14-C18 fatty alcohols, and
d) the fatty alcohol-containing composition comprises at least 5.0 g/L of fatty alcohol.

* * * * *

SEQUENCE LISTING

<160> NUMBER OF SEQ ID NOS: 18

<210> SEQ ID NO 1
<211> LENGTH: 1539
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(1539)

<400> SEQUENCE: 1

```
atg gct act caa caa caa cag aac ggt gca tct gca tcc ggc gtc ttg      48
Met Ala Thr Gln Gln Gln Gln Asn Gly Ala Ser Ala Ser Gly Val Leu
1               5                   10                  15 gaa caa ctt cgt gga aag cac gtt ctt atc aca ggt act acc gga ttt      96
Glu Gln Leu Arg Gly Lys His Val Leu Ile Thr Gly Thr Thr Gly Phe
                20                  25                  30 ttg ggc aaa gtg gtt ctg gaa aag ttg att cgt act gtt ccg gat att     144
Leu Gly Lys Val Val Leu Glu Lys Leu Ile Arg Thr Val Pro Asp Ile
            35                  40                  45 gga ggt att cat ctg ctg att cgt ggc aat aaa cgt cat cca gcc gct     192
Gly Gly Ile His Leu Leu Ile Arg Gly Asn Lys Arg His Pro Ala Ala
    50                  55                  60 cgt gaa cgt ttc ctg aac gaa att gcg tcc tcc tcc gtc ttc gaa cgt     240
Arg Glu Arg Phe Leu Asn Glu Ile Ala Ser Ser Ser Val Phe Glu Arg
65                  70                  75                  80 ttg cgt cac gat gat aat gaa gcc ttc gag acc ttc ttg gaa gaa cgt     288
Leu Arg His Asp Asp Asn Glu Ala Phe Glu Thr Phe Leu Glu Glu Arg
                85                  90                  95 gtt cac tgt att acc ggt gag gtt act gaa tcc cgt ttt ggt ttg aca     336
Val His Cys Ile Thr Gly Glu Val Thr Glu Ser Arg Phe Gly Leu Thr
            100                 105                 110 cct gaa cgt ttt cgt gct ttg gcc ggt cag gtt gac gct ttt att aac     384
Pro Glu Arg Phe Arg Ala Leu Ala Gly Gln Val Asp Ala Phe Ile Asn
        115                 120                 125 agc gct gca agc gtg aac ttt cgt gag gaa ttg gat aaa gcc ctg aaa     432
Ser Ala Ala Ser Val Asn Phe Arg Glu Glu Leu Asp Lys Ala Leu Lys
    130                 135                 140 atc aac acc ttg tgt ctt gaa aat gtt gct gct ctt gca gaa ttg aac     480
Ile Asn Thr Leu Cys Leu Glu Asn Val Ala Ala Leu Ala Glu Leu Asn
145                 150                 155                 160 tcc gct atg gcg gtc att cag gtt tcc act tgt tac gtt aac ggt aaa     528
Ser Ala Met Ala Val Ile Gln Val Ser Thr Cys Tyr Val Asn Gly Lys
                165                 170                 175 aac tcc ggt caa att acc gaa tcc gtc att aaa cct gct ggc gaa tcc     576
Asn Ser Gly Gln Ile Thr Glu Ser Val Ile Lys Pro Ala Gly Glu Ser
            180                 185                 190 att ccc cgt tcc act gac ggt tac tac gag atc gaa gaa ttg gtc cat     624
Ile Pro Arg Ser Thr Asp Gly Tyr Tyr Glu Ile Glu Glu Leu Val His
        195                 200                 205 ctg ttg caa gac aag att tcc gat gtt aaa gct cgt tac tcc ggc aaa     672
Leu Leu Gln Asp Lys Ile Ser Asp Val Lys Ala Arg Tyr Ser Gly Lys
    210                 215                 220 gtt ctg gag aaa aaa ttg gtt gat ttg ggt att cgt gag gcc aat aat     720
Val Leu Glu Lys Lys Leu Val Asp Leu Gly Ile Arg Glu Ala Asn Asn
225                 230                 235                 240 tac gga tgg tcc gac acc tac aca ttc acc aaa tgg ttg ggt gaa caa     768
Tyr Gly Trp Ser Asp Thr Tyr Thr Phe Thr Lys Trp Leu Gly Glu Gln
                245                 250                 255 ctg ctg atg aag gcc ttg tct ggt cgt tct ttg act att gtg cgt ccc     816
Leu Leu Met Lys Ala Leu Ser Gly Arg Ser Leu Thr Ile Val Arg Pro
            260                 265                 270 tct att att gag tcc gct ttg gaa gaa cct tcc cct ggt tgg atc gaa     864
Ser Ile Ile Glu Ser Ala Leu Glu Glu Pro Ser Pro Gly Trp Ile Glu
        275                 280                 285 ggc gtt aaa gtt gcc gat gcc att atc ttg gct tat gcc cgt gaa aaa     912
Gly Val Lys Val Ala Asp Ala Ile Ile Leu Ala Tyr Ala Arg Glu Lys
    290                 295                 300 gtt agc ctg ttc cct gga aaa cgt tcc ggc att att gat gtt att cct     960
Val Ser Leu Phe Pro Gly Lys Arg Ser Gly Ile Ile Asp Val Ile Pro
305                 310                 315                 320
```

|   |   |   |   |   |   |   |   |   |   |   |   |   |   |   |   |   |
|---|---|---|---|---|---|---|---|---|---|---|---|---|---|---|---|---|
| gtc | gat | ttg | gtt | gcg | aac | tcc | atc | atc | ttg | tct | ctg | gct | gag | gcg | ttg | 1008 |
| Val | Asp | Leu | Val | Ala | Asn | Ser | Ile | Ile | Leu | Ser | Leu | Ala | Glu | Ala | Leu |   |
|   |   |   |   | 325 |   |   |   |   | 330 |   |   |   |   | 335 |   |   |
| tct | ggt | tct | ggt | caa | cgt | cgt | att | tat | caa | tgt | tgc | agc | ggt | ggt | tct | 1056 |
| Ser | Gly | Ser | Gly | Gln | Arg | Arg | Ile | Tyr | Gln | Cys | Cys | Ser | Gly | Gly | Ser |   |
|   |   |   | 340 |   |   |   |   | 345 |   |   |   |   | 350 |   |   |   |
| aat | cca | atc | tcc | ctg | ggt | aag | ttc | att | gat | tat | ttg | atg | gcc | gag | gct | 1104 |
| Asn | Pro | Ile | Ser | Leu | Gly | Lys | Phe | Ile | Asp | Tyr | Leu | Met | Ala | Glu | Ala |   |
|   |   | 355 |   |   |   |   | 360 |   |   |   |   | 365 |   |   |   |   |
| aag | acc | aac | tat | gct | gcc | tac | gat | caa | ctg | ttt | tat | cgt | cgt | cct | act | 1152 |
| Lys | Thr | Asn | Tyr | Ala | Ala | Tyr | Asp | Gln | Leu | Phe | Tyr | Arg | Arg | Pro | Thr |   |
|   | 370 |   |   |   |   | 375 |   |   |   |   | 380 |   |   |   |   |   |
| aaa | cct | ttc | gtc | gcc | gtg | aac | cgt | aaa | ttg | ttt | gac | gtt | gtt | gtt | ggt | 1200 |
| Lys | Pro | Phe | Val | Ala | Val | Asn | Arg | Lys | Leu | Phe | Asp | Val | Val | Val | Gly |   |
| 385 |   |   |   |   | 390 |   |   |   |   | 395 |   |   |   |   | 400 |   |
| ggt | atg | cgt | gtt | cct | ctt | tct | att | gcc | ggt | aaa | gct | atg | cgt | ttg | gct | 1248 |
| Gly | Met | Arg | Val | Pro | Leu | Ser | Ile | Ala | Gly | Lys | Ala | Met | Arg | Leu | Ala |   |
|   |   |   |   | 405 |   |   |   |   | 410 |   |   |   |   | 415 |   |   |
| ggt | caa | aat | cgt | gag | ttg | aaa | gtg | ctt | aag | aac | ctt | gat | acg | acc | cgt | 1296 |
| Gly | Gln | Asn | Arg | Glu | Leu | Lys | Val | Leu | Lys | Asn | Leu | Asp | Thr | Thr | Arg |   |
|   |   |   | 420 |   |   |   |   | 425 |   |   |   |   | 430 |   |   |   |
| tcc | ctt | gca | acc | att | ttt | ggc | ttc | tat | act | gct | ccc | gac | tat | atc | ttc | 1344 |
| Ser | Leu | Ala | Thr | Ile | Phe | Gly | Phe | Tyr | Thr | Ala | Pro | Asp | Tyr | Ile | Phe |   |
|   |   | 435 |   |   |   |   | 440 |   |   |   |   | 445 |   |   |   |   |
| cgt | aac | gat | agc | ttg | atg | gcc | ctg | gct | tct | cgt | atg | ggt | gaa | ttg | gat | 1392 |
| Arg | Asn | Asp | Ser | Leu | Met | Ala | Leu | Ala | Ser | Arg | Met | Gly | Glu | Leu | Asp |   |
|   | 450 |   |   |   |   | 455 |   |   |   |   | 460 |   |   |   |   |   |
| cgt | gtt | ctt | ttc | cca | gtt | gat | gct | cgt | caa | att | gat | tgg | cag | ttg | tac | 1440 |
| Arg | Val | Leu | Phe | Pro | Val | Asp | Ala | Arg | Gln | Ile | Asp | Trp | Gln | Leu | Tyr |   |
| 465 |   |   |   |   | 470 |   |   |   |   | 475 |   |   |   |   | 480 |   |
| ttg | tgt | aaa | att | cat | ttg | ggt | ggt | ctg | aac | cgt | tac | gct | ttg | aag | gaa | 1488 |
| Leu | Cys | Lys | Ile | His | Leu | Gly | Gly | Leu | Asn | Arg | Tyr | Ala | Leu | Lys | Glu |   |
|   |   |   |   | 485 |   |   |   |   | 490 |   |   |   |   | 495 |   |   |
| cgt | aaa | ctg | tat | tct | ttg | cgt | gct | gct | gat | act | cgt | aaa | aaa | gct | gcc | 1536 |
| Arg | Lys | Leu | Tyr | Ser | Leu | Arg | Ala | Ala | Asp | Thr | Arg | Lys | Lys | Ala | Ala |   |
|   |   |   | 500 |   |   |   |   | 505 |   |   |   |   | 510 |   |   |   |
| taa |   |   |   |   |   |   |   |   |   |   |   |   |   |   |   | 1539 |

<210> SEQ ID NO 2
<211> LENGTH: 512
<212> TYPE: PRT
<213> ORGANISM: Artificial
<220> FEATURE:
<223> OTHER INFORMATION: Synthetic Construct

<400> SEQUENCE: 2

Met Ala Thr Gln Gln Gln Gln Asn Gly Ala Ser Ala Ser Gly Val Leu
1               5                   10                  15

Glu Gln Leu Arg Gly Lys His Val Leu Ile Thr Gly Thr Thr Gly Phe
            20                  25                  30

Leu Gly Lys Val Val Leu Glu Lys Leu Ile Arg Thr Val Pro Asp Ile
        35                  40                  45

Gly Gly Ile His Leu Leu Ile Arg Gly Asn Lys Arg His Pro Ala Ala
    50                  55                  60

Arg Glu Arg Phe Leu Asn Glu Ile Ala Ser Ser Val Phe Glu Arg
65                  70                  75                  80

Leu Arg His Asp Asp Asn Glu Ala Phe Glu Thr Phe Leu Glu Glu Arg
                85                  90                  95

Val His Cys Ile Thr Gly Glu Val Thr Glu Ser Arg Phe Gly Leu Thr
            100                 105                 110

Pro Glu Arg Phe Arg Ala Leu Ala Gly Gln Val Asp Ala Phe Ile Asn
         115                 120                 125

Ser Ala Ala Ser Val Asn Phe Arg Glu Glu Leu Asp Lys Ala Leu Lys
130                 135                 140

Ile Asn Thr Leu Cys Leu Glu Asn Val Ala Leu Ala Glu Leu Asn
145                 150                 155                 160

Ser Ala Met Ala Val Ile Gln Val Ser Thr Cys Tyr Val Asn Gly Lys
                165                 170                 175

Asn Ser Gly Gln Ile Thr Glu Ser Val Ile Lys Pro Ala Gly Glu Ser
            180                 185                 190

Ile Pro Arg Ser Thr Asp Gly Tyr Tyr Glu Ile Glu Leu Val His
        195                 200                 205

Leu Leu Gln Asp Lys Ile Ser Asp Val Lys Ala Arg Tyr Ser Gly Lys
        210                 215                 220

Val Leu Glu Lys Lys Leu Val Asp Leu Gly Ile Arg Glu Ala Asn Asn
225                 230                 235                 240

Tyr Gly Trp Ser Asp Thr Tyr Thr Phe Thr Lys Trp Leu Gly Glu Gln
                245                 250                 255

Leu Leu Met Lys Ala Leu Ser Gly Arg Ser Leu Thr Ile Val Arg Pro
        260                 265                 270

Ser Ile Ile Glu Ser Ala Leu Glu Pro Ser Pro Gly Trp Ile Glu
        275                 280                 285

Gly Val Lys Val Ala Asp Ala Ile Ile Leu Ala Tyr Ala Arg Glu Lys
        290                 295                 300

Val Ser Leu Phe Pro Gly Lys Arg Ser Gly Ile Ile Asp Val Ile Pro
305                 310                 315                 320

Val Asp Leu Val Ala Asn Ser Ile Ile Leu Ser Leu Ala Glu Ala Leu
                325                 330                 335

Ser Gly Ser Gly Gln Arg Arg Ile Tyr Gln Cys Cys Ser Gly Gly Ser
            340                 345                 350

Asn Pro Ile Ser Leu Gly Lys Phe Ile Asp Tyr Leu Met Ala Glu Ala
        355                 360                 365

Lys Thr Asn Tyr Ala Ala Tyr Asp Gln Leu Phe Tyr Arg Arg Pro Thr
        370                 375                 380

Lys Pro Phe Val Ala Val Asn Arg Lys Leu Phe Asp Val Val Gly
385                 390                 395                 400

Gly Met Arg Val Pro Leu Ser Ile Ala Gly Lys Ala Met Arg Leu Ala
                405                 410                 415

Gly Gln Asn Arg Glu Leu Lys Val Leu Lys Asn Leu Asp Thr Thr Arg
            420                 425                 430

Ser Leu Ala Thr Ile Phe Gly Phe Tyr Thr Ala Pro Asp Tyr Ile Phe
        435                 440                 445

Arg Asn Asp Ser Leu Met Ala Leu Ala Ser Arg Met Gly Glu Leu Asp
450                 455                 460

Arg Val Leu Phe Pro Val Asp Ala Arg Gln Ile Asp Trp Gln Leu Tyr
465                 470                 475                 480

Leu Cys Lys Ile His Leu Gly Gly Leu Asn Arg Tyr Ala Leu Lys Glu
                485                 490                 495

Arg Lys Leu Tyr Ser Leu Arg Ala Ala Asp Thr Arg Lys Lys Ala Ala
            500                 505                 510

<210> SEQ ID NO 3
<211> LENGTH: 1536
<212> TYPE: DNA

```
<213> ORGANISM: Artificial
<220> FEATURE:
<223> OTHER INFORMATION: Synthetic
<220> FEATURE:
<221> NAME/KEY: CDS
<222> LOCATION: (1)..(1536)

<400> SEQUENCE: 3 atg gcc acc cag cag cag cag aac ggt gca tcc gct tcg ggc gtt ctg      48
Met Ala Thr Gln Gln Gln Gln Asn Gly Ala Ser Ala Ser Gly Val Leu
1               5                  10                  15 gag cag ctt aga ggc aag cat gtc ttg att acc ggt act aca gga ttt      96
Glu Gln Leu Arg Gly Lys His Val Leu Ile Thr Gly Thr Thr Gly Phe
            20                  25                  30 ctg gga aag gtg gtt ctg gag aag ctg atc cga acc gtg cct gac atc     144
Leu Gly Lys Val Val Leu Glu Lys Leu Ile Arg Thr Val Pro Asp Ile
        35                  40                  45 ggt ggt att cat ctg ctg att aga ggc aac aag aga cat cct gct gcc     192
Gly Gly Ile His Leu Leu Ile Arg Gly Asn Lys Arg His Pro Ala Ala
    50                  55                  60 aga gaa aga ttc ttg aac gaa atc gcc tct tcc tct gtg ttc gag cgg     240
Arg Glu Arg Phe Leu Asn Glu Ile Ala Ser Ser Ser Val Phe Glu Arg
65                  70                  75                  80 ctt aga cat gac gac aac gaa gcc ttt gag act ttc ctg gag gag cgt     288
Leu Arg His Asp Asp Asn Glu Ala Phe Glu Thr Phe Leu Glu Glu Arg
                85                  90                  95 gtg cac tgc atc acc gga gaa gtg acc gag tcg aga ttt ggc ctt act     336
Val His Cys Ile Thr Gly Glu Val Thr Glu Ser Arg Phe Gly Leu Thr
            100                 105                 110 cct gag cgg ttc cga gcc ctt gct ggc caa gtg gat gcc ttc atc aat     384
Pro Glu Arg Phe Arg Ala Leu Ala Gly Gln Val Asp Ala Phe Ile Asn
        115                 120                 125 tcc gcc gcc tct gtt aac ttc aga gag gag ctg gac aag gca ctc aag     432
Ser Ala Ala Ser Val Asn Phe Arg Glu Glu Leu Asp Lys Ala Leu Lys
    130                 135                 140 atc aac acc ctg tgt ctg gag aac gtg gct gct ctg gcc gaa ctt aac     480
Ile Asn Thr Leu Cys Leu Glu Asn Val Ala Ala Leu Ala Glu Leu Asn
145                 150                 155                 160 tcc gct atg gca gtg atc caa gtt tcc acc tgt tac gtg aac ggc aag     528
Ser Ala Met Ala Val Ile Gln Val Ser Thr Cys Tyr Val Asn Gly Lys
                165                 170                 175 aac tct gga cag atc acc gag tcc gtt atc aag ccc gct ggc gaa tcc     576
Asn Ser Gly Gln Ile Thr Glu Ser Val Ile Lys Pro Ala Gly Glu Ser
            180                 185                 190 atc ccc aga tcc aca gat ggc tac tac gag atc gag gag ctg gtc cac     624
Ile Pro Arg Ser Thr Asp Gly Tyr Tyr Glu Ile Glu Glu Leu Val His
        195                 200                 205 ctt ctg caa gac aag atc tcc gac gtg aag gct cga tac tct ggc aag     672
Leu Leu Gln Asp Lys Ile Ser Asp Val Lys Ala Arg Tyr Ser Gly Lys
    210                 215                 220 gtg ttg gag aag aag ctg gtg gac ctg ggc atc cga gag gcg aac aac     720
Val Leu Glu Lys Lys Leu Val Asp Leu Gly Ile Arg Glu Ala Asn Asn
225                 230                 235                 240 tac ggc tgg tct gac acc tac acc ttc acc aaa tgg ctc gga gag cag     768
Tyr Gly Trp Ser Asp Thr Tyr Thr Phe Thr Lys Trp Leu Gly Glu Gln
                245                 250                 255 ctt ctg atg aaa gct ctg tcc gga aga tcc ctg act atc gtg cgg cct     816
Leu Leu Met Lys Ala Leu Ser Gly Arg Ser Leu Thr Ile Val Arg Pro
            260                 265                 270 tcc atc atc gag tcg gct ctt gaa gag cct tct cca ggt tgg atc gag     864
Ser Ile Ile Glu Ser Ala Leu Glu Glu Pro Ser Pro Gly Trp Ile Glu
        275                 280                 285
```

```
ggc gtg aag gtt gct gac gcc atc atc ctt gcg tac gcc aga gag aag         912
Gly Val Lys Val Ala Asp Ala Ile Ile Leu Ala Tyr Ala Arg Glu Lys
        290                 295                 300 gtt tcg ttg ttc ccc ggc aag cga tct ggc atc atc gac gtt atc ccc         960
Val Ser Leu Phe Pro Gly Lys Arg Ser Gly Ile Ile Asp Val Ile Pro
305                 310                 315                 320 gtg gat ctg gtg gcc aac tct atc att ctc tct ctt gct gaa gcc ctt        1008
Val Asp Leu Val Ala Asn Ser Ile Ile Leu Ser Leu Ala Glu Ala Leu
                325                 330                 335 tct gga tct ggc cag cgt aga atc tac caa tgt tgt tct ggc ggt tct        1056
Ser Gly Ser Gly Gln Arg Arg Ile Tyr Gln Cys Cys Ser Gly Gly Ser
        340                 345                 350 aac ccg att tct ctg ggc aag ttc atc gac tac ctt atg gcc gaa gcc        1104
Asn Pro Ile Ser Leu Gly Lys Phe Ile Asp Tyr Leu Met Ala Glu Ala
355                 360                 365 aag acc aac tat gct gcc tac gac cag ctc ttc tac cga cga ccc acc        1152
Lys Thr Asn Tyr Ala Ala Tyr Asp Gln Leu Phe Tyr Arg Arg Pro Thr
        370                 375                 380 aag ccc ttc gtc gct gtg aac cga aag ctg ttc gat gtt gtc gtg gga        1200
Lys Pro Phe Val Ala Val Asn Arg Lys Leu Phe Asp Val Val Val Gly
385                 390                 395                 400 gga atg cga gtg cct ctt tcc att gct ggc aag gcc atg aga ttg gcg        1248
Gly Met Arg Val Pro Leu Ser Ile Ala Gly Lys Ala Met Arg Leu Ala
                405                 410                 415 ggt cag aat cga gaa ttg aag gtt ctc aag aac ctt gac act act cga        1296
Gly Gln Asn Arg Glu Leu Lys Val Leu Lys Asn Leu Asp Thr Thr Arg
        420                 425                 430 tcg ctc gct act atc ttt gga ttc tac act gct cct gac tac atc ttc        1344
Ser Leu Ala Thr Ile Phe Gly Phe Tyr Thr Ala Pro Asp Tyr Ile Phe
435                 440                 445 cgg aat gac tct ctg atg gct ctt gct tcc cga atg gga gaa ctc gat        1392
Arg Asn Asp Ser Leu Met Ala Leu Ala Ser Arg Met Gly Glu Leu Asp
        450                 455                 460 cgt gtg ctg ttc cct gtt gac gct cga cag atc gac tgg cag ctc tac        1440
Arg Val Leu Phe Pro Val Asp Ala Arg Gln Ile Asp Trp Gln Leu Tyr
465                 470                 475                 480 ttg tgt aag atc cac ctg ggc ggc ctg aac cga tat gct ctg aaa gaa        1488
Leu Cys Lys Ile His Leu Gly Gly Leu Asn Arg Tyr Ala Leu Lys Glu
                485                 490                 495 cga aag ctg tac agc ctt aga gcc gct gat acc cga aag aag gct gct        1536
Arg Lys Leu Tyr Ser Leu Arg Ala Ala Asp Thr Arg Lys Lys Ala Ala
        500                 505                 510

<210> SEQ ID NO 4
<211> LENGTH: 512
<212> TYPE: PRT
<213> ORGANISM: Artificial
<220> FEATURE:
<223> OTHER INFORMATION: Synthetic Construct

<400> SEQUENCE: 4

Met Ala Thr Gln Gln Gln Asn Gly Ala Ser Ala Ser Gly Val Leu
1               5                   10                  15

Glu Gln Leu Arg Gly Lys His Val Leu Ile Thr Gly Thr Thr Gly Phe
                20                  25                  30

Leu Gly Lys Val Val Leu Glu Lys Leu Ile Arg Thr Val Pro Asp Ile
        35                  40                  45

Gly Gly Ile His Leu Leu Ile Arg Gly Asn Lys Arg His Pro Ala Ala
    50                  55                  60

Arg Glu Arg Phe Leu Asn Glu Ile Ala Ser Ser Ser Val Phe Glu Arg
```

```
            65                  70                  75                  80
Leu Arg His Asp Asp Asn Glu Ala Phe Glu Thr Phe Leu Glu Arg
                    85                  90                  95

Val His Cys Ile Thr Gly Glu Val Thr Glu Ser Arg Phe Gly Leu Thr
                    100                 105                 110

Pro Glu Arg Phe Arg Ala Leu Ala Gly Gln Val Asp Ala Phe Ile Asn
                    115                 120                 125

Ser Ala Ala Ser Val Asn Phe Arg Glu Glu Leu Asp Lys Ala Leu Lys
                    130                 135                 140

Ile Asn Thr Leu Cys Leu Glu Asn Val Ala Ala Leu Ala Glu Leu Asn
145                 150                 155                 160

Ser Ala Met Ala Val Ile Gln Val Ser Thr Cys Tyr Val Asn Gly Lys
                    165                 170                 175

Asn Ser Gly Gln Ile Thr Glu Ser Val Ile Lys Pro Ala Gly Glu Ser
                    180                 185                 190

Ile Pro Arg Ser Thr Asp Gly Tyr Tyr Glu Ile Glu Glu Leu Val His
                    195                 200                 205

Leu Leu Gln Asp Lys Ile Ser Asp Val Lys Ala Arg Tyr Ser Gly Lys
                    210                 215                 220

Val Leu Glu Lys Lys Leu Val Asp Leu Gly Ile Arg Glu Ala Asn Asn
225                 230                 235                 240

Tyr Gly Trp Ser Asp Thr Tyr Thr Phe Thr Lys Trp Leu Gly Glu Gln
                    245                 250                 255

Leu Leu Met Lys Ala Leu Ser Gly Arg Ser Leu Thr Ile Val Arg Pro
                    260                 265                 270

Ser Ile Ile Glu Ser Ala Leu Glu Glu Pro Ser Pro Gly Trp Ile Glu
                    275                 280                 285

Gly Val Lys Val Ala Asp Ala Ile Ile Leu Ala Tyr Ala Arg Glu Lys
                    290                 295                 300

Val Ser Leu Phe Pro Gly Lys Arg Ser Gly Ile Ile Asp Val Ile Pro
305                 310                 315                 320

Val Asp Leu Val Ala Asn Ser Ile Ile Leu Ser Leu Ala Glu Ala Leu
                    325                 330                 335

Ser Gly Ser Gly Gln Arg Arg Ile Tyr Gln Cys Cys Ser Gly Gly Ser
                    340                 345                 350

Asn Pro Ile Ser Leu Gly Lys Phe Ile Asp Tyr Leu Met Ala Glu Ala
                    355                 360                 365

Lys Thr Asn Tyr Ala Ala Tyr Asp Gln Leu Phe Tyr Arg Arg Pro Thr
                    370                 375                 380

Lys Pro Phe Val Ala Val Asn Arg Lys Leu Phe Asp Val Val Gly
385                 390                 395                 400

Gly Met Arg Val Pro Leu Ser Ile Ala Gly Lys Ala Met Arg Leu Ala
                    405                 410                 415

Gly Gln Asn Arg Glu Leu Lys Val Leu Lys Asn Leu Asp Thr Thr Arg
                    420                 425                 430

Ser Leu Ala Thr Ile Phe Gly Phe Tyr Thr Ala Pro Asp Tyr Ile Phe
                    435                 440                 445

Arg Asn Asp Ser Leu Met Ala Leu Ala Ser Arg Met Gly Glu Leu Asp
                    450                 455                 460

Arg Val Leu Phe Pro Val Asp Ala Arg Gln Ile Asp Trp Gln Leu Tyr
465                 470                 475                 480

Leu Cys Lys Ile His Leu Gly Gly Leu Asn Arg Tyr Ala Leu Lys Glu
                    485                 490                 495
```

```
                    Arg Lys Leu Tyr Ser Leu Arg Ala Ala Asp Thr Arg Lys Lys Ala Ala
                                    500                 505                 510

<210> SEQ ID NO 5
<211> LENGTH: 1545
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(1545)

<400> SEQUENCE: 5 atg tct cag tac tcc gcg ttc tcc gtt tct caa tct ttg aag ggc aaa      48
Met Ser Gln Tyr Ser Ala Phe Ser Val Ser Gln Ser Leu Lys Gly Lys
1               5                   10                  15 cat atc ttc ttg aca ggt gtt acg ggt ttc ttg ggc aag gcg att ctg      96
His Ile Phe Leu Thr Gly Val Thr Gly Phe Leu Gly Lys Ala Ile Leu
                20                  25                  30 gag aaa ctg ttg tac tcc gtt cca caa ttg gct cag att cat atc ctg     144
Glu Lys Leu Leu Tyr Ser Val Pro Gln Leu Ala Gln Ile His Ile Leu
            35                  40                  45 gtc cgt ggt ggt aaa gtt agc gct aag aag cgt ttc caa cat gac atc     192
Val Arg Gly Gly Lys Val Ser Ala Lys Lys Arg Phe Gln His Asp Ile
        50                  55                  60 ttg ggt tct tcc atc ttt gag cgt ctt aag gaa caa cat ggc gaa cat     240
Leu Gly Ser Ser Ile Phe Glu Arg Leu Lys Glu Gln His Gly Glu His
65                  70                  75                  80 ttc gaa gaa tgg gtt caa agc aag atc aac ctt gtc gag ggc gaa ctt     288
Phe Glu Glu Trp Val Gln Ser Lys Ile Asn Leu Val Glu Gly Glu Leu
                85                  90                  95 act caa cct atg ttc gat ttg cct tct gct gag ttc gct ggc ttg gct     336
Thr Gln Pro Met Phe Asp Leu Pro Ser Ala Glu Phe Ala Gly Leu Ala
            100                 105                 110 aac caa ttg gat ctg atc atc aat agc gct gct tct gtc aac ttt cgt     384
Asn Gln Leu Asp Leu Ile Ile Asn Ser Ala Ala Ser Val Asn Phe Arg
        115                 120                 125 gag aac ttg gag aag gct ctg aac atc aat acc ctg tgt ctg aac aac     432
Glu Asn Leu Glu Lys Ala Leu Asn Ile Asn Thr Leu Cys Leu Asn Asn
    130                 135                 140 atc att gcg ctg gct cag tac aac gtc gct gct caa act cct gtt atg     480
Ile Ile Ala Leu Ala Gln Tyr Asn Val Ala Ala Gln Thr Pro Val Met
145                 150                 155                 160 caa atc tcc acc tgc tat gtc aac ggc ttc aac aaa ggc caa atc aac     528
Gln Ile Ser Thr Cys Tyr Val Asn Gly Phe Asn Lys Gly Gln Ile Asn
                165                 170                 175 gag gaa gtt gtt ggt cct gct tct ggt ttg att cct cag ttg tcc caa     576
Glu Glu Val Val Gly Pro Ala Ser Gly Leu Ile Pro Gln Leu Ser Gln
            180                 185                 190 gac tgc tac gac att gat tcc gtc ttc aag cgt gtt cat tcc cag att     624
Asp Cys Tyr Asp Ile Asp Ser Val Phe Lys Arg Val His Ser Gln Ile
        195                 200                 205 gaa caa gtc aag aaa cgt aag acc gac att gaa cag caa gaa caa gcc     672
Glu Gln Val Lys Lys Arg Lys Thr Asp Ile Glu Gln Gln Glu Gln Ala
    210                 215                 220 ttg atc aaa ctg ggt atc aag acc tct caa cat ttc ggc tgg aat gat     720
Leu Ile Lys Leu Gly Ile Lys Thr Ser Gln His Phe Gly Trp Asn Asp
225                 230                 235                 240 acc tac acc ttc acc aag tgg ctg ggt gaa caa ttg ttg att cag aag     768
Thr Tyr Thr Phe Thr Lys Trp Leu Gly Glu Gln Leu Leu Ile Gln Lys
                245                 250                 255
```

```
ttg  ggc  aag  caa  tct  ttg  aca  att  ctt  cgt  ccg  tcc  atc  atc  gaa  tct      816
Leu  Gly  Lys  Gln  Ser  Leu  Thr  Ile  Leu  Arg  Pro  Ser  Ile  Ile  Glu  Ser
          260                 265                 270 gct  gtt  cgt  gaa  cct  gct  cct  ggc  tgg  gtt  gaa  ggc  gtg  aaa  gtt  gcg      864
Ala  Val  Arg  Glu  Pro  Ala  Pro  Gly  Trp  Val  Glu  Gly  Val  Lys  Val  Ala
     275                 280                 285 gat  gcc  ttg  atc  tat  gct  tac  gct  aaa  ggt  cgt  gtt  agc  atc  ttt  ccc      912
Asp  Ala  Leu  Ile  Tyr  Ala  Tyr  Ala  Lys  Gly  Arg  Val  Ser  Ile  Phe  Pro
290                 295                 300 ggt  cgt  gat  gaa  ggt  atc  ttg  gat  gtc  atc  cct  gtt  gat  ttg  gtt  gct      960
Gly  Arg  Asp  Glu  Gly  Ile  Leu  Asp  Val  Ile  Pro  Val  Asp  Leu  Val  Ala
305                 310                 315                 320 aat  gcc  gcc  gca  ttg  tcc  gct  gct  cag  ctt  atg  gaa  tct  aac  cag  caa     1008
Asn  Ala  Ala  Ala  Leu  Ser  Ala  Ala  Gln  Leu  Met  Glu  Ser  Asn  Gln  Gln
               325                 330                 335 act  ggc  tat  cgt  atc  tat  caa  tgc  tgt  tct  ggt  tcc  cgt  aat  ccg  atc     1056
Thr  Gly  Tyr  Arg  Ile  Tyr  Gln  Cys  Cys  Ser  Gly  Ser  Arg  Asn  Pro  Ile
          340                 345                 350 aag  ctg  aaa  gag  ttc  att  cgt  cac  att  cag  aat  gtt  gct  caa  gcc  cgt     1104
Lys  Leu  Lys  Glu  Phe  Ile  Arg  His  Ile  Gln  Asn  Val  Ala  Gln  Ala  Arg
     355                 360                 365 tac  caa  gaa  tgg  cca  aag  ttg  ttt  gct  gac  aaa  cct  cag  gaa  gcc  ttc     1152
Tyr  Gln  Glu  Trp  Pro  Lys  Leu  Phe  Ala  Asp  Lys  Pro  Gln  Glu  Ala  Phe
370                 375                 380 aag  acc  gtg  tct  cct  aaa  cgt  ttc  aag  ctg  tac  atg  tct  ggt  ttc  act     1200
Lys  Thr  Val  Ser  Pro  Lys  Arg  Phe  Lys  Leu  Tyr  Met  Ser  Gly  Phe  Thr
385                 390                 395                 400 gct  atc  aca  tgg  gct  aag  acc  atc  att  ggt  cgt  gtc  ttt  gga  tct  aat     1248
Ala  Ile  Thr  Trp  Ala  Lys  Thr  Ile  Ile  Gly  Arg  Val  Phe  Gly  Ser  Asn
               405                 410                 415 gct  gcc  tcc  caa  cac  atg  ttg  aag  gct  aag  acc  aca  gca  tct  ttg  gcg     1296
Ala  Ala  Ser  Gln  His  Met  Leu  Lys  Ala  Lys  Thr  Thr  Ala  Ser  Leu  Ala
          420                 425                 430 aac  atc  ttt  ggt  ttc  tac  act  gct  cct  aac  tac  cgt  ttc  tcc  tct  cag     1344
Asn  Ile  Phe  Gly  Phe  Tyr  Thr  Ala  Pro  Asn  Tyr  Arg  Phe  Ser  Ser  Gln
     435                 440                 445 aag  ttg  gaa  cag  ttg  gtc  aaa  cag  ttc  gat  act  acc  gaa  caa  cgt  ctt     1392
Lys  Leu  Glu  Gln  Leu  Val  Lys  Gln  Phe  Asp  Thr  Thr  Glu  Gln  Arg  Leu
450                 455                 460 tac  gac  att  cgt  gct  gac  cat  ttc  gat  tgg  aag  tac  tac  ttg  cag  gaa     1440
Tyr  Asp  Ile  Arg  Ala  Asp  His  Phe  Asp  Trp  Lys  Tyr  Tyr  Leu  Gln  Glu
465                 470                 475                 480 gtt  cac  atg  gat  ggt  ctt  cac  aag  tat  gcg  ttg  gcc  gat  cgt  caa  gaa     1488
Val  His  Met  Asp  Gly  Leu  His  Lys  Tyr  Ala  Leu  Ala  Asp  Arg  Gln  Glu
               485                 490                 495 ttg  aag  ccc  aaa  cat  gtg  aag  aag  cgt  aaa  cgt  gaa  acg  att  cgt  caa     1536
Leu  Lys  Pro  Lys  His  Val  Lys  Lys  Arg  Lys  Arg  Glu  Thr  Ile  Arg  Gln
          500                 505                 510 gct  gct  taa                                                                       1545
Ala  Ala <210> SEQ ID NO 6
<211> LENGTH: 514
<212> TYPE: PRT
<213> ORGANISM: Artificial
<220> FEATURE:
<223> OTHER INFORMATION: Synthetic Construct

<400> SEQUENCE: 6

Met Ser Gln Tyr Ser Ala Phe Ser Val Ser Gln Ser Leu Lys Gly Lys
1               5                   10                  15
```

-continued

```
His Ile Phe Leu Thr Gly Val Thr Gly Phe Leu Gly Lys Ala Ile Leu
         20                  25                  30

Glu Lys Leu Leu Tyr Ser Val Pro Gln Leu Ala Gln Ile His Ile Leu
         35                  40                  45

Val Arg Gly Lys Val Ser Ala Lys Lys Arg Phe Gln His Asp Ile
 50                  55                  60

Leu Gly Ser Ser Ile Phe Glu Arg Leu Lys Glu Gln His Gly Glu His
 65                  70                  75                  80

Phe Glu Glu Trp Val Gln Ser Lys Ile Asn Leu Val Glu Gly Glu Leu
                 85                  90                  95

Thr Gln Pro Met Phe Asp Leu Pro Ser Ala Glu Phe Ala Gly Leu Ala
            100                 105                 110

Asn Gln Leu Asp Leu Ile Ile Asn Ser Ala Ala Ser Val Asn Phe Arg
        115                 120                 125

Glu Asn Leu Glu Lys Ala Leu Asn Ile Asn Thr Leu Cys Leu Asn Asn
        130                 135                 140

Ile Ile Ala Leu Ala Gln Tyr Asn Val Ala Ala Gln Thr Pro Val Met
145                 150                 155                 160

Gln Ile Ser Thr Cys Tyr Val Asn Gly Phe Asn Lys Gly Gln Ile Asn
                165                 170                 175

Glu Glu Val Val Gly Pro Ala Ser Gly Leu Ile Pro Gln Leu Ser Gln
            180                 185                 190

Asp Cys Tyr Asp Ile Asp Ser Val Phe Lys Arg Val His Ser Gln Ile
        195                 200                 205

Glu Gln Val Lys Lys Arg Lys Thr Asp Ile Glu Gln Gln Glu Gln Ala
        210                 215                 220

Leu Ile Lys Leu Gly Ile Lys Thr Ser Gln His Phe Gly Trp Asn Asp
225                 230                 235                 240

Thr Tyr Thr Phe Thr Lys Trp Leu Gly Glu Gln Leu Leu Ile Gln Lys
                245                 250                 255

Leu Gly Lys Gln Ser Leu Thr Ile Leu Arg Pro Ser Ile Ile Glu Ser
            260                 265                 270

Ala Val Arg Glu Pro Ala Pro Gly Trp Val Glu Gly Val Lys Val Ala
        275                 280                 285

Asp Ala Leu Ile Tyr Ala Tyr Ala Lys Gly Arg Val Ser Ile Phe Pro
        290                 295                 300

Gly Arg Asp Glu Gly Ile Leu Asp Val Ile Pro Val Asp Leu Val Ala
305                 310                 315                 320

Asn Ala Ala Ala Leu Ser Ala Ala Gln Leu Met Glu Ser Asn Gln Gln
                325                 330                 335

Thr Gly Tyr Arg Ile Tyr Gln Cys Cys Ser Gly Ser Arg Asn Pro Ile
            340                 345                 350

Lys Leu Lys Glu Phe Ile Arg His Ile Gln Asn Val Ala Gln Ala Arg
        355                 360                 365

Tyr Gln Glu Trp Pro Lys Leu Phe Ala Asp Lys Pro Gln Glu Ala Phe
        370                 375                 380

Lys Thr Val Ser Pro Lys Arg Phe Lys Leu Tyr Met Ser Gly Phe Thr
385                 390                 395                 400

Ala Ile Thr Trp Ala Lys Thr Ile Ile Gly Arg Val Phe Gly Ser Asn
                405                 410                 415

Ala Ala Ser Gln His Met Leu Lys Ala Lys Thr Thr Ala Ser Leu Ala
            420                 425                 430

Asn Ile Phe Gly Phe Tyr Thr Ala Pro Asn Tyr Arg Phe Ser Ser Gln
        435                 440                 445
```

```
Lys Leu Glu Gln Leu Val Lys Gln Phe Asp Thr Thr Glu Gln Arg Leu
    450                 455                 460

Tyr Asp Ile Arg Ala Asp His Phe Asp Trp Lys Tyr Tyr Leu Gln Glu
465                 470                 475                 480

Val His Met Asp Gly Leu His Lys Tyr Ala Leu Ala Asp Arg Gln Glu
                    485                 490                 495

Leu Lys Pro Lys His Val Lys Lys Arg Lys Arg Glu Thr Ile Arg Gln
                500                 505                 510

Ala Ala

<210> SEQ ID NO 7
<211> LENGTH: 1542
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(1542)

<400> SEQUENCE: 7
```

| | | | | | | | | | | | | | | | | |
|---|---|---|---|---|---|---|---|---|---|---|---|---|---|---|---|---|
| atg | tcc | cag | tac | tcg | gct | ttc | tct | gtt | tct | caa | tct | ctg | aag | ggc | aag | 48 |
| Met | Ser | Gln | Tyr | Ser | Ala | Phe | Ser | Val | Ser | Gln | Ser | Leu | Lys | Gly | Lys | |
| 1 | | | | 5 | | | | | 10 | | | | | 15 | | |
| cac | atc | ttt | ctc | act | ggt | gtc | act | ggc | ttt | ctc | gga | aag | gca | att | ctg | 96 |
| His | Ile | Phe | Leu | Thr | Gly | Val | Thr | Gly | Phe | Leu | Gly | Lys | Ala | Ile | Leu | |
| | | | 20 | | | | | 25 | | | | | 30 | | | |
| gag | aag | ctc | ttg | tac | tcg | gtt | ccc | cag | ctg | gca | cag | atc | cat | atc | ctt | 144 |
| Glu | Lys | Leu | Leu | Tyr | Ser | Val | Pro | Gln | Leu | Ala | Gln | Ile | His | Ile | Leu | |
| | | 35 | | | | | 40 | | | | | 45 | | | | |
| gtg | aga | ggc | ggc | aaa | gtt | tct | gcc | aag | aag | cgg | ttt | cag | cac | gac | atc | 192 |
| Val | Arg | Gly | Gly | Lys | Val | Ser | Ala | Lys | Lys | Arg | Phe | Gln | His | Asp | Ile | |
| 50 | | | | | 55 | | | | | 60 | | | | | | |
| ctg | ggc | tct | agc | atc | ttc | gag | aga | ctt | aag | gag | caa | cac | gga | gag | cac | 240 |
| Leu | Gly | Ser | Ser | Ile | Phe | Glu | Arg | Leu | Lys | Glu | Gln | His | Gly | Glu | His | |
| 65 | | | | | 70 | | | | | 75 | | | | | 80 | |
| ttt | gag | gaa | tgg | gtt | cag | tcc | aag | atc | aac | ctt | gtg | gag | gga | gaa | ctg | 288 |
| Phe | Glu | Glu | Trp | Val | Gln | Ser | Lys | Ile | Asn | Leu | Val | Glu | Gly | Glu | Leu | |
| | | | | 85 | | | | | 90 | | | | | 95 | | |
| act | caa | cca | atg | ttt | gac | ctc | cct | tct | gct | gag | ttc | gct | gga | ctt | gct | 336 |
| Thr | Gln | Pro | Met | Phe | Asp | Leu | Pro | Ser | Ala | Glu | Phe | Ala | Gly | Leu | Ala | |
| | | | 100 | | | | | 105 | | | | | 110 | | | |
| aac | cag | ctg | gac | ctg | atc | atc | aac | tct | gcc | gct | tcg | gtt | aac | ttt | cga | 384 |
| Asn | Gln | Leu | Asp | Leu | Ile | Ile | Asn | Ser | Ala | Ala | Ser | Val | Asn | Phe | Arg | |
| | | 115 | | | | | 120 | | | | | 125 | | | | |
| gag | aac | ctg | gag | aag | gct | ctg | aac | atc | aac | acc | ctg | tgc | ctg | aac | aac | 432 |
| Glu | Asn | Leu | Glu | Lys | Ala | Leu | Asn | Ile | Asn | Thr | Leu | Cys | Leu | Asn | Asn | |
| | 130 | | | | | 135 | | | | | 140 | | | | | |
| atc | atc | gct | ctg | gct | cag | tac | aat | gtc | gct | gcc | cag | act | cct | gtg | atg | 480 |
| Ile | Ile | Ala | Leu | Ala | Gln | Tyr | Asn | Val | Ala | Ala | Gln | Thr | Pro | Val | Met | |
| 145 | | | | | 150 | | | | | 155 | | | | | 160 | |
| cag | att | tcc | acc | tgc | tac | gtg | aac | ggc | ttc | aac | aag | ggc | cag | atc | aac | 528 |
| Gln | Ile | Ser | Thr | Cys | Tyr | Val | Asn | Gly | Phe | Asn | Lys | Gly | Gln | Ile | Asn | |
| | | | | 165 | | | | | 170 | | | | | 175 | | |
| gaa | gaa | gtt | gtg | gga | cct | gct | tct | gga | ctg | atc | cct | cag | ctg | tct | caa | 576 |
| Glu | Glu | Val | Val | Gly | Pro | Ala | Ser | Gly | Leu | Ile | Pro | Gln | Leu | Ser | Gln | |
| | | | 180 | | | | | 185 | | | | | 190 | | | |
| gat | tgc | tac | gac | atc | gac | tcc | gtc | ttc | aag | aga | gtg | cat | tcc | cag | att | 624 |
| Asp | Cys | Tyr | Asp | Ile | Asp | Ser | Val | Phe | Lys | Arg | Val | His | Ser | Gln | Ile | |
| | | 195 | | | | | 200 | | | | | 205 | | | | |

```
gag cag gtg aag aag aga aag aca gac att gag cag cag gaa caa gcc      672
Glu Gln Val Lys Lys Arg Lys Thr Asp Ile Glu Gln Gln Glu Gln Ala
    210                 215                 220 ctt atc aag ctc ggt atc aag act tcc cag cac ttt ggc tgg aat gac      720
Leu Ile Lys Leu Gly Ile Lys Thr Ser Gln His Phe Gly Trp Asn Asp
225                 230                 235                 240 act tac acc ttc acc aaa tgg ctc ggc gaa cag ctg ttg att cag aag      768
Thr Tyr Thr Phe Thr Lys Trp Leu Gly Glu Gln Leu Leu Ile Gln Lys
                245                 250                 255 ctc ggc aag caa tct ctc acc att ctt cga cct tcg atc att gag tct      816
Leu Gly Lys Gln Ser Leu Thr Ile Leu Arg Pro Ser Ile Ile Glu Ser
            260                 265                 270 gct gtg aga gag cct gcg ccc gga tgg gtc gaa gga gtg aaa gtc gct      864
Ala Val Arg Glu Pro Ala Pro Gly Trp Val Glu Gly Val Lys Val Ala
        275                 280                 285 gac gcc ctt atc tac gct tat gct aag gga aga gtc tcg atc ttt cct      912
Asp Ala Leu Ile Tyr Ala Tyr Ala Lys Gly Arg Val Ser Ile Phe Pro
    290                 295                 300 gga aga gac gag ggc atc ctt gat gtg att ccc gtt gac ctt gtt gcc      960
Gly Arg Asp Glu Gly Ile Leu Asp Val Ile Pro Val Asp Leu Val Ala
305                 310                 315                 320 aat gct gct gct ctt tct gct gca caa ctc atg gag tcc aac caa cag     1008
Asn Ala Ala Ala Leu Ser Ala Ala Gln Leu Met Glu Ser Asn Gln Gln
                325                 330                 335 act ggc tac cga atc tac caa tgc tgc tct gga tct cga aac ccc atc     1056
Thr Gly Tyr Arg Ile Tyr Gln Cys Cys Ser Gly Ser Arg Asn Pro Ile
            340                 345                 350 aag ctg aag gag ttc atc cga cac atc cag aac gtg gct cag gcc cga     1104
Lys Leu Lys Glu Phe Ile Arg His Ile Gln Asn Val Ala Gln Ala Arg
        355                 360                 365 tac cag gaa tgg cct aag ctg ttt gcc gat aag cct caa gag gcc ttc     1152
Tyr Gln Glu Trp Pro Lys Leu Phe Ala Asp Lys Pro Gln Glu Ala Phe
    370                 375                 380 aag act gtc tct ccc aag aga ttc aag ctg tac atg tcc ggc ttc act     1200
Lys Thr Val Ser Pro Lys Arg Phe Lys Leu Tyr Met Ser Gly Phe Thr
385                 390                 395                 400 gcc atc acc tgg gct aag acc atc att ggc cga gtg ttc ggc tct aac     1248
Ala Ile Thr Trp Ala Lys Thr Ile Ile Gly Arg Val Phe Gly Ser Asn
                405                 410                 415 gca gcc tcc cag cac atg ctg aag gca aag acc aca gct tcc ctg gcc     1296
Ala Ala Ser Gln His Met Leu Lys Ala Lys Thr Thr Ala Ser Leu Ala
            420                 425                 430 aac atc ttc ggc ttc tac act gca ccc aac tac cgg ttc tct tcc cag     1344
Asn Ile Phe Gly Phe Tyr Thr Ala Pro Asn Tyr Arg Phe Ser Ser Gln
        435                 440                 445 aag ttg gaa cag ctg gtg aag cag ttc gac act acc gag cag cga ctg     1392
Lys Leu Glu Gln Leu Val Lys Gln Phe Asp Thr Thr Glu Gln Arg Leu
    450                 455                 460 tac gac att cga gct gac cac ttc gac tgg aag tac tac ctg caa gag     1440
Tyr Asp Ile Arg Ala Asp His Phe Asp Trp Lys Tyr Tyr Leu Gln Glu
465                 470                 475                 480 gtt cac atg gat ggc ctt cac aag tac gct ttg gcc gat cgt cag gag     1488
Val His Met Asp Gly Leu His Lys Tyr Ala Leu Ala Asp Arg Gln Glu
                485                 490                 495 ctg aaa ccc aag cac gtg aag aag aga aag cgg gag act atc cga caa     1536
Leu Lys Pro Lys His Val Lys Lys Arg Lys Arg Glu Thr Ile Arg Gln
            500                 505                 510 gct gcg                                                              1542
Ala Ala
```

<210> SEQ ID NO 8
<211> LENGTH: 514
<212> TYPE: PRT
<213> ORGANISM: Artificial
<220> FEATURE:
<223> OTHER INFORMATION: Synthetic Construct

<400> SEQUENCE: 8

Met Ser Gln Tyr Ser Ala Phe Ser Val Ser Gln Ser Leu Lys Gly Lys
1               5                   10                  15

His Ile Phe Leu Thr Gly Val Thr Gly Phe Leu Gly Lys Ala Ile Leu
            20                  25                  30

Glu Lys Leu Leu Tyr Ser Val Pro Gln Leu Ala Gln Ile His Ile Leu
        35                  40                  45

Val Arg Gly Gly Lys Val Ser Ala Lys Lys Arg Phe Gln His Asp Ile
    50                  55                  60

Leu Gly Ser Ser Ile Phe Glu Arg Leu Lys Glu Gln His Gly Glu His
65                  70                  75                  80

Phe Glu Glu Trp Val Gln Ser Lys Ile Asn Leu Val Glu Gly Glu Leu
                85                  90                  95

Thr Gln Pro Met Phe Asp Leu Pro Ser Ala Glu Phe Ala Gly Leu Ala
            100                 105                 110

Asn Gln Leu Asp Leu Ile Ile Asn Ser Ala Ala Ser Val Asn Phe Arg
        115                 120                 125

Glu Asn Leu Glu Lys Ala Leu Asn Ile Asn Thr Leu Cys Leu Asn Asn
    130                 135                 140

Ile Ile Ala Leu Ala Gln Tyr Asn Val Ala Gln Thr Pro Val Met
145                 150                 155                 160

Gln Ile Ser Thr Cys Tyr Val Asn Gly Phe Asn Lys Gly Gln Ile Asn
                165                 170                 175

Glu Glu Val Val Gly Pro Ala Ser Gly Leu Ile Pro Gln Leu Ser Gln
            180                 185                 190

Asp Cys Tyr Asp Ile Asp Ser Val Phe Lys Arg Val His Ser Gln Ile
        195                 200                 205

Glu Gln Val Lys Lys Arg Lys Thr Asp Ile Glu Gln Gln Glu Gln Ala
    210                 215                 220

Leu Ile Lys Leu Gly Ile Lys Thr Ser Gln His Phe Gly Trp Asn Asp
225                 230                 235                 240

Thr Tyr Thr Phe Thr Lys Trp Leu Gly Glu Gln Leu Leu Ile Gln Lys
                245                 250                 255

Leu Gly Lys Gln Ser Leu Thr Ile Leu Arg Pro Ser Ile Ile Glu Ser
            260                 265                 270

Ala Val Arg Glu Pro Ala Pro Gly Trp Val Glu Gly Val Lys Val Ala
        275                 280                 285

Asp Ala Leu Ile Tyr Ala Tyr Ala Lys Gly Arg Val Ser Ile Phe Pro
    290                 295                 300

Gly Arg Asp Glu Gly Ile Leu Asp Val Ile Pro Val Asp Leu Val Ala
305                 310                 315                 320

Asn Ala Ala Ala Leu Ser Ala Ala Gln Leu Met Glu Ser Asn Gln Gln
                325                 330                 335

Thr Gly Tyr Arg Ile Tyr Gln Cys Cys Ser Gly Ser Arg Asn Pro Ile
            340                 345                 350

Lys Leu Lys Glu Phe Ile Arg His Ile Gln Asn Val Ala Gln Ala Arg
        355                 360                 365

Tyr Gln Glu Trp Pro Lys Leu Phe Ala Asp Lys Pro Gln Glu Ala Phe
    370                 375                 380

```
Lys Thr Val Ser Pro Lys Arg Phe Lys Leu Tyr Met Ser Gly Phe Thr
385                 390                 395                 400

Ala Ile Thr Trp Ala Lys Thr Ile Ile Gly Arg Val Phe Gly Ser Asn
            405                 410                 415

Ala Ala Ser Gln His Met Leu Lys Ala Lys Thr Thr Ala Ser Leu Ala
            420                 425                 430

Asn Ile Phe Gly Phe Tyr Thr Ala Pro Asn Tyr Arg Phe Ser Ser Gln
            435                 440                 445

Lys Leu Glu Gln Leu Val Lys Gln Phe Asp Thr Thr Glu Gln Arg Leu
            450                 455                 460

Tyr Asp Ile Arg Ala Asp His Phe Asp Trp Lys Tyr Leu Gln Glu
465                 470                 475                 480

Val His Met Asp Gly Leu His Lys Tyr Ala Leu Ala Asp Arg Gln Glu
                485                 490                 495

Leu Lys Pro Lys His Val Lys Lys Arg Lys Arg Glu Thr Ile Arg Gln
            500                 505                 510

Ala Ala

<210> SEQ ID NO 9
<211> LENGTH: 1383
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(1383)

<400> SEQUENCE: 9 atg tcc cac aat ggt act ctt gat gag cat tat cag aca gtt cgt gaa      48
Met Ser His Asn Gly Thr Leu Asp Glu His Tyr Gln Thr Val Arg Glu
1               5                   10                  15 ttt tat gac ggt aag agc gtt ttt att act ggc gcc act ggc ttt ctt      96
Phe Tyr Asp Gly Lys Ser Val Phe Ile Thr Gly Ala Thr Gly Phe Leu
                20                  25                  30 gga aaa gcc tac gtt gag aaa ctg gca tat tct tgt ccc gga att gtc     144
Gly Lys Ala Tyr Val Glu Lys Leu Ala Tyr Ser Cys Pro Gly Ile Val
            35                  40                  45 tct att tat att ttg att cgt gat aaa aag ggc tcc aac acg gag gag     192
Ser Ile Tyr Ile Leu Ile Arg Asp Lys Lys Gly Ser Asn Thr Glu Glu
        50                  55                  60 cgt atg cgt aaa tat ttg gac caa ccc att ttc tct cgt att aaa tat     240
Arg Met Arg Lys Tyr Leu Asp Gln Pro Ile Phe Ser Arg Ile Lys Tyr
65                  70                  75                  80 gag cat cca gag tac ttc aaa aag att atc ccc att tct ggc gat att     288
Glu His Pro Glu Tyr Phe Lys Lys Ile Ile Pro Ile Ser Gly Asp Ile
                85                  90                  95 acc gcc cct aaa ctt ggt ctt tgc gac gag gag cgt aac atc ctg att     336
Thr Ala Pro Lys Leu Gly Leu Cys Asp Glu Glu Arg Asn Ile Leu Ile
                100                 105                 110 aat gaa gtg tcc atc gtt atc cac tct gct gcc agc gtt aaa ctg aac     384
Asn Glu Val Ser Ile Val Ile His Ser Ala Ala Ser Val Lys Leu Asn
            115                 120                 125 gat cat ctt aaa ttc acc ttg aac acc aac gtt ggt ggt act atg aaa     432
Asp His Leu Lys Phe Thr Leu Asn Thr Asn Val Gly Gly Thr Met Lys
        130                 135                 140 gtc ttg gag ctt gtt aag gag atg aaa aat ttg gcg atg ttt gtg tac     480
Val Leu Glu Leu Val Lys Glu Met Lys Asn Leu Ala Met Phe Val Tyr
145                 150                 155                 160
```

```
gtt tct acg gct tat tct aac acc agc caa cgt att ttg gaa gaa aaa      528
Val Ser Thr Ala Tyr Ser Asn Thr Ser Gln Arg Ile Leu Glu Glu Lys
            165                 170                 175 ttg tac cct cag tct ctg aat ttg aac gaa att cag aaa ttc gct gaa      576
Leu Tyr Pro Gln Ser Leu Asn Leu Asn Glu Ile Gln Lys Phe Ala Glu
        180                 185                 190 gag cac tac att ctg ggt aag gat aac gac gaa atg att aaa ttc att      624
Glu His Tyr Ile Leu Gly Lys Asp Asn Asp Glu Met Ile Lys Phe Ile
    195                 200                 205 gga aac cat cct aac act tac gcc tac acg aaa gcc ctg gct gag aat      672
Gly Asn His Pro Asn Thr Tyr Ala Tyr Thr Lys Ala Leu Ala Glu Asn
210                 215                 220 ctt gtc gct gaa gaa cat gga gaa att cct act att att att cgt cct      720
Leu Val Ala Glu Glu His Gly Glu Ile Pro Thr Ile Ile Ile Arg Pro
225                 230                 235                 240 tct atc atc aca gcc tcc gcc gag gaa ccc gtt cgt gga ttt gtt gat      768
Ser Ile Ile Thr Ala Ser Ala Glu Glu Pro Val Arg Gly Phe Val Asp
            245                 250                 255 tct tgg agc gga gcc acg gct atg gct gca ttt gca ctt aaa ggc tgg      816
Ser Trp Ser Gly Ala Thr Ala Met Ala Ala Phe Ala Leu Lys Gly Trp
        260                 265                 270 aac aac atc atg tat tcc acc ggt gaa gag aac att gac ttg atc ccc      864
Asn Asn Ile Met Tyr Ser Thr Gly Glu Glu Asn Ile Asp Leu Ile Pro
    275                 280                 285 ctg gat tac gtt gtc aac ttg aca ctg gtg gct att gct aaa tat aag      912
Leu Asp Tyr Val Val Asn Leu Thr Leu Val Ala Ile Ala Lys Tyr Lys
290                 295                 300 cca acg aaa gag gtt acg gtg tac cat gtt aca acg agc gac ttg aac      960
Pro Thr Lys Glu Val Thr Val Tyr His Val Thr Thr Ser Asp Leu Asn
305                 310                 315                 320 ccg att agc atc cgt cgt att ttc atc aaa ctg agc gag ttc gcc tcc     1008
Pro Ile Ser Ile Arg Arg Ile Phe Ile Lys Leu Ser Glu Phe Ala Ser
            325                 330                 335 aaa aac cca act agc aac gct gcc cca ttc gct gcc act aca ttg ctg     1056
Lys Asn Pro Thr Ser Asn Ala Ala Pro Phe Ala Ala Thr Thr Leu Leu
        340                 345                 350 acc aaa cag aaa ccg ctt att aaa ctg gtg aca ttt ctt atg cag acc     1104
Thr Lys Gln Lys Pro Leu Ile Lys Leu Val Thr Phe Leu Met Gln Thr
    355                 360                 365 aca cca gct ttt ttg gca gac ttg tgg atg aaa acg cag cgt aaa gag     1152
Thr Pro Ala Phe Leu Ala Asp Leu Trp Met Lys Thr Gln Arg Lys Glu
370                 375                 380 gcc aag ttc gtg aaa cag cac aac ttg gtc gtt cgt tct cgt gat cag     1200
Ala Lys Phe Val Lys Gln His Asn Leu Val Val Arg Ser Arg Asp Gln
385                 390                 395                 400 ctg gag ttc ttt aca tct cag agc tgg ctt ttg cgt tgt gag cgt gca     1248
Leu Glu Phe Phe Thr Ser Gln Ser Trp Leu Leu Arg Cys Glu Arg Ala
            405                 410                 415 cgt gtc ctg tcc gcg gcc ttg tcc gat tcc gac cgt gct gtc ttc cgt     1296
Arg Val Leu Ser Ala Ala Leu Ser Asp Ser Asp Arg Ala Val Phe Arg
        420                 425                 430 tgc gat cct tcc acg att gat tgg gat cag tat ctt cct atc tac ttc     1344
Cys Asp Pro Ser Thr Ile Asp Trp Asp Gln Tyr Leu Pro Ile Tyr Phe
    435                 440                 445 gaa ggt att aat aaa cac ctg ttc aaa aat aag ttg tag                  1383
Glu Gly Ile Asn Lys His Leu Phe Lys Asn Lys Leu
450                 455                 460

<210> SEQ ID NO 10
<211> LENGTH: 460
<212> TYPE: PRT
```

<213> ORGANISM: Artificial
<220> FEATURE:
<223> OTHER INFORMATION: Synthetic Construct

<400> SEQUENCE: 10

```
Met Ser His Asn Gly Thr Leu Asp Glu His Tyr Gln Thr Val Arg Glu
1               5                   10                  15

Phe Tyr Asp Gly Lys Ser Val Phe Ile Thr Gly Ala Thr Gly Phe Leu
            20                  25                  30

Gly Lys Ala Tyr Val Glu Lys Leu Ala Tyr Ser Cys Pro Gly Ile Val
        35                  40                  45

Ser Ile Tyr Ile Leu Ile Arg Asp Lys Lys Gly Ser Asn Thr Glu Glu
50                  55                  60

Arg Met Arg Lys Tyr Leu Asp Gln Pro Ile Phe Ser Arg Ile Lys Tyr
65                  70                  75                  80

Glu His Pro Glu Tyr Phe Lys Lys Ile Pro Ile Ser Gly Asp Ile
                85                  90                  95

Thr Ala Pro Lys Leu Gly Leu Cys Asp Glu Arg Asn Ile Leu Ile
            100                 105                 110

Asn Glu Val Ser Ile Val Ile His Ser Ala Ala Ser Val Lys Leu Asn
            115                 120                 125

Asp His Leu Lys Phe Thr Leu Asn Thr Asn Val Gly Gly Thr Met Lys
130                 135                 140

Val Leu Glu Leu Val Lys Glu Met Lys Asn Leu Ala Met Phe Val Tyr
145                 150                 155                 160

Val Ser Thr Ala Tyr Ser Asn Thr Ser Gln Arg Ile Leu Glu Glu Lys
                165                 170                 175

Leu Tyr Pro Gln Ser Leu Asn Leu Asn Glu Ile Gln Lys Phe Ala Glu
            180                 185                 190

Glu His Tyr Ile Leu Gly Lys Asp Asn Asp Glu Met Ile Lys Phe Ile
            195                 200                 205

Gly Asn His Pro Asn Thr Tyr Ala Tyr Thr Lys Ala Leu Ala Glu Asn
210                 215                 220

Leu Val Ala Glu Glu His Gly Glu Ile Pro Thr Ile Ile Arg Pro
225                 230                 235                 240

Ser Ile Ile Thr Ala Ser Ala Glu Glu Pro Val Arg Gly Phe Val Asp
                245                 250                 255

Ser Trp Ser Gly Ala Thr Ala Met Ala Ala Phe Ala Leu Lys Gly Trp
            260                 265                 270

Asn Asn Ile Met Tyr Ser Thr Gly Glu Glu Asn Ile Asp Leu Ile Pro
            275                 280                 285

Leu Asp Tyr Val Val Asn Leu Thr Leu Val Ala Ile Ala Lys Tyr Lys
290                 295                 300

Pro Thr Lys Glu Val Thr Val Tyr His Val Thr Thr Ser Asp Leu Asn
305                 310                 315                 320

Pro Ile Ser Ile Arg Arg Ile Phe Ile Lys Leu Ser Glu Phe Ala Ser
                325                 330                 335

Lys Asn Pro Thr Ser Asn Ala Ala Pro Phe Ala Ala Thr Leu Leu
            340                 345                 350

Thr Lys Gln Lys Pro Leu Ile Lys Leu Val Thr Phe Leu Met Gln Thr
            355                 360                 365

Thr Pro Ala Phe Leu Ala Asp Leu Trp Met Lys Thr Gln Arg Lys Glu
370                 375                 380

Ala Lys Phe Val Lys Gln His Asn Leu Val Val Arg Ser Arg Asp Gln
385                 390                 395                 400
```

```
Leu Glu Phe Phe Thr Ser Gln Ser Trp Leu Leu Arg Cys Glu Arg Ala
                405                 410                 415

Arg Val Leu Ser Ala Ala Leu Ser Asp Ser Asp Arg Ala Val Phe Arg
            420                 425                 430

Cys Asp Pro Ser Thr Ile Asp Trp Asp Gln Tyr Leu Pro Ile Tyr Phe
            435                 440                 445

Glu Gly Ile Asn Lys His Leu Phe Lys Asn Lys Leu
    450                 455                 460

<210> SEQ ID NO 11
<211> LENGTH: 1380
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(1380)

<400> SEQUENCE: 11
```

| | | | | | | | | | | | | | | | | |
|---|---|---|---|---|---|---|---|---|---|---|---|---|---|---|---|---|
| atg | tct | cac | aac | gga | act | ctt | gac | gag | cat | tac | caa | act | gtg | cga | gag | 48 |
| Met | Ser | His | Asn | Gly | Thr | Leu | Asp | Glu | His | Tyr | Gln | Thr | Val | Arg | Glu | |
| 1 | | | | 5 | | | | | 10 | | | | | 15 | | |
| ttc | tac | gac | ggc | aaa | tcc | gtg | ttc | atc | acc | gga | gcc | act | gga | ttt | ctt | 96 |
| Phe | Tyr | Asp | Gly | Lys | Ser | Val | Phe | Ile | Thr | Gly | Ala | Thr | Gly | Phe | Leu | |
| | | | 20 | | | | | 25 | | | | | 30 | | | |
| ggt | aag | gca | tac | gtg | gag | aag | ctc | gct | tac | agc | tgt | ccc | ggt | atc | gtt | 144 |
| Gly | Lys | Ala | Tyr | Val | Glu | Lys | Leu | Ala | Tyr | Ser | Cys | Pro | Gly | Ile | Val | |
| | | | | 35 | | | | | 40 | | | | | 45 | | |
| tct | atc | tac | atc | ctg | att | aga | gat | aag | aag | ggc | tcc | aac | aca | gaa | gag | 192 |
| Ser | Ile | Tyr | Ile | Leu | Ile | Arg | Asp | Lys | Lys | Gly | Ser | Asn | Thr | Glu | Glu | |
| | 50 | | | | | 55 | | | | | 60 | | | | | |
| cgg | atg | cga | aag | tac | ctg | gac | cag | ccc | atc | ttc | tcc | cgg | atc | aag | tac | 240 |
| Arg | Met | Arg | Lys | Tyr | Leu | Asp | Gln | Pro | Ile | Phe | Ser | Arg | Ile | Lys | Tyr | |
| 65 | | | | | 70 | | | | | 75 | | | | | 80 | |
| gaa | cac | cct | gag | tac | ttc | aag | aag | atc | atc | ccc | att | agc | gga | gac | att | 288 |
| Glu | His | Pro | Glu | Tyr | Phe | Lys | Lys | Ile | Ile | Pro | Ile | Ser | Gly | Asp | Ile | |
| | | | | 85 | | | | | 90 | | | | | 95 | | |
| act | gcc | cca | aag | ctg | ggc | ttg | tgt | gac | gag | gag | cgg | aac | atc | ctg | atc | 336 |
| Thr | Ala | Pro | Lys | Leu | Gly | Leu | Cys | Asp | Glu | Glu | Arg | Asn | Ile | Leu | Ile | |
| | | | 100 | | | | | 105 | | | | | 110 | | | |
| aac | gag | gtg | tcc | atc | gtg | att | cat | tcc | gcc | gcc | tct | gtt | aag | ctg | aac | 384 |
| Asn | Glu | Val | Ser | Ile | Val | Ile | His | Ser | Ala | Ala | Ser | Val | Lys | Leu | Asn | |
| | | | | 115 | | | | | 120 | | | | | 125 | | |
| gac | cac | ctg | aag | ttc | acc | ctg | aac | act | aac | gtg | ggt | gga | acg | atg | aag | 432 |
| Asp | His | Leu | Lys | Phe | Thr | Leu | Asn | Thr | Asn | Val | Gly | Gly | Thr | Met | Lys | |
| | | 130 | | | | | 135 | | | | | 140 | | | | |
| gtc | ctg | gag | ctg | gtg | aag | gag | atg | aag | aac | ctg | gcc | atg | ttc | gtg | tac | 480 |
| Val | Leu | Glu | Leu | Val | Lys | Glu | Met | Lys | Asn | Leu | Ala | Met | Phe | Val | Tyr | |
| 145 | | | | | 150 | | | | | 155 | | | | | 160 | |
| gtg | tcc | acc | gct | tac | tcc | aac | acc | tct | cag | aga | atc | ctg | gag | gag | aag | 528 |
| Val | Ser | Thr | Ala | Tyr | Ser | Asn | Thr | Ser | Gln | Arg | Ile | Leu | Glu | Glu | Lys | |
| | | | | 165 | | | | | 170 | | | | | 175 | | |
| ctg | tac | cct | cag | tcc | ctg | aac | ctg | aac | gag | atc | cag | aag | ttc | gcc | gag | 576 |
| Leu | Tyr | Pro | Gln | Ser | Leu | Asn | Leu | Asn | Glu | Ile | Gln | Lys | Phe | Ala | Glu | |
| | | | 180 | | | | | 185 | | | | | 190 | | | |
| gaa | cac | tac | atc | ctg | ggc | aag | gac | aac | gac | gag | atg | atc | aag | ttc | atc | 624 |
| Glu | His | Tyr | Ile | Leu | Gly | Lys | Asp | Asn | Asp | Glu | Met | Ile | Lys | Phe | Ile | |
| | | | | 195 | | | | | 200 | | | | | 205 | | |
| ggc | aac | cac | ccc | aac | acc | tac | gct | tac | acc | aaa | gcc | ctg | gct | gag | aac | 672 |
| Gly | Asn | His | Pro | Asn | Thr | Tyr | Ala | Tyr | Thr | Lys | Ala | Leu | Ala | Glu | Asn | |

```
                         210                 215                 220
ctt gtt gcc gaa gag cat gga gag atc ccc acc atc atc atc cga ccc      720
Leu Val Ala Glu Glu His Gly Glu Ile Pro Thr Ile Ile Ile Arg Pro
225                 230                 235                 240 tct atc att act gca tcc gcg gag gag cct gtg cga ggc ttc gtc gat      768
Ser Ile Ile Thr Ala Ser Ala Glu Glu Pro Val Arg Gly Phe Val Asp
            245                 250                 255 tct tgg tct ggc gct act gct atg gct gct ttc gct ctc aag gga tgg      816
Ser Trp Ser Gly Ala Thr Ala Met Ala Ala Phe Ala Leu Lys Gly Trp
        260                 265                 270 aac aac atc atg tat tcc acc ggc gaa gag aac att gac ctg atc cct      864
Asn Asn Ile Met Tyr Ser Thr Gly Glu Glu Asn Ile Asp Leu Ile Pro
    275                 280                 285 ctc gac tac gtg gtg aac ctt acc ctg gtg gcc atc gct aag tac aag      912
Leu Asp Tyr Val Val Asn Leu Thr Leu Val Ala Ile Ala Lys Tyr Lys
290                 295                 300 cct acc aaa gag gtg acc gtg tac cac gtc acg act tcg gat ctg aat      960
Pro Thr Lys Glu Val Thr Val Tyr His Val Thr Thr Ser Asp Leu Asn
305                 310                 315                 320 ccc atc tcc atc cgg cga atc ttc atc aag ctg tct gag ttt gct tct     1008
Pro Ile Ser Ile Arg Arg Ile Phe Ile Lys Leu Ser Glu Phe Ala Ser
            325                 330                 335 aag aac ccg act tct aat gct gct cct ttc gct gcc act act ctg ctt     1056
Lys Asn Pro Thr Ser Asn Ala Ala Pro Phe Ala Ala Thr Thr Leu Leu
        340                 345                 350 acc aag cag aaa ccc ctg atc aag ctg gtt acg ttt ctg atg caa acc     1104
Thr Lys Gln Lys Pro Leu Ile Lys Leu Val Thr Phe Leu Met Gln Thr
    355                 360                 365 act cct gcc ttc ctc gct gac ctg tgg atg aag acc cag cga aag gag     1152
Thr Pro Ala Phe Leu Ala Asp Leu Trp Met Lys Thr Gln Arg Lys Glu
370                 375                 380 gcc aag ttc gtc aaa cag cat aac ctc gtc gtt aga tcg cga gat cag     1200
Ala Lys Phe Val Lys Gln His Asn Leu Val Val Arg Ser Arg Asp Gln
385                 390                 395                 400 ttg gag ttc ttt acc tcc cag tcc tgg ctg ctt cgt tgt gaa aga gcc     1248
Leu Glu Phe Phe Thr Ser Gln Ser Trp Leu Leu Arg Cys Glu Arg Ala
            405                 410                 415 aga gtg ctg tct gct gct ctt agc gac tct gat cgt gcc gtg ttt aga     1296
Arg Val Leu Ser Ala Ala Leu Ser Asp Ser Asp Arg Ala Val Phe Arg
        420                 425                 430 tgt gac ccc tcg aca atc gac tgg gat cag tac ctg ccc atc tac ttc     1344
Cys Asp Pro Ser Thr Ile Asp Trp Asp Gln Tyr Leu Pro Ile Tyr Phe
    435                 440                 445 gag ggc atc aac aag cac ctg ttc aag aac aag ctc                     1380
Glu Gly Ile Asn Lys His Leu Phe Lys Asn Lys Leu
450                 455                 460

<210> SEQ ID NO 12
<211> LENGTH: 460
<212> TYPE: PRT
<213> ORGANISM: Artificial
<220> FEATURE:
<223> OTHER INFORMATION: Synthetic Construct

<400> SEQUENCE: 12

Met Ser His Asn Gly Thr Leu Asp Glu His Tyr Gln Thr Val Arg Glu
1               5                   10                  15

Phe Tyr Asp Gly Lys Ser Val Phe Ile Thr Gly Ala Thr Gly Phe Leu
            20                  25                  30

Gly Lys Ala Tyr Val Glu Lys Leu Ala Tyr Ser Cys Pro Gly Ile Val
        35                  40                  45
```

```
Ser Ile Tyr Ile Leu Ile Arg Asp Lys Lys Gly Ser Asn Thr Glu Glu
        50                  55                  60

Arg Met Arg Lys Tyr Leu Asp Gln Pro Ile Phe Ser Arg Ile Lys Tyr
 65                  70                  75                  80

Glu His Pro Glu Tyr Phe Lys Lys Ile Ile Pro Ile Ser Gly Asp Ile
                85                  90                  95

Thr Ala Pro Lys Leu Gly Leu Cys Asp Glu Glu Arg Asn Ile Leu Ile
                100                 105                 110

Asn Glu Val Ser Ile Val Ile His Ser Ala Ala Ser Val Lys Leu Asn
                115                 120                 125

Asp His Leu Lys Phe Thr Leu Asn Thr Asn Val Gly Gly Thr Met Lys
                130                 135                 140

Val Leu Glu Leu Val Lys Glu Met Lys Asn Leu Ala Met Phe Val Tyr
145                 150                 155                 160

Val Ser Thr Ala Tyr Ser Asn Thr Ser Gln Arg Ile Leu Glu Glu Lys
                165                 170                 175

Leu Tyr Pro Gln Ser Leu Asn Leu Asn Glu Ile Gln Lys Phe Ala Glu
                180                 185                 190

Glu His Tyr Ile Leu Gly Lys Asp Asn Asp Glu Met Ile Lys Phe Ile
                195                 200                 205

Gly Asn His Pro Asn Thr Tyr Ala Tyr Thr Lys Ala Leu Ala Glu Asn
210                 215                 220

Leu Val Ala Glu Glu His Gly Glu Ile Pro Thr Ile Ile Arg Pro
225                 230                 235                 240

Ser Ile Ile Thr Ala Ser Ala Glu Glu Pro Val Arg Gly Phe Val Asp
                245                 250                 255

Ser Trp Ser Gly Ala Thr Ala Met Ala Ala Phe Ala Leu Lys Gly Trp
                260                 265                 270

Asn Asn Ile Met Tyr Ser Thr Gly Glu Glu Asn Ile Asp Leu Ile Pro
                275                 280                 285

Leu Asp Tyr Val Val Asn Leu Thr Leu Val Ala Ile Ala Lys Tyr Lys
                290                 295                 300

Pro Thr Lys Glu Val Thr Val Tyr His Val Thr Thr Ser Asp Leu Asn
305                 310                 315                 320

Pro Ile Ser Ile Arg Arg Ile Phe Ile Lys Leu Ser Glu Phe Ala Ser
                325                 330                 335

Lys Asn Pro Thr Ser Asn Ala Ala Pro Phe Ala Ala Thr Thr Leu Leu
                340                 345                 350

Thr Lys Gln Lys Pro Leu Ile Lys Leu Val Thr Phe Leu Met Gln Thr
                355                 360                 365

Thr Pro Ala Phe Leu Ala Asp Leu Trp Met Lys Thr Gln Arg Lys Glu
                370                 375                 380

Ala Lys Phe Val Lys Gln His Asn Leu Val Val Arg Ser Arg Asp Gln
385                 390                 395                 400

Leu Glu Phe Phe Thr Ser Gln Ser Trp Leu Leu Arg Cys Glu Arg Ala
                405                 410                 415

Arg Val Leu Ser Ala Ala Leu Ser Asp Ser Asp Arg Ala Val Phe Arg
                420                 425                 430

Cys Asp Pro Ser Thr Ile Asp Trp Asp Gln Tyr Leu Pro Ile Tyr Phe
                435                 440                 445

Glu Gly Ile Asn Lys His Leu Phe Lys Asn Lys Leu
                450                 455                 460
```

<210> SEQ ID NO 13
<211> LENGTH: 1542
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(1542)

<400> SEQUENCE: 13

| | | | | | | | | | | | | | | | | |
|---|---|---|---|---|---|---|---|---|---|---|---|---|---|---|---|---|
| atg | gct | atc | cag | cag | gtt | cat | cac | gcc | gac | aca | tcc | tcc | tct | aaa | gtc | 48 |
| Met | Ala | Ile | Gln | Gln | Val | His | His | Ala | Asp | Thr | Ser | Ser | Ser | Lys | Val | |
| 1 | | | | 5 | | | | | 10 | | | | | 15 | | |
| ctg | ggt | caa | ctt | cgt | ggt | aaa | cgt | gtc | ttg | att | acc | ggc | act | act | gga | 96 |
| Leu | Gly | Gln | Leu | Arg | Gly | Lys | Arg | Val | Leu | Ile | Thr | Gly | Thr | Thr | Gly | |
| | | 20 | | | | | 25 | | | | | 30 | | | | |
| ttc | ttg | ggt | aaa | gtc | gtc | ttg | gaa | cgt | ttg | att | cgt | gcc | gtt | cct | gac | 144 |
| Phe | Leu | Gly | Lys | Val | Val | Leu | Glu | Arg | Leu | Ile | Arg | Ala | Val | Pro | Asp | |
| | | | 35 | | | | | 40 | | | | | 45 | | | |
| atc | ggt | gct | atc | tac | ctg | ctg | att | cgt | ggt | aac | aag | cgt | cac | ccg | gat | 192 |
| Ile | Gly | Ala | Ile | Tyr | Leu | Leu | Ile | Arg | Gly | Asn | Lys | Arg | His | Pro | Asp | |
| | 50 | | | | | 55 | | | | | 60 | | | | | |
| gct | cgt | tct | cgt | ttc | ttg | gag | gag | att | gct | acc | tcc | tct | gtc | ttt | gat | 240 |
| Ala | Arg | Ser | Arg | Phe | Leu | Glu | Glu | Ile | Ala | Thr | Ser | Ser | Val | Phe | Asp | |
| 65 | | | | | 70 | | | | | 75 | | | | | 80 | |
| cgt | ttg | cgt | gaa | gct | gat | tcc | gaa | ggt | ttc | gat | gct | ttc | ctg | gaa | gaa | 288 |
| Arg | Leu | Arg | Glu | Ala | Asp | Ser | Glu | Gly | Phe | Asp | Ala | Phe | Leu | Glu | Glu | |
| | | | | 85 | | | | | 90 | | | | | 95 | | |
| cgt | att | cac | tgt | gtt | act | ggt | gaa | gtt | act | gaa | gct | ggt | ttc | ggt | att | 336 |
| Arg | Ile | His | Cys | Val | Thr | Gly | Glu | Val | Thr | Glu | Ala | Gly | Phe | Gly | Ile | |
| | | | 100 | | | | | 105 | | | | | 110 | | | |
| ggt | caa | gag | gac | tat | cgt | aag | ttg | gcc | acc | gaa | ttg | gac | gca | gtc | atc | 384 |
| Gly | Gln | Glu | Asp | Tyr | Arg | Lys | Leu | Ala | Thr | Glu | Leu | Asp | Ala | Val | Ile | |
| | | 115 | | | | | 120 | | | | | 125 | | | | |
| aat | tct | gct | gcc | tcc | gtc | aac | ttc | cgt | gag | gag | ttg | gat | aag | gct | ctg | 432 |
| Asn | Ser | Ala | Ala | Ser | Val | Asn | Phe | Arg | Glu | Glu | Leu | Asp | Lys | Ala | Leu | |
| | | 130 | | | | | 135 | | | | | 140 | | | | |
| gcc | atc | aac | act | ctg | tgt | ttg | cgt | aac | atc | gct | ggt | atg | gtg | gat | ctt | 480 |
| Ala | Ile | Asn | Thr | Leu | Cys | Leu | Arg | Asn | Ile | Ala | Gly | Met | Val | Asp | Leu | |
| 145 | | | | | 150 | | | | | 155 | | | | | 160 | |
| aac | cct | aag | ctg | gcc | gtt | ctt | caa | gtc | tct | acg | tgt | tac | gtc | aac | ggt | 528 |
| Asn | Pro | Lys | Leu | Ala | Val | Leu | Gln | Val | Ser | Thr | Cys | Tyr | Val | Asn | Gly | |
| | | | | 165 | | | | | 170 | | | | | 175 | | |
| atg | aac | tct | ggt | caa | gtt | act | gaa | tcc | gtc | atc | aaa | cca | gct | ggt | gaa | 576 |
| Met | Asn | Ser | Gly | Gln | Val | Thr | Glu | Ser | Val | Ile | Lys | Pro | Ala | Gly | Glu | |
| | | | 180 | | | | | 185 | | | | | 190 | | | |
| gct | gtt | cct | cgt | tct | cct | gat | gga | ttc | tac | gag | atc | gag | gaa | ttg | gtt | 624 |
| Ala | Val | Pro | Arg | Ser | Pro | Asp | Gly | Phe | Tyr | Glu | Ile | Glu | Glu | Leu | Val | |
| | | 195 | | | | | 200 | | | | | 205 | | | | |
| cgt | ctg | ctg | caa | gac | aag | att | gaa | gac | gtt | caa | gca | cgt | tac | tct | ggt | 672 |
| Arg | Leu | Leu | Gln | Asp | Lys | Ile | Glu | Asp | Val | Gln | Ala | Arg | Tyr | Ser | Gly | |
| | | 210 | | | | | 215 | | | | | 220 | | | | |
| aag | gtg | ttg | gag | cgt | aag | ttg | gtt | gat | ttg | ggt | att | cgt | gag | gct | aat | 720 |
| Lys | Val | Leu | Glu | Arg | Lys | Leu | Val | Asp | Leu | Gly | Ile | Arg | Glu | Ala | Asn | |
| 225 | | | | | 230 | | | | | 235 | | | | | 240 | |
| cgt | tac | ggt | tgg | tct | gat | aca | tac | acc | ttc | acg | aaa | tgg | ttg | ggt | gaa | 768 |
| Arg | Tyr | Gly | Trp | Ser | Asp | Thr | Tyr | Thr | Phe | Thr | Lys | Trp | Leu | Gly | Glu | |
| | | | | 245 | | | | | 250 | | | | | 255 | | |
| caa | ctt | ctg | atg | aaa | gcc | ttg | aat | ggt | cgt | acc | ttg | act | att | ctg | cgt | 816 |
| Gln | Leu | Leu | Met | Lys | Ala | Leu | Asn | Gly | Arg | Thr | Leu | Thr | Ile | Leu | Arg | |
| | | | 260 | | | | | 265 | | | | | 270 | | | |

```
cct agc atc att gaa tct gct ttg gaa gaa cca gca cct ggt tgg att         864
Pro Ser Ile Ile Glu Ser Ala Leu Glu Glu Pro Ala Pro Gly Trp Ile
        275                 280                 285 gaa ggc gtg aaa gtt gca gat gcg atc atc ttg gct tat gct cgt gag         912
Glu Gly Val Lys Val Ala Asp Ala Ile Ile Leu Ala Tyr Ala Arg Glu
    290                 295                 300 aag gtt act ttg ttt ccg ggt aaa cgt tct ggt atc att gat gtg att         960
Lys Val Thr Leu Phe Pro Gly Lys Arg Ser Gly Ile Ile Asp Val Ile
305                 310                 315                 320 cct gtt gac ttg gtt gcc aat tcc atc atc ttg tct ttg gct gag gct        1008
Pro Val Asp Leu Val Ala Asn Ser Ile Ile Leu Ser Leu Ala Glu Ala
                325                 330                 335 ctg ggc gaa cct ggt cgt cgt cgt atc tac caa tgt tgt tct ggt ggt        1056
Leu Gly Glu Pro Gly Arg Arg Arg Ile Tyr Gln Cys Cys Ser Gly Gly
            340                 345                 350 ggt aat cct atc tcc ctg ggc gag ttc att gat cac ctg atg gct gaa        1104
Gly Asn Pro Ile Ser Leu Gly Glu Phe Ile Asp His Leu Met Ala Glu
        355                 360                 365 tcc aaa gcc aac tat gcc gca tac gat cat ctg ttc tac cgt caa ccc        1152
Ser Lys Ala Asn Tyr Ala Ala Tyr Asp His Leu Phe Tyr Arg Gln Pro
    370                 375                 380 tcc aag cct ttc ctt gct gtc aac cgt gct ttg ttc gac ttg gtt atc        1200
Ser Lys Pro Phe Leu Ala Val Asn Arg Ala Leu Phe Asp Leu Val Ile
385                 390                 395                 400 tct ggt gtc cgt ctg cct ttg tct ttg acc gac cgt gtc ttg aag ctg        1248
Ser Gly Val Arg Leu Pro Leu Ser Leu Thr Asp Arg Val Leu Lys Leu
                405                 410                 415 ctg ggc aac tcc cgt gac ctg aag atg ctg cgt aac ctg gat act acg        1296
Leu Gly Asn Ser Arg Asp Leu Lys Met Leu Arg Asn Leu Asp Thr Thr
            420                 425                 430 caa tcc ctg gct act atc ttt ggc ttc tac aca gcc ccc gac tac atc        1344
Gln Ser Leu Ala Thr Ile Phe Gly Phe Tyr Thr Ala Pro Asp Tyr Ile
        435                 440                 445 ttc cgt aat gac gag ttg atg gcc ctg gct aac cgt atg ggc gag gtt        1392
Phe Arg Asn Asp Glu Leu Met Ala Leu Ala Asn Arg Met Gly Glu Val
    450                 455                 460 gat aag ggt ttg ttc ccc gtt gat gct cgt ctg att gat tgg gaa ttg        1440
Asp Lys Gly Leu Phe Pro Val Asp Ala Arg Leu Ile Asp Trp Glu Leu
465                 470                 475                 480 tac ctg cgt aag att cac ctg gct ggt ttg aac cgt tac gcc ttg aag        1488
Tyr Leu Arg Lys Ile His Leu Ala Gly Leu Asn Arg Tyr Ala Leu Lys
                485                 490                 495 gag cgt aag gtt tac tct ttg aag aca gcc cgt cag cgt aag aag gca        1536
Glu Arg Lys Val Tyr Ser Leu Lys Thr Ala Arg Gln Arg Lys Lys Ala
            500                 505                 510 gct taa                                                                 1542
Ala <210> SEQ ID NO 14
<211> LENGTH: 513
<212> TYPE: PRT
<213> ORGANISM: Artificial
<220> FEATURE:
<223> OTHER INFORMATION: Synthetic Construct

<400> SEQUENCE: 14

Met Ala Ile Gln Gln Val His His Ala Asp Thr Ser Ser Ser Lys Val
1               5                   10                  15

Leu Gly Gln Leu Arg Gly Lys Arg Val Leu Ile Thr Gly Thr Thr Gly
            20                  25                  30

Phe Leu Gly Lys Val Val Leu Glu Arg Leu Ile Arg Ala Val Pro Asp
```

```
                35                  40                  45
Ile Gly Ala Ile Tyr Leu Leu Ile Arg Gly Asn Lys Arg His Pro Asp
 50                  55                  60

Ala Arg Ser Arg Phe Leu Glu Glu Ile Ala Thr Ser Ser Val Phe Asp
 65                  70                  75                  80

Arg Leu Arg Glu Ala Asp Ser Glu Gly Phe Asp Ala Phe Leu Glu Glu
                 85                  90                  95

Arg Ile His Cys Val Thr Gly Glu Val Thr Glu Ala Gly Phe Gly Ile
                100                 105                 110

Gly Gln Glu Asp Tyr Arg Lys Leu Ala Thr Glu Leu Asp Ala Val Ile
                115                 120                 125

Asn Ser Ala Ala Ser Val Asn Phe Arg Glu Glu Leu Asp Lys Ala Leu
130                 135                 140

Ala Ile Asn Thr Leu Cys Leu Arg Asn Ile Ala Gly Met Val Asp Leu
145                 150                 155                 160

Asn Pro Lys Leu Ala Val Leu Gln Val Ser Thr Cys Tyr Val Asn Gly
                165                 170                 175

Met Asn Ser Gly Gln Val Thr Glu Ser Val Ile Lys Pro Ala Gly Glu
                180                 185                 190

Ala Val Pro Arg Ser Pro Asp Gly Phe Tyr Glu Ile Glu Glu Leu Val
                195                 200                 205

Arg Leu Leu Gln Asp Lys Ile Glu Asp Val Gln Ala Arg Tyr Ser Gly
                210                 215                 220

Lys Val Leu Glu Arg Lys Leu Val Asp Leu Gly Ile Arg Glu Ala Asn
225                 230                 235                 240

Arg Tyr Gly Trp Ser Asp Thr Tyr Thr Phe Thr Lys Trp Leu Gly Glu
                245                 250                 255

Gln Leu Leu Met Lys Ala Leu Asn Gly Arg Thr Leu Thr Ile Leu Arg
                260                 265                 270

Pro Ser Ile Ile Glu Ser Ala Leu Glu Glu Pro Ala Pro Gly Trp Ile
                275                 280                 285

Glu Gly Val Lys Val Ala Asp Ala Ile Ile Leu Ala Tyr Ala Arg Glu
                290                 295                 300

Lys Val Thr Leu Phe Pro Gly Lys Arg Ser Gly Ile Ile Asp Val Ile
305                 310                 315                 320

Pro Val Asp Leu Val Ala Asn Ser Ile Ile Leu Ser Leu Ala Glu Ala
                325                 330                 335

Leu Gly Glu Pro Gly Arg Arg Arg Ile Tyr Gln Cys Cys Ser Gly Gly
                340                 345                 350

Gly Asn Pro Ile Ser Leu Gly Glu Phe Ile Asp His Leu Met Ala Glu
                355                 360                 365

Ser Lys Ala Asn Tyr Ala Ala Tyr Asp His Leu Phe Tyr Arg Gln Pro
370                 375                 380

Ser Lys Pro Phe Leu Ala Val Asn Arg Ala Leu Phe Asp Leu Val Ile
385                 390                 395                 400

Ser Gly Val Arg Leu Pro Leu Ser Leu Thr Asp Arg Val Leu Lys Leu
                405                 410                 415

Leu Gly Asn Ser Arg Asp Leu Lys Met Leu Arg Asn Leu Asp Thr Thr
                420                 425                 430

Gln Ser Leu Ala Thr Ile Phe Gly Phe Tyr Thr Ala Pro Asp Tyr Ile
                435                 440                 445

Phe Arg Asn Asp Glu Leu Met Ala Leu Ala Asn Arg Met Gly Glu Val
450                 455                 460
```

```
Asp Lys Gly Leu Phe Pro Val Asp Ala Arg Leu Ile Asp Trp Glu Leu
465                 470                 475                 480

Tyr Leu Arg Lys Ile His Leu Ala Gly Leu Asn Arg Tyr Ala Leu Lys
                485                 490                 495

Glu Arg Lys Val Tyr Ser Leu Lys Thr Ala Arg Gln Arg Lys Lys Ala
            500                 505                 510

Ala

<210> SEQ ID NO 15
<211> LENGTH: 42
<212> TYPE: DNA
<213> ORGANISM: Artificial
<220> FEATURE:
<223> OTHER INFORMATION: Synthetic

<400> SEQUENCE: 15
acaatctgga tccggccagc ctggccataa ggagatatac at                        42

<210> SEQ ID NO 16
<211> LENGTH: 34
<212> TYPE: DNA
<213> ORGANISM: Artificial
<220> FEATURE:
<223> OTHER INFORMATION: Synthetic

<400> SEQUENCE: 16
taatgaggcc aaactggccg tcgacaccag tatg                                 34

<210> SEQ ID NO 17
<211> LENGTH: 17
<212> TYPE: DNA
<213> ORGANISM: Artificial
<220> FEATURE:
<223> OTHER INFORMATION: Synthetic primer

<400> SEQUENCE: 17
agagaccggg ttggcgg                                                    17

<210> SEQ ID NO 18
<211> LENGTH: 21
<212> TYPE: DNA
<213> ORGANISM: Artificial
<220> FEATURE:
<223> OTHER INFORMATION: Synthetic primer

<400> SEQUENCE: 18
catttgccat tcgtaacgct g                                               21
```